(12) United States Patent
Segovia et al.

(10) Patent No.: US 11,286,501 B2
(45) Date of Patent: Mar. 29, 2022

(54) METHODS OF TREATING OR PREVENTING PYRUVATE KINASE DEFICIENCY

(71) Applicants: Centro de Investigaciones Energéticas, Medioambientales y Tecnológicas, O.A., M.P., Madrid (ES); Fundación Instituto de Investigación Sanitaria Fundación Jiménez Diaz, Madrid (ES); Consorcio Centro de Investigación Biomédica en Red, M.P., Madrid (ES)

(72) Inventors: Jose C. Segovia, Madrid (ES); Maria G. Gomez, London (GB); Susana Navarro, Madrid (ES); Nestor Meza, San Cristobal (VE); Juan Bueren, Madrid (ES); Maria G. Bravo, Madrid (ES)

(73) Assignees: CENTRO DE INVESTIGACIONES ENERGETICAS, MEDIOAMBIENTALES Y TECNOLOGICAS O.A, M.P., Madrid (ES); CONSORCIO CENTRO DE INVESTIGACION BIOMFDICA EN RED, M.P., Madrid (ES); FUNDACION INSTITUTO DE INVESTIGACION SANITARIA FUNDACION JIMENEZ DIAZ, Madrid (ES)

( * ) Notice: Subject to any disclaimer, the term of this patent is extended or adjusted under 35 U.S.C. 154(b) by 401 days.

(21) Appl. No.: 16/094,414

(22) PCT Filed: Apr. 20, 2017

(86) PCT No.: PCT/US2017/028695
§ 371 (c)(1),
(2) Date: Oct. 17, 2018

(87) PCT Pub. No.: WO2017/184903
PCT Pub. Date: Oct. 26, 2017

(65) Prior Publication Data
US 2019/0284573 A1 Sep. 19, 2019

Related U.S. Application Data

(60) Provisional application No. 62/325,397, filed on Apr. 20, 2016.

(51) Int. Cl.
| | |
|---|---|
| *C12N 15/63* | (2006.01) |
| *C12N 15/86* | (2006.01) |
| *A61K 35/28* | (2015.01) |
| *A61K 48/00* | (2006.01) |
| *C12N 5/078* | (2010.01) |
| *C12N 9/12* | (2006.01) |
| *C12N 15/79* | (2006.01) |

(52) U.S. Cl.
CPC ............ *C12N 15/86* (2013.01); *A61K 35/28* (2013.01); *A61K 48/005* (2013.01); *C12N 5/0641* (2013.01); *C12N 9/1205* (2013.01); *C12N 15/63* (2013.01); *C12Y 207/0104* (2013.01); *C12N 15/79* (2013.01); *C12N 2510/00* (2013.01); *C12N 2740/16043* (2013.01); *C12N 2800/22* (2013.01); *C12N 2830/48* (2013.01)

(58) Field of Classification Search
CPC .... C12N 15/86; C12N 5/0641; C12N 9/1205; C12N 15/63; C12N 15/79; C12N 2510/00; C12N 2740/16043; C12N 2800/22; C12N 2830/48; A61K 35/28; A61K 48/005; C12Y 207/0104
See application file for complete search history.

(56) References Cited

U.S. PATENT DOCUMENTS

| | | | |
|---|---|---|---|
| 5,126,260 A | 6/1992 | Tuan et al. | |
| 6,027,721 A | 2/2000 | Hammang et al. | |
| 6,136,597 A | 10/2000 | Hope et al. | |
| 6,607,879 B1 | 8/2003 | Cocks et al. | |
| 7,198,950 B2 | 4/2007 | Trono et al. | |
| 7,575,924 B2 | 8/2009 | Trono et al. | |
| 7,629,153 B2 | 12/2009 | Trono et al. | |
| 8,093,042 B2 | 1/2012 | Charneau et al. | |
| 8,329,462 B2 | 12/2012 | Trono et al. | |
| 8,727,132 B2 | 5/2014 | Miltenyi et al. | |
| 8,741,608 B2 | 6/2014 | Claes et al. | |
| 8,748,169 B2 | 6/2014 | Trono et al. | |
| 8,900,858 B2 | 12/2014 | Trono et al. | |
| 9,175,077 B2 | 11/2015 | Gallo et al. | |
| 9,340,798 B2 | 5/2016 | Trono et al. | |

(Continued)

FOREIGN PATENT DOCUMENTS

| | | |
|---|---|---|
| CN | 104020298 A | 9/2014 |
| JP | 2006-524051 A | 10/2006 |

(Continued)

OTHER PUBLICATIONS

US 5,891,715 A, 04/1999, Haddada et al. (withdrawn)

(Continued)

*Primary Examiner* — Catherine S Hibbert
(74) *Attorney, Agent, or Firm* — Cooley LLP

(57) ABSTRACT

The present disclosure provides polynucleotide cassettes, expression vectors and methods for the expression of a gene in mammalian cells to provide gene therapy for pyruvate kinase deficiency.

19 Claims, 37 Drawing Sheets
Specification includes a Sequence Listing.

(56) References Cited

U.S. PATENT DOCUMENTS

| | | |
|---|---|---|
| 2003/0138868 A1 | 7/2003 | Jungblut et al. |
| 2006/0200869 A1 | 9/2006 | Naldini et al. |
| 2009/0111106 A1 | 4/2009 | Mitrophanous et al. |
| 2012/0083587 A1 | 4/2012 | Gallo et al. |
| 2014/0010861 A1 | 1/2014 | Bancel et al. |
| 2014/0220678 A1 | 8/2014 | Trono et al. |
| 2015/0031134 A1 | 1/2015 | Zhang et al. |
| 2021/0187126 A1 | 6/2021 | Sanz et al. |

FOREIGN PATENT DOCUMENTS

| | | |
|---|---|---|
| JP | 2007-054069 A | 3/2007 |
| RU | 2233333 C2 | 7/2004 |
| RU | 2280074 C2 | 7/2006 |
| WO | WO-03/066086 A2 | 8/2003 |
| WO | WO-03/066086 A3 | 8/2003 |
| WO | WO-2008/125720 A1 | 10/2008 |
| WO | WO-2008/136670 A2 | 11/2008 |
| WO | WO-2008/136670 A3 | 11/2008 |
| WO | WO-2015/056014 A1 | 4/2015 |
| WO | WO-2016/118780 A1 | 7/2016 |
| WO | WO-2017/077135 A1 | 5/2017 |
| WO | WO-2017/184903 A1 | 10/2017 |

OTHER PUBLICATIONS

Garcia-Gomez et al in the inventors own work published Jul. 2016, entitled "Safe and Efficient Gene Therapy for Pyruvate Kinase Deficiency" (Molecular Therapy vol. 24, No. 7, pp. 1187-1198). (Year: 2016).*

Aluti, A. et al. (2013). "Lentiviral hematopoietic stem cell gene therapy in patients with Wiskott-Aldrich syndrome," Science 341:1233151.

Albrechtsen, B. et al. (1991). Transcriptional termination sequence at the end of the *Escherichia coli* ribosomal RNA G operon: Complex terminators and antitermination, Nucl. Acids Res. 19:1845-1852.

Almarza, E. et al. (2011). "Correction of SCID-X1 using an enhancerless Vav promoter," Hum. Gene Ther. 22:263-270.

Berge, S.M. et al. (1977). Pharmaceutical Salts, J. Pharma Sci. 66:1-19.

Beutler, E. et al. (2000). "Estimating the prevalence of pyruvate kinase deficiency from the gene frequency in the general white population," Blood 95:3585-3588.

Biffi, A. et al. (2013). "Lentiviral hematopoietic stem cell gene therapy benefits metachromatic leukodystrophy," Science 341:1233158.

Braun, C.J. et al. (2014). "Gene therapy for Wiskott-Aldrich syndrome—long-term efficacy and genotoxicity," Sci. Transl. Med. 6:227ra33.

Breda, L. et al. (2012). "Therapeutic hemoglobin levels after gene transfer in β-thalassemia mice and in hematopoietic cells of β-thalassemia and sickle cells disease patients," PLoS One 7:e32345.

Cartier, N, et al. (2009). "Hematopoietic stem cell gene therapy with a lentiviral vector in X-linked adrenoleukodystrophy," Science 326:818-823.

Cartier, N. et al. (2012). "Lentiviral hematopoietic cell gene therapy for X-linked adrenoleukodystrophy," Methods Enzymol. 507:187-198.

Cavazzana-Calvo, M. et al. (2010). "Transfusion independence and HMGA2 activation after gene therapy of human β-thalassaemia," Nature 467:318-322.

Charrier, S. et al. (2005). "A lentiviral vector encoding the human Wiskott-Aldrich syndrome protein corrects immune and cytoskeletal defects in WASP knockout mice," Gene Ther. 12:597-606.

Charrier et al. (2011). "Quantification of lentiviral vector copy numbers in individual hematopoietic colony-forming cells shows vector dose-dependent effects on the frequency and level of transduction," Gene Ther. 18:479-487.

Craddock, C.F. et al. (1997). Antibodies to VLA4 integrin mobilize long-term repopulating cells and augment cytokine-induced mobilization in primates and mice, Blood 90:4779-4788.

Donello, J.E. et al. (1998). "Woodchuck hepatitis virus contains a tripartite posttranscriptional regulatory element," J. Virol. 72:5085-5092.

Dull, T. et al. (1998). "A third-generation lentivirus vector with a conditional packaging system," J. Virol. 72:8463-8471.

Ellis, J. (2005). "Silencing and variegation of gammaretrovirus and lentivirus vectors," Hum. Gene Ther. 16:1241-1246.

Extended European Search Report dated Nov. 27, 2019, for EP Application No. 17 786 662.1, filed on Apr. 20, 2017, 7 pages.

GenBank Accession No. XP016856982.1 (2020). Pyruvate kinase PKLR isoform X2 [*Homo sapiens*], 1 total page.

Garate, Z. et al. (2015). "Generation of a High Number of Healthy Erythroid Cells from Gene-Edited Pyruvate Kinase Deficiency Patient-Specific Induced Pluripotent Stem Cells," Stem Cell Reports 5:1053-1066.

GenBank Accession No. XP011507942.1 (2020). Pyruvate kinase PKLR isoform X1 [*Homo sapiens*], 2 total pages.

GenBank Accession No. XP006711449.1 (2020). Pyruvate kinase PKLR isoform X1 [*Homo sapiens*], 2 total pages.

GenBank Accession No. NP870986.1 (2020). Pyruvate kinase PKLR isoform 2 [*Homo sapiens*], 3 total pages.

GenBank Accession No. NP000289.1. (2020). Pyruvate kinase PKLR isoform 1 [*Homo sapiens*], 4 total pages.

Gerolami, R. et al. (2000). "Gene transfer to hepatocellular carcinoma: transduction efficacy and transgene expression kinetics by using retroviral and lentiviral vectors," Cancer Gene Ther. 7:1286-1292.

Ginn, S.L. et al. (2003). "Promoter interference mediated by the U3 region in early-generation HIV-1-derived lentivirus vectors can influence detection of transgene expression in a cell-type and species-specific manner," Hum. Gene Ther. 14:1127-1137.

Good, N.E. et al. (1966). Hydrogen ion buffers for biological research, Biochemistry 5:467-477.

Groeschel, S. et al. (2011). "Metachromatic leukodystrophy: Natural course of cerebral MRI changes in relation to clinical course," J. Inherit. Metab. Dis. 34:1095-1102.

Hacein-Bey-Abina, S. et al. (2008). "Insertional oncogenesis in 4 patients after retrovirus-mediated gene therapy of SCID-X1," J. Clin. Invest. 118:3132-3142.

Hilgard et al. (2005). "Liver cirrhosis as a consequence of iron overload caused by hereditary nonspherocytic hemolytic anemia," World J. Gastroenterol. 11:1241-1244.

Hlavaty, J. et al. (2005). "Effect of posttranscriptional regulatory elements on transgene expression and virus production in the context of retrovirus vectors," Virology 341:1-11.

Howe, S.J. et al. (2008). "Insertional mutagenesis combined with acquired somatic mutations causes leukemogenesis following gene therapy of SCID-X1 patients," J. Clin. Invest. 118:3143-3150.

International Search Report dated Jan. 11, 2019, for PCT Application No. PCT/US2018/056136, filed on Oct. 16, 2018, 4 pages.

Iwakuma, T. et al. (1999). "Self-inactivating lentiviral vectors with U3 and U5 modifications," Virology 261:120-132.

Jin, P. et al. (2008). Differentiation of two types of mobilized peripheral blood stem sets by microRNA and cDNA expression analysis, J. Translational Med. 6:39.

Kanno, H. et al. Transgenic rescue of hemolytic anemia due to red blood cell pyruvate kinase deficiency. Haemotologica.i. Jun. 2007. vol. 92, No. 6, pp. 731-737.

Kanno, H. et al. (1992). "Structural analysis of human pyruvate kinase L-gene and identification of the promoter activity in erythroid cells," Biochem. Biophys. Res. Commun. 188:516-523.

Kingsman, S.M. et al. (2005). Potential oncogene activity of the Woodchuck Hepatitis post-transcriptional regulatory element (WPRE), Gene Ther. 12:3-4.

Koda, H. et al. (1984). Antibody synthesis by bone marrow cells in vitro following primary and booster tetanus toxoid immunization in humans, J. Clin. Invest. 73:1377-1384.

LOVD[3] (2020). The PKLR gene homepage, located at https://databases.lovd.nl/shared/genes/PKLR, 1 total page.

Meza, N.W. et al. (2007). "Development of efficient gene therapy for the treatment of Erythrocyte Pyruvate kinase deficiency," Blood 110:2584-2584.

(56) References Cited

OTHER PUBLICATIONS

Mitchell, R.S. et al. (2004). Retroviral DNA integration: ASLV, HIV, and MLV show distinct target site preferences, PLoS Biol. 2:E234.
Miyoshi, H. et al. (1998). "Development of a self-inactivating lentivirus vector," J. Virol. 72:8150-8157.
Modlich, U. et al. (2009). Insertional Transformation of Hematopoietic Cells by Self-Inactivating Lentiviral and Gammaretroviral Vectors, Mol Ther. 17:1919-1928.
Navarro, S. et al. (2006). "Hematopoietic dysfunction in a mouse model for Fanconi anemia group D1," Mol. Ther. 14:525-535.
Noguchi, T. et al. (1987). "The L- and R-type isozymes of rat pyruvate kinase are produced from a single gene by use of different promoters," J. Biol. Chem. 262:14366-14371.
Oh, T. et al. (2007). "Lentiviral vector design using alternative RNA export elements," Retrovirology 4:38.
Ott, M.G. et al. (2006). "Correction of X-linked chronic granulomatous disease by gene therapy, augmented by insertional activation of MDS1-EVI1, PRDM16 or SETBP1," Nat. Med. 12:401-409.
Papayannopoulou, T. et al. (1998). Anti-VLA4/VCAM-1-induced mobilization requires cooperative signaling through the kit/mkit ligand pathway, Blood 91:2231-2239.
Paruzynski, A. et al. (2010). "Genome—wide high-throughput integrome analyses by nrLAM-PCR and next-generation sequencing," Nat. Protoc. 5:1379-1395.
Pelus, L.M. (2008). Peripheral blood stream cell mobilization: New regimens, new cells, where do we stand, Curr. Opin. Hematol. 15:285-292.
Pestina, T.I. et al. (2009). "Correction of murine sickle cell disease using gamma-globin lentiviral vectors to mediate high-level expression of fetal hemoglobin," Mol. Ther. 17:245-252.
Pfeifer, A. et al. (2002). "Transgenesis by lentiviral vectors: Lack of gene silencing in mammalian embryonic stem cells and preimplementation embryos," PNAS 99:2140-2145.
Pissard et al. (2006). "Pyruvate kinase deficiency in France: a 3-year study reveals 27 new mutations," Br. J. Haematol. 133:683-689.
Richard, R.E. et al. (2004). "Modulating erythrocyte chimerism in a mouse model of pyruvate kinase deficiency," Blood 103:4432-4439.
Salmon, P. et al. (2000). "High-level transgene expression in human hematopoietic progenitors and differentiated blood lineages after transduction with improved lentiviral vectors," Blood 96:3392-3398.
Schambach, A. et al. (2006). Woodchuck hepatitis virus post-transcriptional regulatory element deleted from X protein and promoter sequences enhances retroviral vector titer and expression, Gene Ther. 13:641-645.
Schmidt, M. et al. (2007). "High-resolution insertion-site analysis by linear amplification-mediated PCR (LAM-PCR)," Nat. Methods 4:1051-1057.
Schroder, A.R.W. et al. (2002). HIV-1 integration in the human genome favors active genes and local hotspots, Cell 110:521-529.
Sevilla, J. et al. (2016). Immunomagnetic T cell depletion: An analysis of variables affecting final cell yield, Clin. Lab. 62:1243-1248.
Socolovsky, M. et al. (2001). "Ineffective erythropoiesis in Stat5a(-/-)5b(-/-) mice due to decreased survival of early erythroblasts," Blood 98:3261-3273.
Stein, S. et al. (2010). "Genomic Instability and myelodysplasia with monosomy 7 consequent to EVI1 activation after gene therapy for chronic granulomatous disease," Nat. Med. 16:198-204.
Tricot, G. et al. (2008). Mobilization of peripheral blood stem cells in myeloma with either pegfilgrastim or filgrastim following chemotherapy, Haematologica 93:1739-1742.
Weaver, C.H. et al. (2001). Mobilization of peripheral blood stem cells following myelosuppressive chemotherapy: A randomized comparison of filgrastim, sargramostim, or sequential sargramostim and filgrastim, Bone Marrow Transplantation 27:S23-S29.

Written Opinion of the International Searching Authority dated Jan. 11, 2019, for PCT Application No. PCT/US2018/056136, filed on Oct. 16, 2018, 4 pages.
Zaiss, A-K. et al. (2002). "RNA 3' readthrough of oncoretrovirus and lentivirus: Implications for vector safety and efficacy," J. Virol. 76:7209-7219.
Zufferey, R. et al. (1999). "Woodchuck Hepatitis Virus Post-transcriptional Regulatory Element Enhances Expression of Transgenes Delivered by Retroviral Vectors," Journal of Virology 73:2886-2892.
Zufferey, R. et al. (1998). Self-inflicting lentivirus vector for safe and efficient In Vivo gene delivery, J. Virol. 72:9873-9880.
Cid-Arregui, A. et al. (2003). A synthetic E7 gene of human papillomavirus type 16 that yields enhanced expression of the protein in mammalian cells and is useful for DNA immunization studies, J. Virol. 77:4928.
Follenzi, A. et al. (2000). Gene transfer by lentiviral vectos is limited by nuclear translocation and rescued by HIV-1 pol sequences, Nat. Genet. 25:217-222.
Garica-Gomez, M. et al. (2016). Safe and efficient gene therapy for pyruvate kinase deficiency, Mol Ther. 24:1187-1198.
Gilsanz, F. et al. (1993). Fetal anaemia due to pyruvate kinase deficiency, Arch Dis Child 69:523-524.
International Search Report dated Sep. 8, 2017, for PCT Application No. PCT/US2017/028695, filed on Apr. 20, 2017, 4 pages.
Matrai, J. et al. (2010). Preclinical and clinical progress in hemophilia gene therapy, Curr Opin Hematol. 17:387-392.
Meza, N.W. et al. (2009). Rescue of pyruvate kinase deficiency in mice by gene therapy using the human isoenzyme, Mol Ther. 17:2000-2009.
Montini, E. et al. (2006). Hematopoietic stem cell gene transfer in a tumor-prone mouse model uncovers low genotoxicity of lentiviral vector integration, Nat Biotechnol. 24:687-696.
Morris, J.C. et al. (2004). Induction of cytotoxic T-lymphocyte response to enhanced green and yellow fluorescent proteins after myeloablative conditioning, Blood 103:492-499.
Schambach, A. et al. (2006). Overcoming promoter competition in packaging cells improves production of self-inactivating retroviral vectors, Gene Ther. 13:1524-153.
Schambach, A. et al. (2007). Improving transcriptional termination of self-inactivating Gamma-retroviral and lentiviral vectors, Mol Ther. 15:1167-1173.
Stripecke, R. et al. (1999). Immune response to green fluorescent protein: Implications for gene therapy, Gene Ther. 6:1305-1312.
Tani, K. et al. (1994). Retrovirus-mediated gene transfer of human pyruvate kinase (PK) cDNA into murine hematopoietic cells: Implications for gene therapy of human PK deficiency, Blood 83:2305-2310.
Tanphaichitr, V.S. et al. (2000). Successful bone marrow transplantation in a child with red blood cell pyruvate kinase deficiency, Bone Marrow Transplant 26:689-690.
Trobridge et al. (2013). Stem Cell Selection In Vivo Using Foamy Vectors Cures Canine Pyruvate Kinase Deficiency PLoS One (Sep. 13, 2013) vol. 7, No. 9, manuscript e45173.
Written Opinion of the International Searching Authority dated Sep. 8, 2017, for PCT Application No. PCT/US2017/028695, filed on Apr. 20, 2017, 5 pages.
Zanella, A. et al. (2005). Red cell pyruvate kinase deficiency: Molecular and clinical aspects, Br J Haematol. 130:11-25.
Zanella, A. et al. (2007). Pyruvate kinase deficiency: The genotype-phenotype association, Blood Rev. 21:217-231.
Zanella, A. et al. (2007). Pyruvate kinase deficiency, Haematologica 92:721-723.
Zanta-Boussif, M.A. et al. (2009). Validation of a mutated PRE sequence allowing high and sustained transgene expression while abrogating WHV-X protein synthesis: Application to the gene therapy of WAS, *Gene Ther.* 16:605-619.
Zaucha, J.M. et al. (2001). Effects of extending the duration of postgrafting immunosuppression and substituting granulocyte-colony-stimulating factor-mobilized peripheral blood mononuclear cells for marrow in allogeneic engraftment in a nonmyeloablative canine transplantation model, Biol Blood Marrow Transplant, 7:513-516.

(56) References Cited

OTHER PUBLICATIONS

Zennou, V. et al. (2000). HIV-1 genome nuclear import is mediated by a central DNA flap, Cell 101:173-185.
Zychlinski, D et al. (2008). Physiological promoters reduce the genetoxic risk of integrating gene vectors, Mol Ther. 16:718-725.
Extended European Search Report dated Oct. 25, 2021, for EP Application No. 18 869 3 037.4, filed Oct. 16, 2018, 8 pages.
Garcia-Gomez, M. et al. (2016), "Safe and Efficient Gene Therapy for Pyruvate Kinase Deficiency," Supplementary Material, 2016, pp. 1-25.
Garcia-Gomez, M. et al. (2013). "Preclinical Studies for the gene therapy treatment of pyruvate kinase deficiency," Tesis Doctoral. Universidad Complutense de Madrid, 2013, pp. 1-271.
Sun Zhaolin, (2014). "Clinical and Testing of Kidney Markers," Editor-in-chief Sun Zhaolin, ZhaYan, Huangshan, Beijing, China, People's Military Medical Publishing House, p. 374 (English Translation of Abstract Provided).

\* cited by examiner

|  |  |  | Primary recipients | | | | Secondary Recipients | | | |
|---|---|---|---|---|---|---|---|---|---|---|
| Non Redundant IS | | | 99 | 168 | 97 | 19 | 113 | 35 | 32 | 27 |
| Total Sequence Reads | | | 14192 | 340586 | 314455 | 69343 | 206932 | 152162 | 200987 | 180905 |
| Chr | Integration Locus | RefGene | coRPK1.1 | coRPK1.2 | coRPK1.3 | coRPK1.4 | coRPK2.1 | coRPK2.2 | coRPK2.3 | coRPK2.4 |
| 16 | 52114775 | Cblb |  |  | 8,87 |  | 5,29 | 12,35 | 0,02 |  |
| 18 | 35737739 | Matr3 |  |  | 4,58 |  | 4,79 | 15,84 | 14,36 | 17,41 |
| 9 | 59671229 | Myo9a |  |  | 2,39 |  | 2,69 | 3,05 | 0,52 | 0,74 |
| 8 | 23308857 | Vps36 |  |  | 6,41 |  | 9,34 | 21,52 |  | 4,97 |
| 1 | 41860552 | 4930448I06Rik |  |  | 1,77 |  | 1,68 | 13,02 | 8,18 |  |
| 10 | 37953519 | Rfpl4b |  |  | 1,39 | 6,17 |  | 1,03 | 0,39 |  |
| 1 | 125478355 | Dpp10 |  |  | 0,91 |  | 1,10 | 3,18 |  | 1,63 |
| 2 | 148695277 | Cst3 |  |  | 0,44 |  | 3,02 |  | 0,35 | 2,64 |
| 6 | 80828813 | Lrrtm4 |  |  | 0,16 |  | 0,29 | 0,44 |  | 0,22 |
| 7 | 4446040 | Ppp1r12c |  |  | 0,01 |  | 0,01 | 0,01 | 0,02 |  |
| 10 | 7744574 | Tab2 |  |  | 3,27 |  | 9,12 |  |  | 4,07 |
| 5 | 18735403 | Magi2 | 33,36 | 0,81 |  |  | 0,01 |  |  |  |
| 18 | 57525115 | Prrc1 | 17,40 |  |  |  | 6,26 | 2,22 |  |  |
| X | 105969090 | Brwd3 | 1,95 | 0,71 |  |  | 0,11 |  |  |  |
| 3 | 148528413 | Lphn2 | 1,76 | 0,45 |  |  |  |  |  | 0,24 |
| 5 | 13643926 | Sema3a | 1,58 |  |  |  | 0,05 | 0,53 |  |  |
| 4 | 24449640 | Mms22l | 0,96 | 0,35 |  |  | 0,11 |  |  |  |
| 1 | 107487037 | Pign |  |  |  | 12,04 |  |  | 0,35 |  |
| 19 | 27467465 | D19Bwg1357e |  |  |  | 9,75 |  | 0,63 |  |  |
| 13 | 73458709 | Ndufs6 |  |  |  | 9,58 |  |  | 0,00 |  |
| 14 | 86078480 | 4930529K09Rik |  |  |  | 0,00 |  |  |  | 0,00 |
| 12 | 72161794 | Arid4a |  |  | 9,44 |  |  |  | 0,00 |  |
| 1 | 109398282 | Serpinb2 |  |  | 5,61 |  |  |  |  | 0,00 |
| 17 | 18006611 | Fpr1 |  |  | 1,35 |  |  |  | 0,00 |  |
| 2 | 38132209 | Dennd1a |  |  | 1,28 |  |  | 0,00 |  |  |
| 16 | 81433433 | Ncam2 |  |  | 0,04 |  |  |  |  | 0,00 |
| 6 | 56736516 | Kbtbd2 |  | 6,40 |  |  |  |  | 0,03 |  |
| 7 | 79224238 | Mctp2 |  | 3,31 |  |  |  |  |  | 22,26 |
| 16 | 58006735 | Col8a1 |  | 3,16 |  |  |  |  | 0,00 |  |
| 4 | 85596276 | Adamtsl1 |  | 2,37 |  |  | 0,02 |  |  |  |
| 7 | 111583985 | Trim30a |  | 2,29 |  |  | 0,01 |  |  |  |
| 16 | 33948595 | Itgb5 |  | 1,74 |  |  | 0,01 |  |  |  |
| 13 | 7150736 | Pfkp |  | 1,11 |  |  | 0,01 |  |  |  |
| 6 | 9899432 | Nxph1 |  | 0,82 |  |  | 0,00 |  |  |  |
| 4 | 66828139 | Tlr4 |  | 0,78 |  |  | 0,01 |  |  |  |
| 19 | 34647666 | Ifit2 |  | 0,70 |  |  | 0,08 |  |  |  |
| 2 | 174443138 | Zfp831 |  | 0,54 |  |  |  |  |  | 3,79 |
| 19 | 23412889 | Mamdc2 |  | 0,41 |  |  | 0,00 |  |  |  |
| 14 | 96290784 | 4921530L21Rik |  | 0,33 |  |  | 0,00 |  |  |  |
| X | 82997642 | Gyk |  | 0,30 |  |  | 0,00 |  |  |  |
| 6 | 43431106 | 9430018G01Rik |  | 0,16 |  |  | 0,00 |  |  |  |
| 11 | 98079745 | Cdk12 |  | 0,10 |  |  | 0,00 |  |  |  |
| 6 | 13808636 | 2610001J05Rik |  | 0,03 |  |  | 0,00 |  |  |  |
| X | 83019292 | Gyk | 3,15 |  |  |  |  | 0,00 |  |  |
| 4 | 144607235 | Vps13d | 1,06 |  |  |  |  |  |  | 0,11 |
| 10 | 53745139 | Man1a | 0,07 |  |  |  |  |  |  | 0,00 |
| 2 | 104684227 | Prrg4 | 0,04 |  |  |  |  | 0,00 |  |  |

*FIG. 18*

METHODS OF TREATING OR PREVENTING PYRUVATE KINASE DEFICIENCY

CROSS-REFERENCE TO RELATED APPLICATIONS

This application is a National Stage of International Application No. PCT/US2017/028695, filed on Apr. 20, 2017, which claims priority to U.S. Provisional Application No. 62/325,397, filed on Apr. 20, 2016, which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ROPA_001_01US_ST25.txt. The text file is 6,288 bytes, created on Apr. 2, 2019, and is submitted electronically via EFS-Web.

FIELD OF THE INVENTION

This invention pertains to gene therapy of Pyruvate Kinase Deficiency.

BACKGROUND OF THE INVENTION

Pyruvate Kinase Deficiency (PKD) is a monogenic metabolic disease caused by mutations in the PKLR gene that leads to hemolytic anemia of variable symptomatology and that can be fatal during the neonatal period. PKD recessive inheritance trait and its curative treatment by allogeneic bone marrow transplantation provide an ideal scenario for developing gene therapy approaches.

Among many other hereditary enzymatic defects affecting the erythrocytes, Pyruvate Kinase deficiency (PKD) is the most frequent one causing chronic nonspherocytic hemolytic anemia (CNSHA) (Zanella et al. 2007). Onset and severity of PKD are very variable and range from mild to severe neonatal anemia, becoming fatal during the childhood in the most severe cases (Pissard et al 2006). Growth retardation, *Hydrops fetalis* and death during the neonatal period have also been reported with low frequency (Gilsanz et al. 1993). PKD prevalence has been estimated at 1:20,000 in the general Caucasian population (Beutler et al 2000) and, so far, more than 195 different mutations in the PKLR gene have been identified (lovd.nl/pklr). Allogeneic bone marrow transplantation (BMT) has been successfully used to cure severe PKD patients (Tanphaichitr et al 2000), but the low availability of histocompatible donors and the serious complications associated with the BMT of these patients (i.e. graft versus host disease, opportunistic infections, etc.) make periodic blood transfusions and splenectomy the main therapeutic options for most of the severe forms of PKD (Zanella et al 2005), dramatically increasing patient morbidity and mortality (Hilgard et al 2005). The limited efficacy and side effects of the therapeutic options for severe PKD patients and its recessive inheritance trait make PKD a suitable disease to be treated by gene therapy.

PKD is caused by defects in the Pyruvate Kinase (PK) enzyme (Zanella 2005) that catalyses the last ATP-generating reaction of the glycolysis pathway in all cells. In mature erythrocytes PK becomes essential as RBCs only express the R-type specific isoform (RPK) (Kanno et al 1992) due to the regulation of the erythroid specific alternative promoter of the PKLR locus (Noguchi et al 1987). Thus, any loss of RPK activity impairs RBC metabolism and lifespan (Zanella 2005), leading to CNSHA.

A promising approach to treating and preventing genetic and other diseases and disorders is delivery of therapeutic agents with a gene therapy vector. Currently, viral vectors show the greatest efficiency in gene transfer, and for correction of genetic diseases such that persistent gene expression is required, herpesvirus, retrovirus, lentivirus, adenovirus, or AAV based vectors are desirable due to the integrating nature of the viral life cycle.

Gene therapy for monogenic diseases, particularly those affecting the hematopoietic system, has provided convincing evidence that genetic correction of autologous hematopoietic stem cells (HSCs) is an alternative therapeutic option to allogeneic HSCT, avoiding its major complications (Cartier et al 2009; Cavazzana-Calvo et al 2010; Cartier et al 2012; Aiuti et al 2013; Biffi et al 2013). Genetic correction for diseases affecting the erythrocyte such as β-thalassemia and sickle cell disease, have been addressed in animal models (Pestina et al 20091 Breda et al 2012) and also in humans (Cavazzana-Calvo et al 2010). However, gene therapy approaches for inherited erythroid metabolic deficiencies such as PKD are still limited. The feasibility of HSC gene therapy for PKD has been demonstrated both in mouse (Tani et al 1994; Meza et al 2009) and in dog RPK deficient experimental models (Trobridge et al 2012) showing that donor chimerism and transduction levels are key points to reach an efficient correction of the hemolytic phenotype (Richard et al 2004) given the lack of selective advantage of donor gene-corrected HSCs. Previous work with a PKD mouse model demonstrated that retrovirally-derived human RPK expression was capable of fully correcting PKD phenotype when over 25% genetically corrected cells were transplanted (Meza et al 2009). A similar therapeutic threshold of corrected cells was recently reported in one PKD Basenji dog infused with in vivo expanded and foamy vector-corrected HSCs (Trobridge et al 2012).

A number of challenges remain with regard to designing polynucleotide cassettes and expression vectors for use in gene therapy. One significant challenge is obtaining sufficient expression of the transgene in target cells. A longstanding unmet need in the art has been sufficiently robust expression of transgenes following gene transfer. In some cases, more efficient expression is required for the efficacy of certain vectors, for example plasmid DNA vectors. In other cases, more efficient gene expression cassettes are desirable to allow for a lower therapeutic dose that has a more favorable safety profile or a less invasive route of administration.

High levels of transgene expression can be achieved when gammaretroviral (gamma-RV) vectors are used due to the fact that the therapeutic transgene expression is regulated by their LTR sequences. However, the first clinical trials based on this type of vector raised safety concerns, as several patients developed unexpected leukemias (Hacein-Bey-Abina et al 2008) The strong promoter activity of LTR sequences could affect the regulation of surrounding genes, either by activation of proto-oncogene promoters or by inhibition of tumour suppressor genes, leading to insertional mutagenesis (Ott et al 2006; Howe et al 2008; Stein et al 2010; Braun et al 2014). These findings highlighted the need to use safer and more efficient vectors than gamma retroviral vectors for the PKD gene therapy.

SUMMARY OF THE INVENTION

In one embodiment, the present invention provides an expression cassette comprising a polynucleotide sequence comprising: a) a promoter sequence; b) a sequence encoding a gene product; and c) an ribonucleic acid (RNA) export signal, wherein the promoter sequence is operably linked to the sequence encoding the pyruvate kinase polypeptide, and optionally where a)-c) are present in the expression cassette in 5' to 3' order. In certain embodiments, the promoter is a phosphoglycerate kinase (PGK) promoter. In some embodiments, the gene product is a therapeutic gene product. In some embodiments, the therapeutic gene product is a pyruvate kinase (PK) polypeptide, optionally a pyruvate kinase, liver and red blood cell (PKLR) polypeptide. In certain embodiments, the sequence encoding the gene product is codon-optimized. In particular embodiments, the RNA export signal is a mutated post-transcriptional regulatory element of the woodchuck hepatitis virus (Wpre). In certain embodiments, the mutated Wpre is a chimeric Wpre comprising a sequence having at least 80% identity to SEQ ID NO:1. In some embodiments, the expression cassette further comprising one or more enhancer sequences. In some embodiments, the expression cassette further comprises a polypurine tract (PPT) or polyadenylation (polyA) signal sequence. In some embodiments, the expression cassette further comprises one or more of the following sequences: i) a packing signal sequence; ii) a truncated Gag sequence; iii) a Rev responsive element (RRE); iv) a central polypurine tract (cPPT); v) a central terminal sequence (CTS); and vi) an upstream sequence element (USE), optionally from simian virus 40 (SV40-USE). In some embodiments, the expression cassette further comprises 5' and 3' long terminal repeat sequences.

In a related embodiment, the present invention provides a recombinant gene delivery vector comprising an expression cassette disclosed herein. In certain embodiments, the recombinant gene delivery vector is a virus or viral vector. In certain embodiments, the virus or viral vector is a lentivirus (LV).

In another related embodiment, the present invention provides a cell comprising an expression cassette or gene delivery vector disclosed herein. In some embodiments, the cell is a blood cell. In some embodiments, the cell is an erythroid cell. In some embodiments, the cell is a bone marrow cell, e.g., a lineage depleted bone marrow cell. In some embodiments, the cell is a hematopoietic stem cell. In some embodiments, the cell is a CD34+ hematopoietic stem cell. In some embodiments, the cell is a committed hematopoietic erythroid progenitor cell.

In yet another related embodiment, the present invention provides a pharmaceutical composition comprising a pharmaceutically acceptable excipient and recombinant gene delivery vector or cell disclosed herein.

In another embodiment, the present invention provides a method of treating or preventing a disease or disorder in a subject in need thereof, comprising providing to the subject an expression cassette, gene delivery vector, or pharmaceutical composition disclosed herein. In one embodiment, the disease or disorder is a Pyruvate Kinase Deficiency (PKD) and the gene product is a pyruvate kinase (PK) polypeptide, optionally a pyruvate kinase, liver and red blood cell (PKLR) polypeptide. In certain embodiments, the pharmaceutical composition comprises the recombinant gene delivery vector. In other embodiments, the pharmaceutical composition comprises the cell. In one embodiment, the cell is autologous to the subject. In another embodiment, the cell is allogeneic to the subject.

In a related embodiment, the present invention provides a method for expressing a transgene in erythroid cells, comprising contacting one or more erythroid cells with an effective amount of a recombinant viral vector, wherein the vector comprises a human phosphoglycerate kinase promoter, a codon optimized version of a human pyruvate kinase, liver and red blood cell (PKLR) cDNA transgene, and a mutated post-transcriptional regulatory element of the woodchuck hepatitis virus, wherein following said contacting, PKLR is expressed at detectable levels in the one or more erythroid cells.

BRIEF DESCRIPTION OF THE DRAWINGS

The novel features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3a RBCs and FIG. 3b are reticulocyte levels in healthy (black bar, n=5) and PKD anemic mice (gray bar, n=6), and PKD anemic mice that were tranplanted with the EGFP (white bar, n=9) or coRPK transduced cells (scratched bar, n=17). Data are represented as the average±SEM and were analyzed by non-parametric Kruskal-Wallis test. FIG. 3c shows the flow cytometry strategy used to detect the biotin labelled RBCs throughout the time and FIG. 3d RBC survival kinetics in healthy (black line, n=2), anemic (gray line, n=2) and genetically corrected mice (discontinuous line, n=4). Data are represented as the average±SEM and were analyzed by two-way ANOVA test. Healthy, non-transplanted control mice; PKD, non-transplanted PKD mice; coRPK, PKD mice expressing the therapeutic transgene.

FIG. 4a is a diagram of the flow cytometry strategy used to identify the different hematopoietic lineages by labeling with CD3-PE, B220-PE, B220-PECy5, Grl-Biotin and Mac1-Biotin antibodies plus SAV-PE-Cy5. FIG. 4b depicts representative dot-plots and FIG. 4c depicts percentages of each lineage in PB at 140 days after transplant. Bars represent the average percentage±SEM of healthy (n=2, black bar) and PKD mouse (n=2, grey bar) controls and secondary transplanted mice expressing the coRPK therapeutic transgene (n=4, scratched bar).

FIG. 5a shows Brilliant Cresyl blue staining of blood smears from non-transplanted mice and secondary recipients to identify reticulocyte population (in blue). FIG. 5b is Flow cytometry analysis of reticulocyte levels in peripheral blood. FIG. 5c represents RBC percentage and FIG. 5d reticulocyte percentage in secondary transplanted mice expressing the coRPK transgene (scratched bar, n=4), in healthy mice (black bar, n=3) and in anemic control mice (grey bar, n=3). Data are represented the average±SEM and were analyzed by non-parametric two-tailed Mann-Whitney test.

FIG. 6a shows vector copy number per cell in BM CFUs from individual transplanted mice at 120 to 170 days after transplant. Transduction and chimerism percentages are also shown. FIG. 6b shows provirus copy number in cells from different hematopoietic compartments. Columns represent the average±SEM of the different groups of transplanted mice. FIG. 6c shows the kinetics of proviral integrations in BM cells from individual transplanted EGFP-expressing mice (grey lines) and mice carrying the coRPK transgene (black lines).

FIG. 7a shows percentages of the different erythroid subpopulation in bone marrow and spleen at 140 days after transplant. FIG. 7b depicts representative dot plots of the flow cytometry strategy used. The expression intensity of the CD71 and Ter119 markers allows for identifying four erythroid subpopulations. population I: early proerythroblasts (Ter119$^{med}$ CD71$^{high}$), population II: basophilic erythroblasts (Ter119$^{high}$ CD71$^{high}$), population III: late basophilic and polychromatophilic erythroblasts (Ter119$^{high}$ CD71$^{med}$) and population IV: orthochromatophilic erythroblasts, reticulocytes and mature erythroid cells (Ter119$^{high}$ CD71$^{low}$). FIG. 7c shows plasma Epo levels measured by ELISA in non-transplanted and transplanted mice. Dots represent values of individual mice. Lines represent average±SEM and were analyzed by non-parametric Kruskal-Wallis test. Healthy, non-transplanted control mice; PKD, non-transplanted PKD mice; EGFP, PKD mice expressing the EGFP transgene; coRPK, PKD mice expressing the therapeutic transgene.

FIG. 9a are pictures of representative spleens and FIG. 9b shows ratio of spleen weight to total body weight from primary and secondary transplanted PKD mice. Dots represent values of individual mice. Lines represent average±SEM per group. Data were analyzed by non-parametric Kruskal-Wallis test. FIG. 9c shows the histological study of spleen and liver from primary transplanted PKD mice. First and second column show the representative histology sections of spleen and liver stained with hematoxylin-eosin and photographed using a 4× and 10× objective, respectively, in a light microscope. Arrows point to erythroid cell clusters indicative of extramedullary erythropoiesis. Third column shows Prussian blue staining (Fe) of liver sections to detect iron deposits indicated by arrowheads. Photographs were taken using a 20× objective. Group legends as in FIG. 7. 2$^{nd}$ coRPK, secondary recipients.

FIG. 10a shows the complete RBC heat map obtained by untargeted profiling, where higher and lower metabolite levels are represented in red and blue respectively. Metabolites listed have at least one comparison that is significant using the following criteria: absolute fold change>1.5; minimal signal>2000; Adjusted p-value<0.01. Black boxes highlight cluster of metabolite changes with distinct profile among the groups. FIGS. 10b, 10c, and 10d depict ATP, ADP and pyruvate levels in RBCs, respectively, measured by untargeted profiling by comparison to PKD mice at 140 days after transplant. Assay 1: Healthy mice (black bars) n=1, PKD (grey bars) n=1, hPGK-EGFP (white bars) n=2, hPGK-coRPK (scratched bars) n=3. Assay 2: Healthy mice n=2, PKD n=2, hPGK-EGFP n=6, hPGK-coRPK n=10. FIGS. 10e, 10f, and 10g depict RBC targeted metabolic profiling of a selected number of metabolites involved in the glycolytic pathway (PEP, 3-phosphoglyceric acid and D-lactic acid, respectively) at 280 days post-transplantation. Dots represent values of individual mice. Lines represent average±SEM and were analyzed by non-parametric Kruskal-Wallis test. Assay 2: Healthy mice n=7, PKD n=5, hPGK-EGFP n=3, hPGK-coRPK n=5.

FIG. 12a represents the principal component analysis of untargeted metabolite profile in RBCs (red dots; left and center) and WBCs (blue dots; cluster on right) in control and transplanted mice. FIGS. 12b, 12c, and 12d depict ATP, ADP and pyruvate levels, respectively, in WBCs by comparison to PKD mice. Assay 1: healthy mice (black bars) n=1, PKD (grey bars) n=1, hPGK-EGFP (white bars) n=2, hPGK-coRPK (scratched bars) n=3. Assay 2: healthy mice n=2, PKD n=2, hPGK-EGFP n=6, hPGK-coRPK n=10. Data represent the average±SEM per group and were analyzed by non-parametric Kruskal-Wallis test.

FIG. 16a depicts Integration site (IS) frequency distribution around Transcription Start Site (TSS) of the nearest RefSeq gene, spanning 500 Kb upstream and downstream the TSS. Numbers on the top are the number of IS detected for all samples and time-points. FIG. 16b depicts chromosomal distribution of LV integration sites in transplanted mice expressing the EGFP transgene (black bars) or the coRPK therapeutic transgene (grey bars), showing no skewing towards any particular chromosome.

FIG. 18 presents the tracked shared integrations between primary and secondary recipient mice carrying the therapeutic PGK-coRPK LV vector. Integrations detected in either mouse in any organ and at any time are pooled. Secondary recipients received the pooled BM from transplanted mice coRPK11 to 14. The rest of the IS detected were detected or in the primary or in the secondary recipients. Numbers in the boxes show the representativeness in percentage of the corresponding integration in the referred mouse. In addition to >5% filter applied on integration analysis, all integration with a sequence count<3 were eliminated.

FIG. 22a depicts the ectopic expression of the PGK-coRPK LV medicinal product will rescue the wild-type phenotype of PKD erythrocytes, otherwise unable to generate a functional RPK protein to produce sufficient energy to carry out their functions. FIG. 22b shows the gene therapy strategy for PKD patients based on the ex vivo transduction of RPK deficient CD34$^+$ hematopoietic progenitors with the medicinal product and subsequent transplantation into the patient. The developed medicinal product carrying the therapeutic human PKLR gene cDNA will be integrated in the patient CD34$^+$ cell genome upon ex vivo transduction. These genetically corrected cells will be then infused back into the patient, where they will produce RBCs expressing the therapeutic transgene, and therefore, producing functional RPK proteins that will correct the PKD pathological phenotype. Figure modified from the Boston Children's Hospital blog.

DETAILED DESCRIPTION OF THE INVENTION

Definitions

Figure 1:
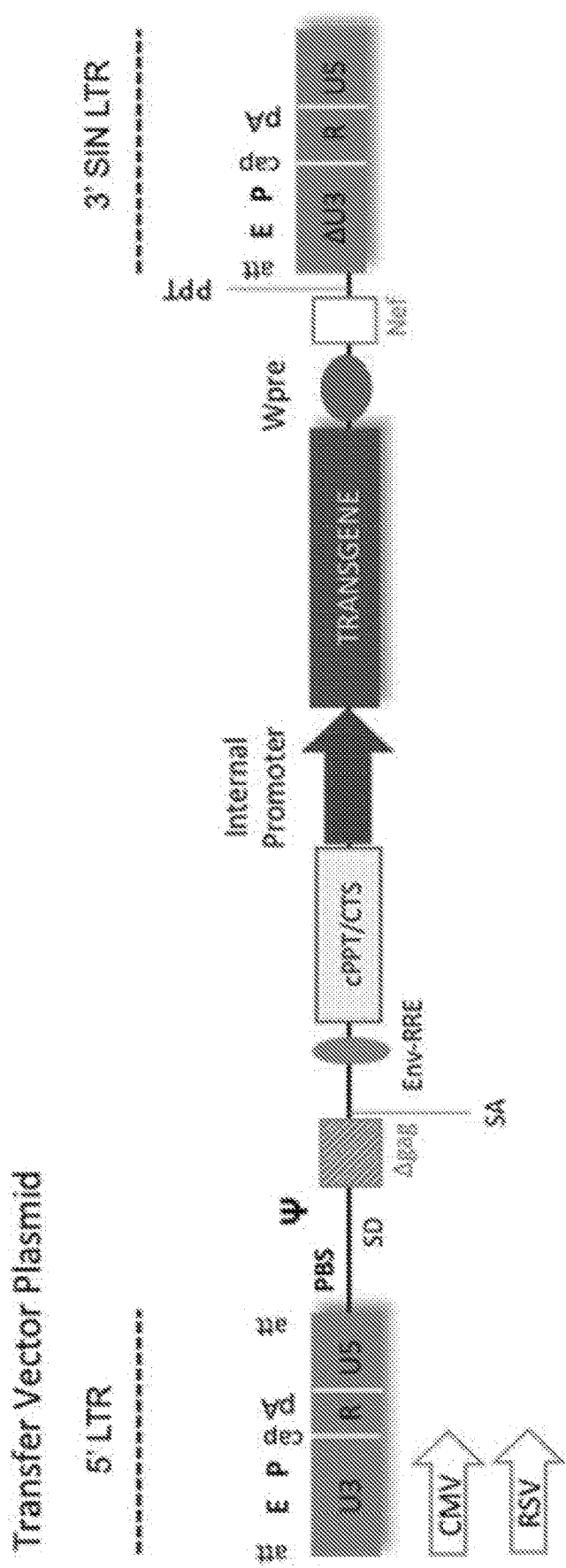
FIG. 1 depicts a scheme reflecting the position of the different described elements present in the backbone of the lentiviral vector.

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes, and other gene delivery vehicles.

The term "LV" is an abbreviation for lentivirus, and may be used to refer to the virus itself or derivatives thereof. The term covers all subtypes and both naturally occurring and recombinant forms, except where required otherwise.

As used herein, the term "gene" or "coding sequence" refers to a nucleotide sequence in vitro or in vivo that encodes a gene product. In some instances, the gene consists or consists essentially of coding sequence, that is, sequence that encodes the gene product. In other instances, the gene comprises additional, non-coding, sequence. For example, the gene may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, a "therapeutic gene" refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

As used herein, a transgene is a gene that is delivered to a cell by a vector.

As used herein, the term "gene product" refers to the desired expression product of a polynucleotide sequence such as a polypeptide, peptide, protein or interfering RNA including short interfering RNA (siRNA), miRNA or small hairpin RNA (shRNA).

As used herein, the terms "polypeptide," "peptide," and "protein" refer to polymers of amino acids of any length. The terms also encompass an amino acid polymer that has been modified; for example, disulfide bond formation, glycosylation, lipidation, phosphorylation, or conjugation with a labeling component.

By "comprising" it is meant that the recited elements are required in, for example, the composition, method, kit, etc., but other elements may be included to form the, for example, composition, method, kit etc. within the scope of the claim. For example, an expression cassette "comprising" a gene encoding a therapeutic polypeptide operably linked to a promoter is an expression cassette that may include other elements in addition to the gene and promoter, e.g. polyadenylation sequence, enhancer elements, other genes, linker domains, etc.

By "consisting essentially of", it is meant a limitation of the scope of the, for example, composition, method, kit, etc., described to the specified materials or steps that do not materially affect the basic and novel characteristic(s) of the, for example, composition, method, kit, etc. For example, an expression cassette "consisting essentially of" a gene encoding a therapeutic polypeptide operably linked to a promoter and a polyadenylation sequence may include additional sequences, e.g. linker sequences, so long as they do not materially affect the transcription or translation of the gene. As another example, a variant, or mutant, polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of", it is meant the exclusion from the composition, method, or kit of any element, step, or ingredient not specified in the claim. For example, an expression cassette "consisting of" a gene encoding a therapeutic polypeptide operably linked to a promoter, and a post-transcriptional regulatory element consists only of the promoter, polynucleotide sequence encoding the therapeutic polypeptide, and post-transcriptional regulatory element. As another example, a polypeptide "consisting of" a recited sequence contains only the recited sequence.

An "expression vector" as used herein encompasses a vector, e.g. plasmid, minicircle, viral vector, liposome, and the like as discussed above or as known in the art, comprising a polynucleotide which encodes a gene product of interest, and is used for effecting the expression of a gene product in an intended target cell. An expression vector also comprises control elements operatively linked to the encoding region to facilitate expression of the gene product in the target. The combination of control elements, e.g. promoters, enhancers, UTRs, miRNA targeting sequences, etc., and a gene or genes to which they are operably linked for expression is sometimes referred to as an "expression cassette." Many such control elements are known and available in the art or can be readily constructed from components that are available in the art.

A "promoter" as used herein encompasses a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, tissue-specific, or species specific. Promoters may be "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence. Enhancer sequences influence promoter-dependent gene expression and may be located in the 5' or 3' regions of the native gene.

An "enhancer" as used herein encompasses a cis-acting element that stimulates or inhibits transcription of adjacent genes. An enhancer that inhibits transcription also is termed a "silencer". Enhancers can function (i.e., can be associated with a coding sequence) in either orientation, over distances of up to several kilobase pairs (kb) from the coding sequence and from a position downstream of a transcribed region.

A "termination signal sequence" as used herein encompasses any genetic element that causes RNA polymerase to terminate transcription, such as for example a polyadenylation signal sequence.

As used herein, the terms "operatively linked" or "operably linked" refers to a juxtaposition of genetic elements, e.g. promoter, enhancer, termination signal sequence, polyadenylation sequence, etc., wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

As used herein, the term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. As another example, a promoter removed from its native coding sequence and operatively linked to a coding sequence with which it is not naturally found linked is a heterologous promoter. Thus, for example, an LV vector that includes a heterologous nucleic acid encoding a heterologous gene product is an LV vector that includes a nucleic acid not normally included in a naturally-occurring, wild-type LV, and the encoded heterologous gene product is a gene product not normally encoded by a naturally-occurring, wild-type LV.

The term "endogenous" as used herein with reference to a nucleotide molecule or gene product refers to a nucleic acid sequence, e.g. gene or genetic element, or gene product, e.g. RNA, protein, that is naturally occurring in or associated with a host virus or cell.

The term "native" as used herein refers to a nucleotide sequence, e.g. gene, or gene product, e.g. RNA, protein, that is present in a wildtype virus or cell.

The term "variant" as used herein refers to a mutant of a reference polynucleotide or polypeptide sequence, for example a native polynucleotide or polypeptide sequence, i.e. having less than 100% sequence identity with the reference polynucleotide or polypeptide sequence. Put another way, a variant comprises at least one amino acid difference (e.g., amino acid substitution, amino acid insertion, amino acid deletion) relative to a reference polynucleotide sequence, e.g. a native polynucleotide or polypeptide sequence. For example, a variant may be a polynucleotide having a sequence identity of 70% or more with a full length native polynucleotide sequence, e.g. an identity of 75% or 80% or more, such as 85%, 90%, or 95% or more, for example, 98% or 99% identity with the full length native polynucleotide sequence. As another example, a variant may be a polypeptide having a sequence identity of 70% or more with a full length native polypeptide sequence, e.g. an identity of 75% or 80% or more, such as 85%, 90%, or 95% or more, for example, 98% or 99% identity with the full length native polypeptide sequence. Variants may also include variant fragments of a reference, e.g. native, sequence sharing a sequence identity of 70% or more with a fragment of the reference, e.g. native, sequence, e.g. an identity of 75% or 80% or more, such as 85%, 90%, or 95% or more, for example, 98% or 99% identity with the native sequence.

As used herein, the terms "biological activity" and "biologically active" refer to the activity attributed to a particular biological element in a cell. For example, the "biological activity" of an "immunoglobulin", "antibody" or fragment or variant thereof refers to the ability to bind an antigenic determinant and thereby facilitate immunological function. As another example, the biological activity of a polypeptide or functional fragment or variant thereof refers to the ability of the polypeptide or functional fragment or variant thereof to carry out its native functions of, e.g., binding, enzymatic activity, etc. As a third example, the biological activity of a gene regulatory element, e.g. promoter, enhancer, kozak sequence, and the like, refers to the ability of the regulatory element or functional fragment or variant thereof to regulate, i.e. promote, enhance, or activate the translation of, respectively, the expression of the gene to which it is operably linked.

The terms "administering" or "introducing", as used herein, refer to delivery of a vector for recombinant protein expression to a cell, to cells and/or organs of a subject, or to a subject. Such administering or introducing may take place in vivo, in vitro or ex vivo. A vector for expression of a gene product may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" is typically used to refer to bacteria comprising heterologous DNA or cells which express an oncogene and have therefore been converted into a continuous growth mode such as tumor cells. A vector used to "transform" a cell may be a plasmid, virus or other vehicle.

Typically, a cell is referred to as "transduced", "infected"; "transfected" or "transformed" dependent on the means used for administration, introduction or insertion of heterologous DNA (i.e., the vector) into the cell. The terms "transduced", "transfected" and "transformed" may be used interchangeably herein regardless of the method of introduction of heterologous DNA.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

The terms "treatment", "treating" and the like are used herein to generally mean obtaining a desired pharmacologic and/or physiologic effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Unless otherwise indicated, all terms used herein have the same meaning as they would to one skilled in the art and the practice of the present invention will employ conventional techniques of microbiology and recombinant DNA technology, which are within the knowledge of those of skill of the art.

The practice of the present invention employs, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

In certain embodiments, the present disclosure provides polynucleotides, polynucleotide cassettes and expression vectors for the expression of a gene in cells. Also provided are pharmaceutical compositions and methods for the use of any of the compositions in promoting the expression of a gene in cells, for example, in an individual, e.g. for the treatment or prophylaxis of a disorder. These and other objects, advantages, and features of the invention will become apparent to those persons skilled in the art upon reading the details of the compositions and methods as more fully described below.

The present invention relates generally to the fields of molecular biology and virology, and in particular, to genetic expression cassettes, and vectors comprising them useful for the delivery of nucleic acid segments encoding selected therapeutic constructs (including for example, peptides, polypeptides, ribozymes, and catalytic RNA molecules), to selected cells and tissues of vertebrate animals. In particular, these genetic constructs are useful in the development of gene therapy vectors, including for example, lentiviral vectors, for the treatment of mammalian, and in particular, human, diseases, disorders, and dysfunctions.

The disclosed compositions may be utilized in a variety of investigative, diagnostic and therapeutic regimens, including the prevention and treatment of a variety of human diseases. The various compositions and methods of the invention are described below.

Although particular compositions and methods are exemplified herein, it is understood that any of a number of alternative compositions and methods are applicable and suitable for use in practicing the invention. It will also be understood that an evaluation of the expression constructs and methods of the invention may be carried out using procedures standard in the art.

In certain embodiments, methods and compositions are provided for preparation of gene therapy vector compositions, e.g., viral vectors, comprising these genetic expression cassettes for use in the preparation of medicaments useful in central and targeted gene therapy of diseases, disorders, and dysfunctions in an animal, and in humans in particular.

In some embodiments, the present invention provides for gene therapy for PKD based on a lentiviral vector harbouring the hPGK eukaryotic promoter that drives the expression of the PKLR cDNA. This therapeutic vector may be used to transduce mouse PKD hematopoietic stem cells (HSCs) and subsequently transplanted into myeloablated PKD mice. Ectopic RPK expression normalizes the erythroid compartment correcting the hematological phenotype and reverting organ pathology. Metabolomic studies demonstrate functional correction of the glycolytic pathway in RBCs derived from genetically corrected PKD HSCs, with no metabolic disturbances in leukocytes. The analysis of the lentiviral insertion sites in the genome of transplanted hematopoietic cells demonstrates no evidence of genotoxicity in any of the transplanted animals. Overall, the results underscore the therapeutic potential of the hPGK-coRPK lentiviral vector and provide high expectations towards the gene therapy of PKD and other erythroid metabolic genetic disorders.

In certain embodiments, the present invention provides an RPK lentiviral vector (LV) for the genetic correction of PKD. Genetic modification of murine PKD-HSCs with this vector can efficiently correct the hemolytic phenotype and the RBC metabolite profile in transplanted PKD mice. Remarkably, no evidence of metabolic disturbances in leukocytes and genotoxicity derived from the vector integration are observed, supporting the therapeutic potential of the PGK-coRPK LV vector. Overall, results provide encouraging evidence of the feasibility of gene therapy for PKD with a LV designed for clinical application.

Certain embodiments of the present invention comprise a self-inactivating lentiviral vector expressing a codon-optimized version of human PKLR gene. The expression vector comprises a promoter region, a coding sequence, and a post-transcriptional regulatory element.

Certain embodiments of polynucleotide cassettes of the present invention comprise a promoter region comprising a promoter sequence, or a functional fragment thereof. In one embodiment, the promoter is a human phosphoglycerate kinase (PGK) promoter.

Some embodiments of the present invention comprise polynucleotide cassettes for the enhanced expression of pyruvate kinase. In some embodiments, the polynucleotide cassette comprises a codon-optimized version of the human PKLR cDNA (coRPK) to increase mRNA stability upon transcription. For the optimization, GeneArt® software may be used, increasing the GC content and removing cryptic splice sites in order to avoid transcriptional silencing and therefore increase transgene expression. The coRPK optimized sequence showed 80.4% homology with the human PKLR gene, with no changes in the amino acids sequence of the protein. Alternatively, any optimization method known in the art may be used.

In some embodiments, the polynucleotide cassette comprises an RNA export signal downstream of the second enhancer. The RNA export signal may comprise woodchuck hepatitis virus post-transcriptional element (WPRE) sequence. In some embodiments, a mutated post-transcriptional regulatory element of the woodchuck hepatitis virus (Wpre), lacking any residual open reading frame (Schambach, Bohne et al. 2006) is also included to improve the level of expression and stability of the therapeutic gene.

In some aspects of the invention, gene delivery vectors are provided comprising a polynucleotide cassette of the present invention. In some embodiments, the gene delivery vector is a lentivirus.

In some aspects of the invention, pharmaceutical compositions are provided comprising a polynucleotide cassette of the invention and a pharmaceutical excipient. In some embodiments, the pharmaceutical composition comprises a gene delivery vector of the invention and a pharmaceutical excipient.

In some aspects of the invention, methods are provided for expressing a transgene in mammalian cells. In some embodiments, the method comprises contacting one or more mammalian cells with an effective amount of a polynucleotide cassette of the invention or a gene delivery vector of the invention, wherein the transgene is expressed at detectable levels in the one or more mammalian cells. In some embodiments, the method comprises contacting one or more mammalian cells with an effective amount of a polynucleotide cassette of the invention or a gene delivery vector of the invention, wherein the transgene is expressed at therapeutic levels in the one or more mammalian cells. In some embodiments, the method is in vitro. In other embodiments, the method is in vivo.

In some aspects of the invention, methods are provided for the treatment or prophylaxis of a disease or disorder in a mammal in need of treatment or prophylaxis for a disease or disorder. In some embodiments, the method comprises administering to the mammal an effective amount of a pharmaceutical composition of the invention, wherein the coding sequence encodes a therapeutic gene product.

Compositions

In some aspects of the disclosure, compositions are provided for the expression of a transgene in a eukaryotic cell(s). In some aspects, the eukaryotic cell is a mammalian cell. In some aspects, the mammalian cell is a hematopoietic stem cell. In some embodiments, the cell is a bone marrow cell, e.g., a lineage depleted bone marrow cell. In some aspects, the mammalian cell is a committed hematopoietic erythroid progenitor.

In some embodiments of the disclosure, the composition is a polynucleotide cassette. By a "polynucleotide cassette" is meant a polynucleotide sequence comprising two or more functional polynucleotide sequences, e.g. regulatory elements, translation initiation sequences, coding sequences, and/or termination sequences, etc., typically in operable linkage to one another. Likewise, by a "polynucleotide cassette for the expression of a transgene in a mammalian cell," it is meant a combination of two or more functional polynucleotide sequences, e.g. promoter, enhancer, 5'UTR, translation initiation sequence, coding sequence, and/or termination sequences, etc. that promotes the expression of the transgene in a cell.

For example, in some embodiments, the polynucleotide cassette comprises: human phosphoglycerate kinase (PGK) promoter, a codon-optimized version of the human PKLR cDNA (coRPK), and a mutated post-transcriptional regulatory element of the woodchuck hepatitis virus (Wpre).

In particular embodiments of any of the expression cassettes and gene delivery vectors described herein, the human PKLR promoter comprises or consists of the following sequence, a functional fragment thereof, or a sequence having at least 80%, at least 85%, at least 90%, at least 95%, at least 98%, or at least 99% identity to the following sequence:

(SEQ ID NO: 4)
ATTATGGTAAATCCACTTACTGTCTGCCCTCGTAGCCATCGAGATAAACC

CTACCGGGTAGGGGAGGCGCTTTTCCCAAGGCAGTCTGGAGCATGCGCTT

TAGCAGCCCCGCTGGGCACTTGGCGCTACACAAGTGGCCTCTGGCCTCGC

ACACATTCCACATCCACCGGTAGGCGCCAACCGGCTCCGTTCTTTGGTGG

CCCCTTCGCGCCACCTTCTACTCCTCCCCTAGTCAGGAAGTTCCCCCCCG

CCCGCAGCTCGCGTCGTGCAGGACGTGACAAATGGAAGTAGCACGTCTCA

CTAGTCTCGTGCAGATGGACAGCACCGCTGAGCAATGGAAGCGGGTAGGC

CTTTGGGGCAGCGGCCAATAGCAGCTTTGCTCCTTCGCTTTCTGGGCTCA

GAGGCTGGGAAGGGGTGGGTCCGGGGCGGGCTCAGGGGCGGGCTCAGGG

GCGGGGCGGGCGCCCGAAGGTCCTCCGGAGGCCCGGCATTCTGCACGCTT

CAAAAGCGCACGTCTGCCGCGCTGTTCTCCTCTTCCTCATCTCCGGGCCT

TTCGACCTGCAGCCC.

In particular embodiments of any of the expression cassettes and gene delivery vectors described herein, the human PKLR promoter comprises or consists of the following sequence, a functional fragment thereof, or a sequence having at least 80%, at least 85%, at least 90%, at least 95%, at least 98%, or at least 99% identity to the following sequence:

(SEQ ID NO: 8)
TCCACGGGGTTGGGGTTGCGCCTTTTCCAAGGCAGCCCTGGGTTTGCGCA

GGGACGCGGCTGCTCTGGGCGTGGTTCCGGGAAACGCAGCGGCGCCGACC

CTGGGTCTCGCACATTCTTCACGTCCGTTCGCAGCGTCACCCGGATCTTC

GCCGCTACCCTTGTGGGCCCCCCGGCGACGCTTCCTCGTCCGCCCCTAAG

TCGGGAAGGTTCCTTGCGGTTCGCGGCGTGCCGGACGTGACAAACGGAAG

CCGCACGTCTCACTAGTACCCTCGCAGACGGACAGCGCCAGGGAGCAATG

GCAGCGCGCCGACCGCGATGGGCTGTGGCCAATAGCGGCTGCTCAGCAGG

GGCGCCCGAGAGCAGCGGCCGGGAAGGGGCGGTGCGGGAGGCGGGGTGTG

GGGCGGTAGTGTGGGCCCTGTTCCTGCCCGCGCGGTGTTCCGCATTCTGC

AAGCCTCCGGAGCGCACGTCGGCAGTCGGCTCCCTCGTTGACCGAATCAC

CGACCTCTCTCCCCAG.

In particular embodiments of any of the expression cassettes and gene delivery vectors described herein, the RPE sequence comprises or consists of the following sequence, or a sequence having at least 80%, at least 85%, at least 90%, at least 95%, at least 98%, or at least 99% identity to the following sequence:

(SEQ ID NO: 3)
TCCTTGGGTTCTTGGGAGCAGCAGGAAGCACTATGGGCGCAGCGTCAATG

ACGCTGACGGTACAGGCCAGACAATTATTGTCTGGTATAGTGCAGCAGCA

GAACAATTTGCTGAGGGCTATTGAGGCGCAACAGCATCTGTTGCAACTCA

CAGTCTGGGGCATCAAGCAGCTCCAGGCAAGAATCCTGGCTGTGGAAAGA

TACCT.

In particular embodiments of any of the expression cassettes and gene delivery vectors described herein, the psi sequence is an HIV-1 psi sequence or the psi sequence comprises or consists of the following sequence, or a sequence having at least 80%, at least 85%, at least 90%, at least 95%, at least 98%, or at least 99% identity to the following sequence:

(SEQ ID NO: 5)
TCGACGCAGGACTCGGCTTGCTGAAGCGCGCACGGCAAGAGGCGAGGGGC

GGCGACTGGTGAGTACGCCAAAAATTTTGACTAGCGGAGGCTAGAAGGAG

AGAGATGGGTGCGAGAGCGTCAGTATTAAGCGGGGGAG.

In particular embodiments of any of the expression cassettes and gene delivery vectors described herein, the 5' LTR comprises or consists of the following sequence, or a sequence having at least 80%, at least 85%, at least 90%, at least 95%, at least 98%, or at least 99% identity to the following sequence:

(SEQ ID NO: 6)
TGGAAGGGCTAATTCACTCCCAACGAAGACAAGATCTGCTTTTTGCTTGT

ACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTC

AAGTAGTGTGTGCCCGTCTGTTGTGTGACTCTGGTAACTAGAGATCCCTC

AGACCCTTTTAGTCAGTGTGGAAAATCTCTAGCAGT.

In particular embodiments of any of the expression cassettes and gene delivery vectors described herein, the 3' LTR comprises or consists of the following sequence, or a sequence having at least 80%, at least 85%, at least 90%, at least 95%, at least 98%, or at least 99% identity to the following sequence:

(SEQ ID NO: 7)
TGGAAGGGCTAATTCACTCCCAACGAAGACAAGATCTGCTTTTTGCTTGT

ACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTC

AAGTAGTGTGTGCCCGTCTGTTGTGTGACTCTGGTAACTAGAGATCCCTC

AGACCCTTTTAGTCAGTGTGGAAAATCTCTAGCAG.

In some embodiments, the polynucleotide cassettes of the present disclosure provide for enhanced expression of a transgene in mammalian cells. As demonstrated by the working examples of the present disclosure, the present inventors have discovered a number of polynucleotide elements, i.e. improved elements as compared to those known in the art, which individually and synergistically provide for the enhanced expression of transgenes in mammalian cells. In certain embodiments, the arrangement of the two or more functional polynucleotide sequences within the polynucleotide cassettes of the present disclosure provide for enhanced expression of a transgene in mammalian cells. By "enhanced" it is meant that expression of the transgene is increased, augmented, or stronger, in cells carrying the polynucleotide cassettes of the present disclosure relative to in cells carrying the transgene operably linked to comparable regulatory elements, e.g. as known in the art. Put another way, expression of the transgene is increased, augmented, or stronger, from the polynucleotide cassettes of the present disclosure relative to expression from a polynucleotide cassette not comprising the one or more optimized elements of the present disclosure, i.e. a reference control. In certain embodiment, the enhanced expression is specific for or limited to one or more desired cell types.

For example, expression of the transgene may be enhanced, or augmented, or stronger, in cells comprising a polynucleotide cassette comprising a promoter disclosed herein than in cells that carry the transgene operably linked to a different promoter, e.g. as known in the art. As another example, expression of the transgene may be enhanced, or increased, augmented, or stronger, in cells comprising a polynucleotide cassette comprising an enhancer sequence disclosed herein than in cells that carry the transgene operably linked to a different enhancer sequence.

Promoter and enhancer elements can be tissue specific or stage-specific. For example, a tissue-specific promoter or enhancer preferentially drives expression (or a higher level of expression) in one or more particular cell type. Examples of cell types include but are not limited to: hematopoietic stem cells, long term hematopoietic stem cells, short term hematopoietic stem cells, multipotent progenitors, hematopoietic CD34+ cells and any cluster differentiation subpopulation within the CD34+ population. A stage-specific promoter or enhancer preferentially drives expression (or higher level of expression) during one or more specific stages of the cell cycle or development. These include but are not limited to beta-globin locus control region, spectrin promoter, and an erythroid specific promote.

Without wishing to be bound by theory, enhanced expression of a transgene in cells is believed to be due to a faster build-up of gene product in the cells or a more stable gene product in the cells. Thus, enhanced expression of a transgene by the polynucleotide cassettes of the subject disclosure may be observed in a number of ways. For example, enhanced expression may be observed by detecting the expression of the transgene following contact of the polynucleotide cassette to the cells sooner, e.g. 2 days sooner, 7 days sooner, 2 weeks sooner, 3 weeks sooner, 4 weeks sooner, 8 weeks sooner, 12 weeks sooner or more, than expression would be detected if the transgene were operably linked to comparable regulatory elements, e.g. as known in the art. Enhanced expression may also be observed as an increase in the amount of gene product per cell. For example, there may be a 2-fold increase or more, e.g. a 3-fold increase or more, a 4-fold increase or more, a 5-fold increase or more, or a 10-fold increase or more in the amount of gene product per mammalian cell. Enhanced expression may also be observed as an increase in the number of mammalian cells that express detectable levels of the transgene carried by the polynucleotide cassette. For example, there may be a 2-fold increase or more, e.g. a 3-fold increase or more, a 4-fold increase or more, a 5-fold increase or more, or a 10-fold increase or more in the number of mammalian cells that express detectable levels of the transgene. As another example, the polynucleotide of the present invention may promote detectable levels of the transgene in a greater percentage of cells as compared to a conventional polynucleotide cassette; for example, where a conventional cassette may promote detectable levels of transgene expression in, for example, less than 5% of the cells in a certain region, the polynucleotide of the present invention promotes detectable levels of expression in 5% or more of the cells in that region; e.g. 10% or more, 15% or more, 20% or more, 25% or more, 30% or more, 35% or more, 40% or more, or 45% or more, in some instances 50% or more, 55% or more; 60% or more, 65% or more, 70% or more, or 75% or more, for example 80% or more, 85% or more, 90% or more, or 95% or more of the cells that are contacted, will express detectable levels of gene product. Enhanced expression may also be observed as an alteration in the viability and/or function of the cells.

The polynucleotide cassettes of the present disclosure typically comprise a promoter region. Any suitable promoter region or promoter sequence therein can be used in the subject polynucleotide cassettes, so long as the promoter region promotes expression of a coding sequence in eukaryotic cells. In certain embodiments, the promoter region promoter expression of a coding sequence in mammalian cells. In some instances, the promoter is a ubiquitous promoter, i.e., it is a promoter that is active in a wide range of cells, tissues and species. In other instances, the promoter is a human phosphoglycerate kinase (PGK) promoter.

In some embodiments, the polynucleotide comprises one or more enhancers. Enhancers are nucleic acid elements known in the art to enhance transcription, and can be located anywhere in association with the gene they regulate, e.g. upstream, downstream, within an intron, etc. Any enhancer element can be used in the polynucleotide cassettes and gene therapy vectors of the present disclosure, so long as it enhances expression of the gene when used in combination with the promoter.

The coding sequence to be expressed in the cells can be any polynucleotide sequence, e.g. gene or cDNA that encodes a gene product, e.g. a polypeptide or RNA-based therapeutic (siRNA, antisense, ribozyme, shRNA, etc.). The coding sequence may be heterologous to the promoter sequence to which it is operably linked, i.e. not naturally operably associated with it. Alternatively, the coding sequence may be endogenous to the promoter sequence to which it is operably linked, i.e. is associated in nature with that promoter. The gene product may act intrinsically in the mammalian cell, or it may act extrinsically, e.g. it may be secreted. For example, when the transgene is a therapeutic gene, the coding sequence may be any gene that encodes a desired gene product or functional fragment or variant thereof that can be used as a therapeutic for treating a disease or disorder. In various preferred embodiments, the transgene encodes human PKLR.

In one embodiment of the invention, the transgene coding sequence is modified, or "codon optimized" to enhance expression by replacing infrequently represented codons with more frequently represented codons. The coding sequence is the portion of the mRNA sequence that encodes the amino acids for translation. During translation, each of 61 trinucleotide codons are translated to one of 20 amino acids, leading to a degeneracy, or redundancy, in the genetic code. However, different cell types, and different animal species, utilize tRNAs (each bearing an anticodon) coding for the same amino acids at different frequencies. When a gene sequence contains codons that are infrequently represented by the corresponding tRNA, the ribosome translation machinery may slow, impeding efficient translation. Expression can be improved via "codon optimization" for a particular species, where the coding sequence is altered to encode the same protein sequence, but utilizing codons that are highly represented, and/or utilized by highly expressed human proteins (Cid-Arregui et al., 2003; J. Virol. 77: 4928). In one aspect of the present invention, the coding sequence of the transgene is modified to replace codons infrequently expressed in mammal or in primates with codons frequently expressed in primates. For example, in some embodiments, the coding sequence encoded by the transgene encodes a polypeptide having at least 85% sequence identity to a polypeptide encoded by a sequence disclosed above or herein, for example at least 90% sequence identity, e.g. at least 95% sequence identity, at least 98% identity, at least 99% identity, wherein at least one codon of the coding sequence has a higher tRNA frequency in humans than the corresponding codon in the sequence disclosed above or herein.

In an additional embodiment of the invention, the transgene coding sequence is modified to enhance expression by termination or removal of open reading frames (ORFs) that do not encode the desired transgene. An open reading frame (ORF) is the nucleic acid sequence that follows a start codon and does not contain a stop codon. ORFs may be in the forward or reverse orientation, and may be "in frame" or "out of frame" compared with the gene of interest. Such open reading frames have the potential to be expressed in an expression cassette alongside the gene of interest, and could lead to undesired adverse effects. In one aspect of the present invention, the coding sequence of the transgene has been modified to remove open reading frames by further altering codon usage. This was done by eliminating start codons (ATG) and introducing stop codons (TAG, TAA, or TGA) in reverse orientation or out-of-frame ORFs, while preserving the amino acid sequence and maintaining highly utilized codons in the gene of interest (i.e., avoiding codons with frequency<20%). In the present invention, the transgene coding sequence may be optimized by either of codon optimization and removal of non-transgene ORFs or using both techniques. As will be apparent to one of ordinary skill in the art, it is preferable to remove or minimize non-transgene ORFs after codon optimization in order to remove ORFs introduced during codon optimization.

In some embodiments, the polynucleotide cassette of the present invention further comprises an RNA export signal. Exemplary RNA export sequences include but are not limited to sequences from woodchuck hepatitis virus post-transcriptional element (WPRE). The woodchuck hepatitis virus (WHV) post-transcriptional regulatory element (Wpre) significantly increases transgene expression in target cells, by increasing RNA stability in a transgene, promoter and vector-independent manner (Zuffrey et al, 1999). However, it can express a truncated 60-amino acid protein derived from the WHV X gene involved in liver cancer (Kingsman et al, 2005). Therefore, most pre-clinical protocols and clinical trials include a mutated version of the Wpre element (Zanta-Boussif et al, 2009). On the other hand, the use of two SV40-USE elements in SIN-LV vectors has been seen to be more efficient than WPRE sequence in suppressing transcriptional read through (Schambach et al, 2007). More precisely, the WPRE disclosed herein is a chimeric WPRE that carries 589 nucleotides from the modified WPRE performed by Axel Schambach (nucleotides 1-589) (WO 2008136670 A2; [5]) and 88 from a former WPRE (nucleotide 590-677) (Zuffrey et al, 1999). Data disclosed herein shows this chimeric wpre works better than the former WPRE. The chimeric WPRE sequence comprises the sequence listed in the table below.

TABLE 1

Modified WPRE sequence

CGAGCATCTTACCGCCATTTATTCCCATATTTGTTCTGTTTTTCTTGATT
TGGGTATACATTTAAATGTTAATAAAACAAAATGGTGGGGCAATCATTTA
CATTTTTAGGGATATGTAATTACTAGTTCAGGTGTATTGCCACAAGACAA
ACATGTTAAGAAACTTTCCCGTTATTTACGCTCTGTTCCTGTTAATCAAC
CTCTGGATTACAAAATTTGTGAAAGATTGACTGATATTCTTAACTATGTT
GCTCCTTTTACGCTGTGTGGATATGCTGCTTTAATGCCTCTGTATCATGC
TATTGCTTCCCGTACGGCTTTCGTTTTCTCCTCCTTGTATAAATCCTGGT
TGCTGTCTCTTTATGAGGAGTTGTGGCCCGTTGTCCGTCAACGTGGCGTG
GTGTGCTCTGTGTTTGCTGACGCAACCCCCACTGGCTGGGGCATTGCCAC
CACCTGTCAACTCCTTTCTGGGACTTTCGCTTTCCCCCTCCCGATCGCCA
CGGCAGAACTCATCGCCGCCTGCCTTGCCCGCTGCTGGACAGGGGCTAGG
TTGCTGGGCACTGATAATTCCGTGGTGTTGTCGGGGAAGGGCCTGCTGCC
GGCTCTGCGGCCTCTTCCGCGTCTTCGCCTTCGCCCTCAGACGAGTCGGA
TCTCCCTTTGGGCCGCCTCCCCGCCTG (SEQ ID NO: 1)

The present invention also include a nucleic acid, e.g., a polynucleotide sequence, comprising a sequence having at least 80%, at least 85%, at least 90%, at least 95%, at least 98%, or at least 99% identity to the sequence set forth in SEQ ID NO:1 or SEQ ID NO:9. In particular embodiments, the polynucleotide sequence comprises the sequence set forth in SEQ ID NO:1 or SEQ ID NO:9.

In particular embodiments of any of the expression cassettes and gene delivery vectors described herein, the Wpre sequence comprises or consists of the sequence of SEQ ID NO:1, or a sequence having at least 80%, at least 85%, at least 90%, at least 95%, at least 98%, or at least 99% identity to the sequence of SEQ ID NO:1.

In particular embodiments of any of the expression cassettes and gene delivery vectors described herein, the Wpre sequence comprises or consists of the following sequence, or a sequence having at least 80%, at least 85%, at least 90%, at least 95%, at least 98%, or at least 99% identity to the following sequence:

(SEQ ID NO: 9)
CGAGCATCTTACCGCCATTTATTCCCATATTTGTTCTGTTTTTCTTGATT

TGGGTATACATTTAAATGTTAATAAAACAAAATGGTGGGGCAATCATTTA

CATTTTTAGGGATATGTAATTACTAGTTCAGGTGTATTGCCACAAGACAA

ACATGTTAAGAAACTTTCCCGTTATTTACGCTCTGTTCCTGTTAATCAAC

CTCTGGATTACAAAATTTGTGAAAGATTGACTGATATTCTTAACTATGTT

```
GCTCCTTTTACGCTGTGTGGATATGCTGCTTTAATGCCTCTGTATCATGC

TATTGCTTCCCGTACGGCTTTCGTTTTCTCCTCCTTGTATAAATCCTGGT

TGCTGTCTCTTTATGAGGAGTTGTGGCCCGTTGTCCGTCAACGTGGCGTG

GTGTGCTCTGTGTTTGCTGACGCAACCCCCACTGGCTGGGGCATTGCCAC

CACCTGTCAACTCCTTTCTGGGACTTTCGCTTTCCCCCTCCCGATCGCCA

CGGCAGAACTCATCGCCGCCTGCCTTGCCCGCTGCTGGACAGGGGCTAGG

TTGCTGGGCACTGATAATTCCGTGGTGTTGTCGGGGAAGGGCCTGCTGCC

GGCTCTGCGGCCTCTTCCGCGTCTTCGCCTTCGCCCTCAGACGAGTCGGA

TCTCCCTTTGGGCCGCCTCCCCGCCTG.
```

In certain embodiments, an expression cassette or gene delivery vector, e.g., a lentivirus, comprises a polynucleotide sequence comprising the following sequences in 5' to 3' order:
(a) a PGK promoter sequence, optionally a human PGK promoter sequence;
(b) a sequence encoding a pyruvate kinase polypeptide, optionally a codon optimized RPK coding or cDNA sequence; and
(c) a mutant Wpre sequence, optionally comprising or consisting of the sequence of SEQ ID NO:1.

In certain embodiments, an expression cassette or gene delivery vector, e.g., a lentivurus, comprises a polynucleotide sequence comprising the following sequences in 5' to 3' order:
(a) a cPPT sequence;
(b) PGK promoter sequence, optionally a human PGK promoter sequence;
(c) a sequence encoding a pyruvate kinase polypeptide, optionally a codon optimized RPK coding or cDNA sequence; and
(d) a mutant Wpre sequence, optionally comprising or consisting of the sequence of SEQ ID NO:1.

In certain embodiments, an expression cassette or gene delivery vector, e.g., a lentivurus, comprises a polynucleotide sequence comprising the following sequences in 5' to 3' order:
(a) a 5' LTR, optionally a modified 5' LTR;
(b) a cPPT sequence;
(c) PGK promoter sequence, optionally a human PGK promoter sequence;
(d) a sequence encoding a pyruvate kinase polypeptide, optionally a codon optimized RPK coding or cDNA sequence;
(e) a mutant Wpre sequence, optionally comprising or consisting of the sequence of SEQ ID NO:1; and
(f) a 3' LTR, optionally a modified 3' LTR.

Figure 21:
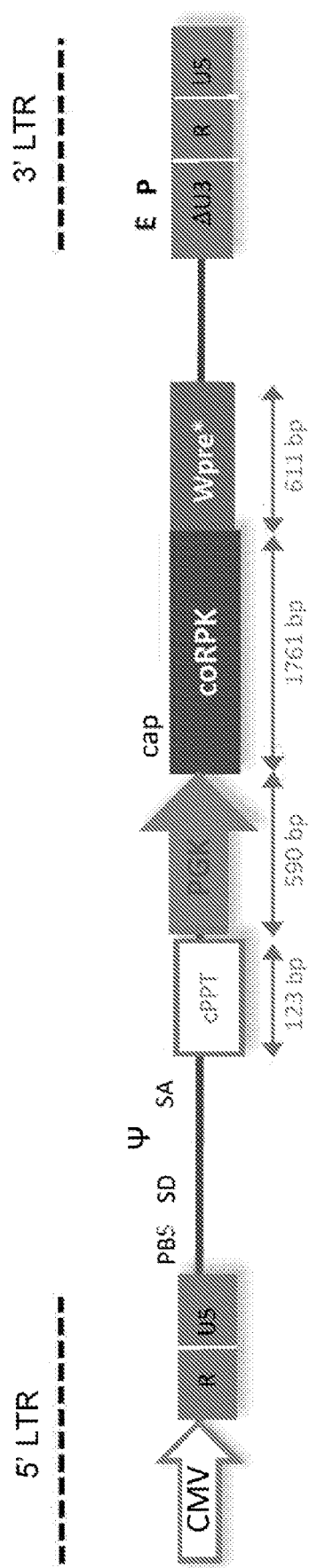
FIG. 21 depicts a schematic diagram of the medicinal product (PGK-coRPK LV).

In certain embodiments, the gene delivery vector is PGK-coRPK LV, or comprises the elements depicted in FIG. 21.

In particular embodiments of any of the expression cassettes and gene delivery vectors described herein, the codon optimized RPK cDNA or coding sequence encodes a PKLR polypeptide that comprises or consists of the sequence disclosed in any of GenBank accession Nos. XP_016856982.1, XP_011507942.1, XP_006711449.1, NP_870986.1, or NP_000289.1, or a functional fragment of any of these sequences, or a sequence having at least 80%, at least 85%, at least 90%, at least 95%, at least 98%, or at least 99% identity to any of these sequences.

Other combinations of elements both as disclosed herein or as known in the art will be readily appreciated by the ordinarily skilled artisan.

Additionally, as will be recognized by one of ordinary skill in the art, the polynucleotide cassettes may optionally contain other elements including, but not limited to restriction sites to facilitate cloning and regulatory elements for a particular gene expression vector.

In some aspects of the present invention, the subject polynucleotide cassettes are used to deliver a gene to cells of an animal, e.g. to determine the effect that the gene has on cell viability and/or function, to treat a cell disorder, etc. Accordingly, in some aspects of the invention, the composition that provides for the expression of a transgene in mammalian cells is a gene delivery vector, wherein the gene delivery vector comprises the polynucleotide cassettes of the present disclosure.

Any convenient gene therapy vector that finds use delivering polynucleotide sequences to mammalian cells is encompassed by the gene delivery vectors of the present disclosure. For example, the vector may comprise single or double stranded nucleic acid, e.g. single stranded or double stranded DNA. For example, the gene delivery vector may be DNA, e.g., a naked DNA, e.g. a plasmid, a minicircle, etc. The vector may comprise single-stranded or double-stranded RNA, including modified forms of RNA. In another example, the gene delivery vector may be an RNA, e.g., an mRNA or modified mRNA.

As another example, the gene delivery vector may be a viral vector derived from a virus, e.g. an adenovirus, an adeno-associated virus, a lentivirus (LV), a herpes virus, an alpha virus or a retrovirus, e.g., Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) or lentivirus. While embodiments encompassing the use of lentivirus are described in greater detail below, it is expected that the ordinarily skilled artisan will appreciate that similar knowledge and skill in the art can be brought to bear on non-LV gene therapy vectors as well. In some embodiments, the gene delivery vector is a self-limiting lentivirus.

In such embodiments, the subject polynucleotide cassette is flanked on the 5' and 3' ends by functional long terminal repeat (LTR) sequences. In one embodiment, the position of different elements present in the backbone of the lentiviral vector is depicted in FIG. 1. Both LTR sequences have been modified to generate self-inactivating (SIN) LV vectors. SIN vectors have a 400 by deletion in the 3'-LTR, covering the promoter/enhancer elements from the U3 region. Expression of the transgene is thereby dependent on internal promoters, reducing the risk of RCLs and decreasing promoter interference (Ginn et al, 2003). This 3'LTR deletion removes the TATA box, preventing transcription initiation (Miyoshi et al. 1998; Zuffrey et al 1998); and therefore inactivating the vector. The U3 region of the 5'-LTR has been replaced by other heterologous promoting sequences (i.e. CMV or RSV) to achieve a Tat-independent transcription and to increase genomic RNA synthesis, resulting in the increase of the viral titer. Because 5'-U3 region drives the expression of primary transcripts, its modifications will not be present in transduced cells (Schambach et al. 2009). Exogenous elements, such as β-globin or SV40 polyadenylation signals (Iwakuma et al, 1999) or the upstream sequence element (USE) from simian virus 40 (SV40-USE) (Schambach et al. 2007), have also been included in the R region of the viral 3'LTR in order to decrease the transcriptional readthrough from the internal promoters (Zaiss et al, 2002) or from remnants of the deleted U3 region of SIN-LV vectors (Almarza et al. 2011) preventing the potential transcriptional activation of the downstream genes. The leader region contains the packaging signal (Ψ), and LV vectors were thought to require approximately 300 by of the Gag gene in this region. Currently, this Gag sequence has been reduced to just 40 by (FIG. 1). The Rev responsive element (RRE) has also been included to improve the efficiency of gene transfer, although it contains surrounding Env remnants. The central polypurine tract (cPPT), which facilitates nuclear translocation of the pre-integration complexes, together with the central terminal sequence (CTS) involved in the separation of reverse transcriptase, has been seen to improve viral titer (Zennou, et al. 2000; Follenzi et al. 2000). In particular embodiments, the cPPT present in any of the expression cassettes or gene delivery vectors described herein comprises or consists of the following sequence: TTTAAAAGAAAAGGGGGAT-TGGGGGGT (SEQ ID NO:2), or a sequence having at least 80%, at least 85%, at least 90%, at least 95%, at least 98%, or at least 99% identity to SEQ ID NO:2.

The dNEF/PPT signal is essential for reverse transcription, and its incorporation significantly improves LV vector production.

Gene therapy vectors encapsulating the polynucleotide cassettes of the present disclosure may be produced using standard methodology. For example, in the case of LV virions, an LV expression vector according to the invention may be introduced into a producer cell, followed by introduction of an LV helper construct, where the helper construct includes LV coding regions capable of being expressed in the producer cell and which complement LV helper functions absent in the LV vector. This is followed by introduction of helper virus and/or additional vectors into the producer cell, wherein the helper virus and/or additional vectors provide accessory functions capable of supporting efficient LV virus production. The producer cells are then cultured to produce LV. These steps are carried out using standard methodology.

Any suitable method for producing viral particles for delivery of the subject polynucleotide cassettes can be used, including but not limited to those described in the examples that follow. Any concentration of viral particles suitable to effectively transducer mammalian cells can be prepared for contacting mammalian cells in vitro or in vivo. For example, the viral particles may be formulated at a concentration of $10^8$ vector genomes per ml or more, for example, $5\times10^8$ vector genomes per mL; $10^9$ vector genomes per mL; $5\times10^9$ vector genomes per mL, $10^{10}$ vector genomes per mL, $5\times10^{19}$ vector genomes per mL; $10^{11}$ vector genomes per mL; $5\times10^{11}$ vector genomes per mL; $10^{12}$ vector genomes per mL; $5\times10^{12}$ vector genomes per mL; $10^{13}$ vector genomes per mL; $1.5\times10^{13}$ vector genomes per mL; $3\times10^{13}$ vector genomes per mL; $5\times10^{13}$ vector genomes per mL; $7.5\times10^{13}$ vector genomes per mL; $9\times10^{13}$ vector genomes per mL; $1\times10^{14}$ vector genomes per mL, $5\times10^{14}$ vector genomes per mL or more, but typically not more than $1\times10^{15}$ vector genomes per mL.

In preparing the subject LV compositions, any host cells for producing LV virions may be employed, including, for example, mammalian cells (e.g. 293 cells), insect cells (e.g. SF9 cells), microorganisms and yeast. Host cells can also be packaging cells in which the LV rep and cap genes are stably maintained in the host cell or producer cells in which the LV vector genome is stably maintained and packaged. Exemplary packaging and producer cells are derived from SF-9, 293, A549 or HeLa cells. LV vectors are purified and formulated using standard techniques known in the art.

In certain embodiments, the present invention includes a cell comprising an expression cassette or gene delivery vector disclosed herein. In related embodiments, the cell is transduced with a viral vector comprising an expression cassette disclosed herein or has an expression cassette disclosed herein integrated into the cell's genome. In certain embodiments, the cell is a cell used to produce a viral gene delivery vector. In other embodiments, the cell is a cell to be delivered to a subject in order to provide to the subject the gene product encoded by the expression cassette. Thus, in certain embodiments, the cell is autologous to the subject to be treated or was obtained from the subject to be treated. In other embodiments, the cell is allogeneic to the subject to be treated or was obtained from a donor other than the subject to be treated. In particular embodiments, the cell is a mammalian cell, e.g., a human cell. In certain embodiments, the cell is a blood cell, an erythrocyte, a hematopoietic progenitor cell, a bone marrow cell, e.g., a lineage depleted bone marrow cell, a hematopoietic stem cell (e.g., CD34+) or a committed hematopoietic erythroid progenitor cell The present invention includes pharmaceutical compositions comprising a polynucleotide cassette, gene delivery vector, or cell described herein and a pharmaceutically-acceptable carrier, diluent or excipient. The subject polynucleotide cassette, gene delivery vector, or cell can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such excipients, carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfate; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile.

Pharmaceutical compositions suitable for use in the present invention further include sterile aqueous solutions or dispersions and sterile powders for the extemporaneous preparation of sterile injectable solutions or dispersion.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the compositions are prepared with carriers that will protect the gene cassette or expression vector against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially.

It is especially advantageous to formulate oral, ocular or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser, e.g. syringe, e.g. a prefilled syringe, together with instructions for administration.

The pharmaceutical compositions of the invention encompass any pharmaceutically acceptable salts, esters, or salts of such esters, or any other compound which, upon administration to an animal comprising a human, is capable of providing (directly or indirectly) the biologically active metabolite or residue thereof.

The term "pharmaceutically acceptable salt" refers to physiologically and pharmaceutically acceptable salts of the compounds of the invention: i.e., salts that retain the desired biological activity of the parent compound and do not impart undesired toxicological effects thereto. A variety of pharmaceutically acceptable salts are known in the art and described, e.g., in in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see Handbook of Pharmaceutical Salts: Properties, Selection, and Use by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

The subject polynucleotide cassette, gene delivery vector, e.g., recombinant virus (virions), or cell (e.g., transduced with a gene delivery vector disclosed herein) can be incorporated into pharmaceutical compositions for administration to mammalian patients, particularly primates and more particularly humans. The subject polynucleotide cassette, gene delivery vector, e.g. virions, or cell can be formulated in nontoxic, inert, pharmaceutically acceptable aqueous carriers, preferably at a pH ranging from 3 to 8, more preferably ranging from 6 to 8. Such sterile compositions will comprise the vector or virion containing the nucleic acid encoding the therapeutic molecule dissolved in an aqueous buffer having an acceptable pH upon reconstitution.

In some embodiments, the pharmaceutical composition provided herein comprise a therapeutically effective amount of a cell, vector or virion disclosed herein in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer in which the pharmaceutical composition comprising the tumor suppressor gene contained in the adenoviral vector delivery system, may be in the range of 6.5 to 7.75, preferably 7 to 7.5, and most preferably 7.2 to 7.4.

In certain embodiments, viral vectors may be formulated into any suitable unit dosage, including, without limitation, $1\times10^8$ vector genomes or more, for example, $1\times10^9$, $1\times10^{10}$, $1\times10^{11}$, $1\times10^{12}$, or $1\times10^{13}$ vector genomes or more, in certain instances, $1\times10^{14}$ vector genomes, but usually no more than $4\times10^{15}$ vector genomes. In some cases, the unit dosage is at most about $5\times10^{15}$ vector genomes, e.g. $1\times10^{14}$ vector genomes or less, for example $1\times10^{13}$, $1\times10^{12}$, $1\times10^{11}$, $1\times10^{10}$, or $1\times10^9$ vector genomes or less, in certain instances $1\times10^8$ vector genomes or less, and typically no less than $1\times10^8$ vector genomes. In some cases, the unit dosage is $1\times10^1$ to $1\times10^{11}$ vector genomes. In some cases, the unit dosage is $1\times10^{10}$ to $3\times10^{12}$ vector genomes. In some cases, the unit dosage is $1\times10^9$ to $3\times10^{13}$ vector genomes. In some cases, the unit dosage is $1\times10^8$ to $3\times10^{14}$ vector genomes. In one embodiment, the range is from about $5\times10^{10}$ to about $1\times10^{11}$ vector genomes. In some embodiments, the range is from about $1\times10^9$ to about $1\times10^{10}$ vector genomes.

In some cases, the unit dosage of a pharmaceutical composition may be measured using multiplicity of infection (MOI). By MOI it is meant the ratio, or multiple, of vector or viral genomes to the cells to which the nucleic acid may be delivered. In some cases, the MOI may be $1\times10^6$. In some cases, the MOI may be $1\times10^5$-$1\times10^7$. In some cases, the MOI may be $1\times10^4$-$1\times10^8$. In some cases, recombinant viruses of this disclosure are at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, recombinant viruses of this disclosure are $1\times10^8$ to $3\times10^{14}$ MOI_In some cases, recombinant viruses of the disclosure are at most about $1\times10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI. In some, embodiments the range is from about 20 to about 400 MOI.

In some aspects, the amount of pharmaceutical composition comprises about $1 \times 10^8$ to about $1 \times 10^{15}$ recombinant viruses, about $1 \times 10^9$ to about $1 \times 10^{14}$ recombinant viruses, about $1 \times 10^{10}$ to about $1 \times 10^{13}$ recombinant viruses, or about $1 \times 10^{11}$ to about $3 \times 10^{12}$ recombinant viruses.

Methods

As disclosed herein, the subject polynucleotide cassettes and gene delivery vectors, referred to collectively herein as the "subject compositions", find use in expressing a transgene in cells of an animal. For example, the subject compositions may be used in research, e.g. to determine the effect that the gene has on cell viability and/or function. As another example, the subject compositions may be used in medicine, e.g. to treat or prevent a disease or disorder. Thus, in some aspects of the invention, methods are provided for the expression of a gene in cells, the method comprising contacting cells with a composition of the present disclosure. In some embodiments, contacting occurs in vitro or ex vivo. In some embodiments, contacting occurs in vivo, i.e., the subject composition is administered to a subject.

For instances in which mammalian cells are to be contacted in vitro or ex vivo with a subject polynucleotide cassette or gene delivery vector comprising a subject polynucleotide cassette, the cells may be from any mammalian species, e.g. rodent (e.g. mice, rats, gerbils, squirrels), rabbit, feline, canine, goat, ovine, pig, equine, bovine, primate, human. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

Embodiments of the present invention comprise mammalian cells (e.g., CD34+ cells) transduced with a viral delivery vector, e.g., a lentiviral vector containing the human liver and erythroid pyruvate kinase (PKLR) gene. Accordingly, the present invention includes a method of transducing a mammalian cell, e.g. a human hematopoietic stem cell or other cell described herein, comprising contacting the cell with a viral delivery vector, e.g., a lentiviral vector, comprising an expression cassette described herein. In certain embodiments, the cell was previously obtained from a subject to be treated, or from another donor. In particular embodiments, the subject was diagnosed with PKD, and the cell is transduced with a LV comprising an expression cassette encoding pyruvate kinase, e.g., a codon-optimized RPK coding region or cDNA. It is understood that the disclosed methods, e.g., those used to deliver a pyruvate kinase gene product, e.g., using a coPRK cDNA sequence, to a subject may also be used to treat hemolytic anemia, and/or normalize erythroid differentiation, increase the number of functional mature erythrocytes, reduce extramedullar erythropoiesis, reduce splenomegaly and other secondary effects of hemolytic anemia or PKD.

To promote expression of the transgene, the subject polynucleotide cassette or gene delivery vector comprising a subject polynucleotide cassette will be contacted with the cells for about 30 minutes to 24 hours or more, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, 24 hours, etc.

The subject polynucleotide cassette or gene delivery vector comprising a subject polynucleotide cassette may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further. Contacting the cells may occur in any culture media and under any culture conditions that promote the survival of the cells. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Typically, an effective amount of subject polynucleotide cassette or gene delivery vector comprising a subject polynucleotide cassette is provided to produce the expression of the transgene in cells. As discussed elsewhere herein, the effective amount may be readily determined empirically, e.g. by detecting the presence or levels of transgene gene product, by detecting an effect on the viability or function of the cells, etc. Typically, an effect amount of subject polynucleotide cassette or gene delivery vector comprising a subject polynucleotide cassette will promote greater expression of the transgene in cells than the same amount of a polynucleotide cassette as known in the art. Typically, expression will be enhanced 2-fold or more relative to the expression from a reference, or control, polynucleotide cassette e.g. as known in the art, for example 3-fold, 4-fold, or 5-fold or more, in some instances 10-fold, 20-fold or 50-fold or more, e.g. 100-fold.

For instances in which cells are to be contacted in vivo with a subject polynucleotide cassette or gene delivery vector comprising a subject polynucleotide cassette, the subject may be any mammal, e.g. rodent (e.g. mice, rats, gerbils), rabbit, feline, canine, goat, ovine, pig, equine, bovine, or primate. In a further preferred embodiment, the primate is a human. In a further embodiment, the cells are CD34+ cells.

The methods and compositions of the present disclosure find use, e.g., in the treatment of pyruvate kinase deficiency.

In another embodiment, the present invention includes a method of treating a disease in a subject in need thereof comprising providing to the subject an effective amount of cells transduced with a gene delivery vector, e.g., a viral vector, that expresses a therapeutic gene product in the cells. In particular embodiments, the cells are autologous to the subject. In certain embodiments, the cells are erythroid cells, e.g., hematopoietic stem cells or committed hematopoietic erythroid progenitor cells. In some embodiments, the cell is a bone marrow cell, e.g., a lineage depleted bone marrow cell. In particular embodiments, the method is used to treat PKD, and the viral vector is a LV comprising an expression construct disclosed herein comprising a human PGK promoter operably linked to a codon optimized human PKLR gene cDNA or coding sequence, and a mutated Wpre disclosed herein. In particular embodiments, the cells are provided to the subject parenterally, e.g., via intravenous injection.

In another embodiment, the present invention includes a method of treating PKD in a subject in need thereof, comprising providing to the subject an effective amount of autologous C34+ stem cells transduced with a lentiviral vector that expresses a codon optimized PKLR cDNA in the cells, wherein the lentiviral vector comprises a human PGK promoter operably linked to the codon optimized human PKLR cDNA or coding sequence, and a mutated Wpre sequence disclosed herein. In particular embodiments, the cells are hematopoietic stem cells or committed hematopoietic erythroid progenitor cells, e.g., bone marrow cells. In particular embodiments, the cells are provided to the subject parenterally, e.g., via intravenous injection.

In another embodiment, the present invention provides a of treating a disease in a subject in need thereof comprising providing to the subject an effective amount of a gene delivery vector, e.g., a viral vector, that expresses a therapeutic gene product in the subject. In particular embodiments, the method is used to treat PKD, and the viral vector is a LV comprising an expression construct disclosed herein comprising a human PGK promoter operably linked to a codon optimized human PKLR gene cDNA or coding sequence, and a mutated Wpre disclosed herein. In particular embodiments, the gene delivery vector are provided to the subject parenterally, e.g., via intravenous injection.

In particular embodiments, the cells or gene delivery vectors are provided to the subject in pharmaceutical compositions.

In some embodiments, the subject methods result in a therapeutic benefit, e.g. preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy.

Expression of the transgene using the subject transgene is expected to be robust. Accordingly, in some instances, the expression of the transgene, e.g. as detected by measuring levels of gene product, by measuring therapeutic efficacy, etc. may be observed two months or less after administration, e.g. 4, 3 or 2 weeks or less after administration, for example, 1 week after administration of the subject composition. Expression of the transgene is also expected to persist over time. Accordingly, in some instances, the expression of the transgene, e.g. as detected by measuring levels of gene product, by measuring therapeutic efficacy, etc., may be observed 2 months or more after administration of the subject composition, e.g., 4, 6, 8, or 10 months or more, in some instances 1 year or more, for example 2, 3, 4, or 5 years, in certain instances, more than 5 years.

In certain embodiments, the method comprises the step of detecting expression of the transgene in the cells or in the subject, wherein expression is enhanced relative to expression from a polynucleotide cassette not comprising the one or more improved elements of the present disclosure. Typically, expression will be enhanced 2-fold or more relative to the expression from a reference, i.e. a control polynucleotide cassette, e.g. as known in the art, for example 3-fold, 4-fold, or 5-fold or more, in some instances 10-fold, 20-fold or 50-fold or more, e.g. 100-fold, as evidenced by, e.g. earlier detection, higher levels of gene product, a stronger functional impact on the cells, etc.

Typically, if the subject composition is an LV comprising the subject a polynucleotide cassette of the present disclosure, an effective amount to achieve a change in will be about $1\times10^8$ vector genomes or more, in some cases $1\times10^9$, $1\times10^{10}$, $1\times10^{11}$, $1\times10^{12}$, or $1\times10^{13}$ vector genomes or more, in certain instances, $1\times10^{14}$ vector genomes or more, and usually no more than $1\times10^{15}$ vector genomes. In some cases, the amount of vector genomes that is delivered is at most about $1\times10^{15}$ vector genomes, e.g. $1\times10^{14}$ vector genomes or less, for example $1\times10^{13}$, $1\times10^{12}$, $1\times10^{11}$, $1\times10^{10}$, or $1\times10^9$ vector genomes or less, in certain instances $1\times10^8$ vector genomes, and typically no less than $1\times10^8$ vector genomes. In some cases, the amount of vector genomes that is delivered is $1\times10^{10}$ to $1\times10^{11}$ vector genomes. In some cases, the amount of vector genomes that is delivered is $1\times10^{10}$ to $3\times10^{12}$ vector genomes. In some cases, the amount of vector genomes that is delivered is $1\times10^9$ to $3\times10^{13}$ vector genomes. In some cases, the amount of vector genomes that is delivered is $1\times10^8$ to $3\times10^{14}$ vector genomes.

In some cases, the amount of pharmaceutical composition to be administered may be measured using multiplicity of infection (MOI. In some cases, MOI may refer to the ratio, or multiple of vector or viral genomes to the cells to which the nucleic may be delivered. In some cases, the MOI may be $1\times10^6$. In some cases, the MOI may be $1\times10^5$-$1\times10^7$. In some cases, the MOI may be $1\times10^4$-$1\times10^8$. In some cases, recombinant viruses of the disclosure are at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, recombinant viruses of this disclosure are $1\times10^8$ to $3\times10^{14}$ MOI. In some cases, recombinant viruses of the disclosure are at most about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI.

In some aspects, the amount of pharmaceutical composition comprises about $1\times108$ to about $1\times10^{15}$ particles of recombinant viruses, about $1\times10^9$ to about $1\times10^{14}$ particles of recombinant viruses, about $1\times10^{10}$ to about $1\times10^{13}$ particles of recombinant viruses, or about $1\times10^{11}$ to about $3\times10^{12}$ particles of recombinant viruses.

Any total number of viral particles suitable to provide appropriate transduction of cells to confer the desired effect or treat the disease can be administered to the mammal. In various preferred embodiments, at least $10^8$; $5\times10^8$; $10^9$; $5\times10^9$, $10^{10}$, $5\times10^{10}$, $10^{11}$, $5\times10^{11}$; $10^{12}$; $5\times10^{12}$; $10^{13}$; $10^{14}$ viral particles or more, but typically not more than $1\times10^{15}$ viral particles are injected. Any suitable number of administrations of the vector to the mammal or the primate eye can be made. In one embodiment, the methods comprise a single administration; in other embodiments, multiple administrations are made over time as deemed appropriate by an attending clinician. In some embodiments at least $2\times10^8$ VG/ml of $5\times10^5$ cells/ml is required in a single administration (24 hours transduction) to result in high transduction efficiencies.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dosage amount. Effective amounts of dose and/or dose regimen can readily be determined empirically from preclinical assays, from safety and escalation and dose range trials, individual clinician-patient relationships, as well as in vitro and in vivo assays such as those described herein and illustrated in the Examples.

Several aspects of the invention are described herein with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing-herein is to be construed as an admission that the present invention is not entitled to antedate such publication by virtue of prior invention. Further, the dates of publication provided may be different from the actual publication dates which may need to be independently confirmed.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety, e.g., to disclose and describe the methods and/or materials in connection with which the publications are cited. It is understood that the present disclosure supersedes any disclosure of an incorporated publication to the extent there is a contradiction.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental Methods

Vectors and lentiviral supernatant production. LVs were generated as described herein. CoRPK sequence was designed using the GeneArt® software to increase the GC content of the sequence and to prevent cryptic splice sites. Vectors were developed using the pCCL.sin.ppt.hPGK-EGFP-Wpre* construct as backbone, generously provided by Dr. Naldini (HSR-TIGET, San Raffaele Telethon Institute, Milano, Italy). Vector stocks of VSVG pseudotyped LVs were prepared by 3-plasmid calcium phosphate-mediated transfection in 293T cells (ATCC: CRL-1573, Rockeville, Md., USA), as previously described [Follenzi A, et al. (2000). Nat Genet 25: 217-222]. Titers of infective LVs were determined in HT1080 cells (ATCC: CCL-121) by qPCR as described elsewhere [Charrier S, et al. (2005). Gene Ther 12: 597-606]. Lentiviral stocks of $10^7$-$10^8$ viral particles (vp)/mL titers were routinely obtained.

Purification and transduction of murine HSCs. BM from 8-14 week-old male PKD mice was harvested from the leg bones and lineage negative cells (Lin⁻) were purified using the Lin⁻ Cell Depletion kit (Miltenyi Biotec, Gladbach, Germany), obtaining 70-90% purity. Lin⁻ cells were pre-stimulated with 100 ng/mL of recombinant human IL-11 (Peprotech EC Ltd., London, UK) and 100 ng/mL of recombinant murine SCF (R&D Systems Inc., Minneapolis, Minn.) in IMDM-Glutamax medium supplemented with 20% FBS and 0.5% antibiotics (50 U/mL penicillin and 50 µg/mL streptomycin, (Thermo Fisher Scientific, Waltham, Mass.) for 24 h, and then transduced with EGFP or coRPK carrying LVs in two cycles of transduction at MOIs of 1-10 vp/cell. Each transduction was carried out for 24 h in the presence of the aforementioned cytokines on plates previously coated with CH-296 fibronectin fragment (2 µg/cm²; Retronectin, TakaraShuzo, Otsu, Japan) overnight at 4° C.

In vivo RBC survival. Transplanted mice carrying the coRPK transgene were injected with three consecutive intravenous injections (12 h apart) of Biotin 3-sulfo-N-hydroxysuccinimide ester sodium salt (50 mg/kg) (Sigma Aldrich, Saint Louis, Mo.). Twelve hours after the last injection, tail vein blood was harvested and labelled with 2 µg/mL of anti-mouse Ter119-PE (BD Bioscience, San Jose, Calif.) and streptavidin-FITC (50 µg/mL, BD Biosciences, San Jose, Calif.) for 30 min at 4° C. Samples were analyzed in an EPICS XL flow cytometer (Beckman Coulter, Brea, Calif.) every 2-4 days for 40 days after the injection. RBC survival kinetics was measured by the percentage of biotinylated cells within the total RBC population.

CFC Assay. CFC assay was performed in BM and spleen from control and transplanted mice according to manufacturer's procedure from Methocult medium GF M3434 (Stem Cell Technologies, Vancouver, Canada). BM cells were harvested at different time-points after transplant from all groups of mice, and CFUs (clusters of 30 or more cells) were scored 7 days after seeding in a Nikon Diaphot-TMD microscope.

Identification of hematopoietic lineages. PBMCs were obtained from the tail vein of transplanted animals and labelled with a panel of antibodies to detect different hematopoietic cells. Myeloid cells were detected with anti-GR-1 and anti-Mac-1 biotinylated antibodies (BD Bioscience, San Jose, Calif., 5 µg/mL), while lymphoid cells were detected using anti-CD3-PE antibody for T-cells, and anti-B220-PE and anti-B220-PECyS antibodies for B-cells (BD Bioscience, San Jose, Calif., 10 µg/mL), together with SAV-TRC secondary antibody (Invitrogen, Thermo Fisher Scientific, Waltham, Mass.). Samples were analysed in a BD LSR Fortessa Cytometer (BD Bioscience, San Jose, Calif." USA) adding DAPI (Boehringer, Ingelheim, Germany, 2 µg/mL) to exclude death cells.

Structural and histological studies. Spleens were collected, photographed and weighed on precision scales to determine the presence of splenomegaly. Histological studies were performed on spleen and liver sections obtained following conventional histological methods, and stained with hematoxylin (Gill-2 Haematoxylin, Thermo, Pittsburgh, USA) and eosin (Eosin Alcoholic, Thermo Fisher Scientific, Waltham, Mass.). Iron deposits were also studied in the spleen by Prussian Blue or Perls' staining (Sigma Aldrich, Saint Louis, Mo.) following manufacturer's instructions. All sections were examined using an Olympus BX40 light microscope and photographed with an Olympus DP21 camera, with a final magnification of 100× or 200×.

Erythroid differentiation. Flow cytometry analysis of Ter119 and CD71 marker intensities in BM and spleen were used to identify the different erythroid subpopulations as described elsewhere [Socolovsky M, et al. (2001). Blood 98: 3261-3273] using 4 µg/mL of anti-mouse Ten 19-PE antibody (BD Bioscience, San Jose, Calif.), 10 µg/mL of biotinylated anti-CD71 antibody (BD Bioscience, San Jose, Calif.) and streptavidin-tricolor (Invitrogen, Thermo Fisher Scientific, Waltham, Mass.). Cells were then analyzed in an EPICS XL flow cytometer (Beckman Coulter, Brea, Calif.) using propidium iodide (IP, 2 µg/mL) to detect live cells.

Provirus quantification. Detection and quantification of integrated provirus per cell was accomplished using complementary primers to the packaging proviral sequence ($\Psi$) and the mouse Titin housekeeping gene. Total BM and peripheral blood samples were collected periodically, and genomic DNA from nucleated cells was isolated using the DNeasy Blood & Tissue kit (Qiagen, Venlo, Limburg, The Netherlands). Twenty to 50 ng of genomic DNA (gDNA) were amplified by multiplex qPCR using the 7500 Fast Real-Time PCR System (Applied Biosystems, Thermo Fisher Scientific, Waltham, Mass.) and primers and probes previously described [Charrier S, et al. (2011). Gene Ther 18: 479-487].

Chimerism. Presence of donor cells was quantified by qPCR detecting the Y chromosome SRY gene and the mouse β-Actin housekeeping gene. Primers and probes previously described [Navarro S et al (2006). Mol Ther 14: 525-535] were used and genomic DNA from PB of transplanted mice was amplified using the 7500 Fast Real-Time PCR System (Applied Biosystems, Thermo Fisher Scientific, Waltham, Mass.). Standard curves were prepared using gDNA extracts from samples containing 0% to 100% of BM cells from male/female mouse mixtures and chimerism was calculated as: % of donor engraftment=$100 \times 2^{(Ct\beta Act-CtSRY)}$.

LAM-PCR procedure. In order to identify vector integration sites, 3' vector LTRgenome junctions were amplified by LAM-PCR following the method published by Schmidt et al. 2007 [Nat Methods 4: 1051-1057]. The starting linear amplification (100 cycles) was performed using biotinylated LTR specific primers and up to 100 ng of gDNA as template. Linear amplification products were purified using streptavidin magnetic beads and followed by complementary strand synthesis, parallel digestion with 2 different restriction enzymes (Tsp509I and HpyCH4IV) and two ligation reactions using linker cassettes complementary to the ends left by the enzyme's cut. The fragments generated were amplified by two additional exponential PCR steps. LAM-PCR products were separated and quantified by gel electrophoresis on a MultiNA automated system (Shimadzu).

Setup of LAM-PCR products for Illumina MiSeq sequencing. Following the method published by Parazynski et al [Paruzynski A, et al. (2010). Nat Protoc 5: 1379-1395], 40 ng of the second exponential PCR products generated by Tsp5091 and HpyCH4IV enzymes were re-amplified using fusion primers containing specific sequences that allow paired end sequencing on an Illumina MiSeq sequencer. LAM-PCR samples were adapted for 454-pyrusequencing by fusion PCR to add the Roche 454 GS-FLX adaptors: adaptor A plus an 8-nucleotide barcode was added to the LTR end of the LAM-PCR amplicon; adaptor B was added to the linker cassette side. In 5'-3' orientation the final amplicon was composed as follow: adaptor A, barcode, LTR sequence, unknown genome sequence, linker cassette sequence and primer B. Purified fusion primer PCR products were run and quantified on a MultiNA automated electrophoresis system, and pooled together in order to obtain a final equimolar library of 10 nM. The final library was then re-quantified using a KAPA Library Quantification Kit for Illumina Sequencing Platform (Kapa Biosystems, Wilmington, Mass.) on a Viia7 real-time PCR system (Applied Biosystems, Thermo Fisher Scientific, Waltham, Mass.), obtaining an estimated concentration of 16.35 nM. Finally, libraries were sequenced using the Illumina MiSeq Reagent Kit.

Bioinformatics analysis. To extract vector integration sites (IS) from a high-throughput sequencing platform, both Roche 454 and Illumina MiSeq/HiSeq, a pipeline taking in input the row data (typically in FastQ file format) was designed, providing the list of reliable IS and the nearest gene. Superior level analyses for clonal abundance quantification and gene ontology enrichment were performed using Excel, GraphPad Prism™ and available online tools.

NGS data processing and pipeline usage. The step of NGS data processing deals with the management of high-throughput data from Illumina MiSeq sequencing platforms and aims at identify IS in which all valid sequence reads are aligned to the reference genome. Data processing comprises two main activities: 1. Data quality inspection and analysis, in which lentiviral vector sequences and other contaminants are trimmed. 2. Integration site identification, in which all valid sequence reads are aligned to the genome of reference and valid ISs are retrieved.

Data quality analysis. In order to identify IS from Illumina MiSeq raw data a bioinformatics pipeline was developed. Standard LAM-PCR products contain a LTR sequence, a flanking human genomic sequence and a linker cassette (LC) sequence. The 459 technology allowed retrieval of LAM-PCR sequences with length ranging from 10 bp to 900 bp. Similar results were retrieved from Illumina MiSeq paired-ends reads. These length boundaries are important parameters to consider in the quality analysis process since they affect both, the subsequent alignment procedure and the algorithm of the vector components identification. Sequences too short to be correctly aligned to the reference gene were discarded, as well as those exceeding the maximum size reachable with NSG technology to avoid missing part or all of the LC sequence. Once the pipeline ends for each pool, all integration sites were collected both in files (archived in the TIGET network attached file storage—NAS—) and in the internal database, and maintained in a storage server that keeps track of the modified copies.

Integration site identification. To identify unique integration sites and extract the excel file with all IS in rows and each sample in columns (IS matrix) with the closest gene annotations, we run the following steps: 1. Creation of the IS matrix using the program called create_matrix, enabling the collision detection inter projects. This program will produce a tab-separated file (TSV); 2. Annotation of the IS matrix file using the program annotate_bed, that will be called as follows for each pool using the input TSV file: awk'{print"chr"'%1"\t"%2"\t"%2}'TSV_FILE|tail-n|2>TSV_FILE.bed; annotate_bed-a/opt/genome/mouse/mm9/annotation/mm9.refGene.TIGET.gtf-b TSV_FILE.bed-o TSV_FILE.annotated.bed; 3. Import both annotation and matrix file into a new Excel worksheet, here on called XLS.

Collision detection. In order to obtain a reliable dataset of ISs from each transplanted mouse, we filtered data from potential contaminations/collisions and from false positives based on sequence counts. An additional step of data normalization was required to combine integration sites resulting from different experiments.

The term "collision" is used to identify the presence of identical IS in independent samples. In our experimental setting, the integration of vector in the very same genomic position in different cells is a very low probability event. Thus, the detection of identical ISs in independent samples likely derives from contamination, which may occur at different stages of wet laboratory procedures (sample purification, DNA extraction, LAM-PCRs and sequencing). Although our working pipeline is designed to minimize the occurrence of inter-samples contacts, the high-throughput analysis of ISs intrinsically carries a certain degree of background contamination. Identification of the extent of contamination between samples is crucial also because the retrieval of the same IS in different samples obtained from the same mouse is used in subsequent steps to make inference on biological properties of the vector-marked hematopoietic cells (i.e. multi-lineage potential and sustained clonogenic activity). Thus, we must be able to distinguish the actual occurrence of the same IS in different samples (from the same mouse) from a contamination/collision. To address these issues, we assessed the extent of shared IS among samples derived from different test items and mice as a way to measure the extent of collision in our analyses and then design rules to discard from each mouse's data set those IS that can be ascribed to collision and minimize the likelihood of scoring false positive when looking for shared IS between samples from the same mouse. We designed a collision detection process allowing the validation of each integration locus. The overall result should be that, given the set I of integration loci, in case of classification of an integration locus i in I as collision, i is discarded from I. We applied collision detection process between 3 independent transplantation groups: 1. coPKR170s: mice from assay 1 euthanized at 170 days after transplant with Lin$^-$ cells transduced with the coRPK expressing LV vector (coRPK 1-3). 2. EGFP: mice from assay 2 transplanted with Lin$^-$ cells carrying the EGFP expressing LV vector (EGFP 1-6). 3. coPKR-TC: mice from assay 2 transplanted with Lin$^-$ cells transduced with the coPKR expressing LV vector (coRPK 1-14), whose blood and BM was analysed at different time-points, including secondary recipients transplanted with a pooled BM from a sub-group of primary transplanted mice (coRPK 11-14).

Each identical IS has different sequence reads (sequence count) among the different mice. Sequence counts can be used to determine whether samples from one mouse contaminated the other mice' samples based on the abundance criterion. In our rationale, an integration found in two mice will be assigned to the mouse that shows the highest abundance, while in the other mouse it will be considered as a contaminant. Therefore, we could identify a threshold of differential sequence count that allows assigning a given collision to a mouse and removing from the others. We retrieved the threshold value from our data obtaining a value of 10, meaning that for each IS, among all TI, if an IS has got an abundance value (percentage sequence count ratio) 10 times lower than the highest abundance value (percentage sequence count) of the other TIs, then it is discarded from the current TI. We applied these rules both among the TI and the selected groups, and Excel files were used to compute the collisions detection by applying the following rules (here detailed for TI filtering but that are extended to groups filtering as well): 1. Isolating each TI, group all samples of the same TI together by summing the sequence counts. 2. For the three TIs obtained, for each IS, compute the percentage ratio of the IS sequence count versus the overall sum of reads for the TI. 3. Then, applying the following rule to compute the decision step with the threshold of 10 that allowed to assigning each IS to a reliable TI.

Once an IS was detected to remove, reads of that IS were removed from the group so that it will no longer assigned also to that group. The filter described above was applied between the mice transplanted with different ex-vivo transduced cell populations (one cohort of EGFP expressing mice from assay 2, and two cohorts of coPKR mice belonging to two independent transplantation experiments). Moreover for the coPKR-TC group (assay 2), the filter method mentioned above was modified in two ways: a) To better highlight the sharing of integrations between time-points in the context of the clonal abundance analysis we added the following rule: if one integration is shared between one or more mice then the integration will be kept for all time points even if their sequence count is less than the 10% of the maximum sequence count among mice; b) For lineage tracking relationships we applied a more stringent filter by eliminating the IS with a sequence count lower than 3 and the 10% sequence count filter for sharing between time-points. Meaning that an integration shared between two time points will be kept or discarded only if is more or less than the other respectively.

Figure 20:
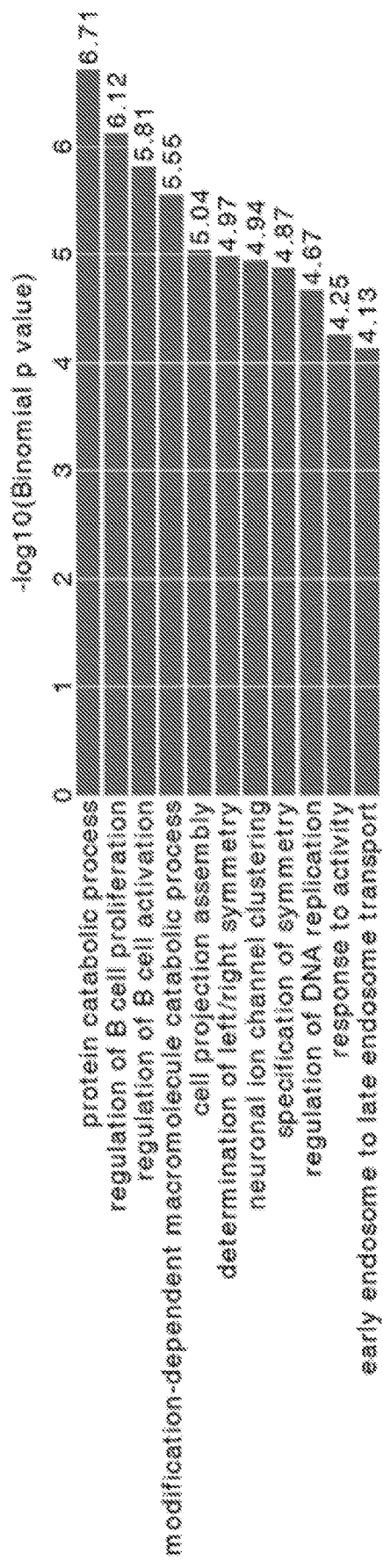
FIG. 20 depicts the LV genomic integration profile. Gene Ontology (GO) analysis was performed using the GREAT software on samples from transplanted mouse. All integrations retrieved from this study (N=2220) showed overrepresentations of the gene functions indicated on the left part of the figure. To address if the most abundant integrations were enriched on specific gene classes, all integration sites with a relative sequence count>5% of the entire dataset (shown in FIG. 17) were selected, showing no GO gene classes overrepresented.

Gene ontology analysis. All gene ontology analyses were made using the GREAT online software (bejerano.stanford.edu/great/public/). The web page allow to upload the genomic coordinates of the integrations of each dataset and calculates the enrichment levels in the tested dataset by correlating positional information (based on the binomial distribution analysis for p-value calculations) and annotated function of the genes nearest to the integration sites (based on the hypergeometric distribution analysis for p-value calculations) [Groeschel S, et al. (2011). J Inherit Metab Dis 34: 1095-1102]. Biological processes and molecular functions of the Gene ontology database were chosen for enrichment analysis. Only the gene classes with a false discovery rate<0.05 for both statistical analyses were considered (FIG. 20).

Data storage. All data, both row data and results, are stored in TIGET network attached file storage (NAS) in the root folder, in which all alignments from the pipeline are available, as well as the abundance matrix and plots. NAS storage is secured by authentication and authorization policies, and was built on a reliable and scalable infrastructure using redundancy array of disks RAID 5, and it is under backup on our CrashPlan software registered in TIGET.

Example 1

Figure 2A:
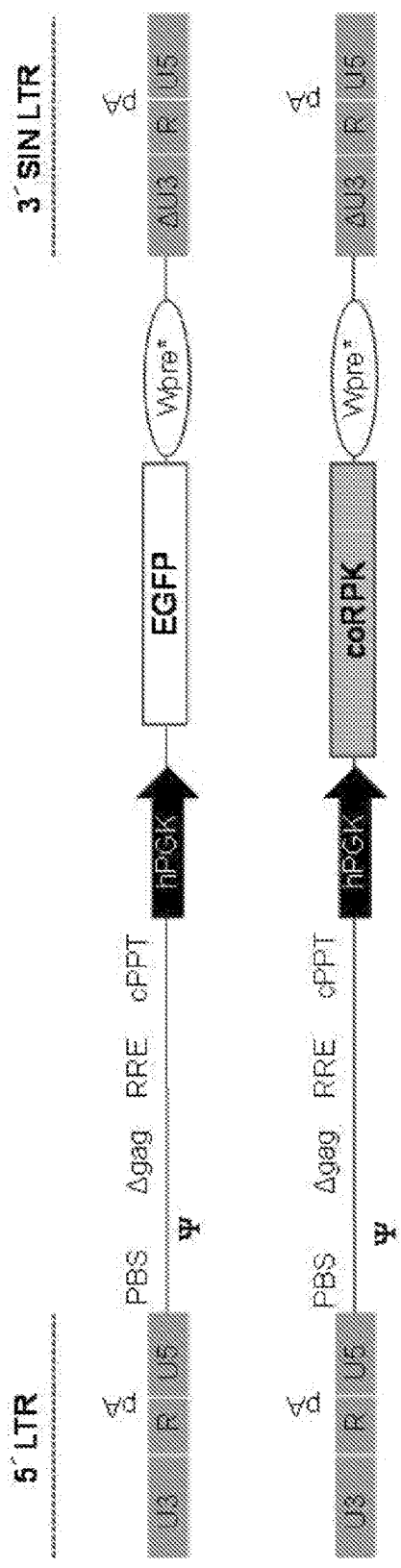
FIG. 2A is a schematic representation of the self-inactivating lentiviral vectors used throughout gene therapy experiments harboring the human PGK promoter regulating the expression of the EGFP transgene in the control vector (upper diagram) or the expression of a codon-optimized sequence of the PKLR gene cDNA (coRPK) in the therapeutic vector (lower diagram).
Figure 2B:
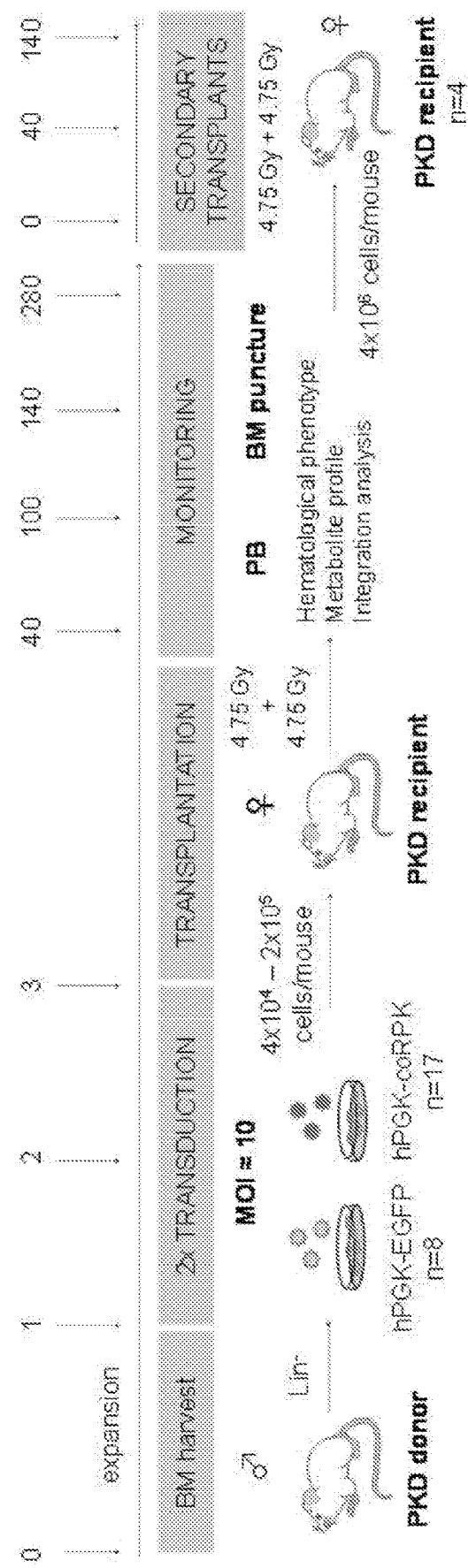
FIG. 2b is a schematic gene therapy protocol performed to address the functionality of the developed PGK-coRPK lentiviral vector.

PGK-coRPK Therapeutic Lentiviral Vector Leads to a Stable And Long-Term Correction of the Anemic Phenotype in Genetically Corrected PKD Mice In vivo efficacy of the PGK-coRPK LV (FIG. 2*a*) was assayed by transduction and transplantation of lineage depleted BM cells (Lin$^-$ cells) from PKD mice (FIG. 2*b*). FIG. 2*a* is a schematic representation of the self-inactivating lentiviral vectors used throughout gene therapy experiments harboring the human PGK promoter regulating the expression of the EGFP transgene in the control vector (upper diagram) or the expression of a codon-optimized sequence of the PKLR gene cDNA (coRPK) in the therapeutic vector (lower diagram). The coRPK sequence showed 80.4% homology with the human PKLR cDNA and 76.5% homology with the mouse Pklr cDNA, with no changes in the amino acid sequence. FIG. 2b is a schematic of the gene therapy protocol performed to address the functionality of the developed PGK-coRPK lentiviral vector. Correction of the PKD phenotype was studied for 4 to 9 months after transplant in PB and BM through hematological analysis and metabolic profiling. Integration analysis was performed in different tissues and time-points from all mice to address LV vector safety. At 280 days post-transplantation, total BM from primary transplanted mice carrying the coRPK transgene was transplanted again into lethally-irradiated female PKD mice (secondary recipients) to test the stability and safety of the engraftment. Lethally irradiated PKD mice transplanted with deficient cells transduced with the coRPK LV showed a significant improvement in all tested blood erythroid parameters when compared to non-transplanted PKD littermates or to mice transplanted with cells transduced with an EGFP LV (FIG. 3 and Table 2).

TABLE 2

Hematological variables recorded 140 days post-transplantation in peripheral blood.

| Group | HGB (g/dL) | HTC (%) | MCV | MCH (pg) |
|---|---|---|---|---|
| Healthy (n = 5) | 14.64 ± 0.99 | 36.15 ± 2.64 | 38.20 ± 0.86 | 15.44 ± 0.21 |
| PKD (n = 9) | 9.70 ± 0.55 | 28.91 ± 1.53 | 51.56 ± 0.50 | 17.23 ± 0.31 |
| EGFP (n = 8) | 6.81 ± 0.68 | 21.32 ± 1.51 | 49.13 ± 0.72 | 15.46 ± 0.62 |
| coRPK n = 17 | 10.67 ± 0.53* | 31.09 ± 1.45* | 45.65 ± 0.84 | 15.35 ± 0.53 |
| 2nd coRPK (n = 4) | 12.40 ± 0.67** | 34.11 ± 1.49* | 46.25 ± 0.85 | 16.78 ± 0.23 |

Data represent the mean±SEM and were statistically analysed by comparison to EGFP-expressing mice using the Kruskal-Wallis non-parametric test. *$p<0.05$; **$p<0.01$.

Figure 3A:
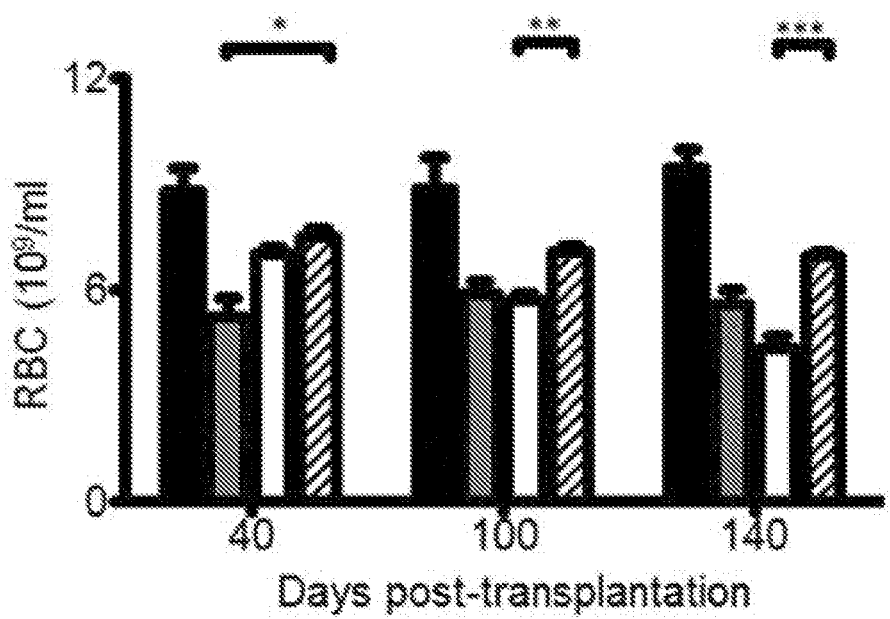
FIGS. 3a-d depict data showing correction of PKD phenotype in peripheral blood of primary recipients after genetic correction.
Figure 3B:
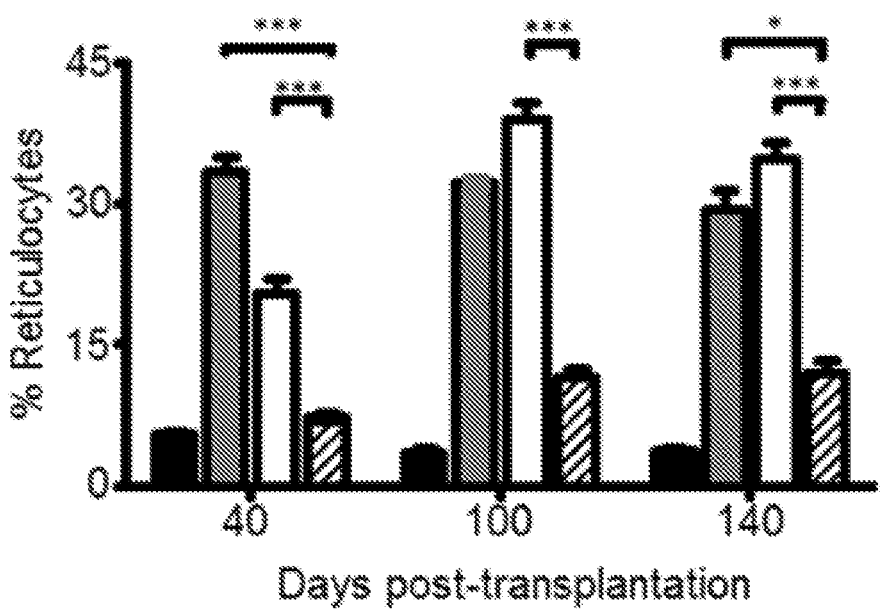

RBC counts increased as soon as 40 days post-transplantation (FIG. 3a) and constitutive reticulocytosis, which is one of the most common signs of PKD, was significantly reverted in mice carrying the PGK-coRPK transgene, reaching levels close to those observed in healthy controls for at least 9 months after transplant (FIG. 3b). On the contrary, PKD animals transplanted with EGFP LV-transduced cells showed anemia and remarkable reticulocytosis in parallel with PKD mice at all time-points analyzed. Hemoglobin levels (HGB), hematocrit index (HTC), mean corpuscular volume (MCV) and mean corpuscular hemoglobin (MCH) values were also corrected in mice transplanted with lentivirally corrected cells when compared to non-transplanted PKD littermates (Table 2). This hematological correction was achieved with 63.66±4.45% of donor chimerism and transduction efficacies ranging from 60% to 90% (Table 3).

TABLE 3

Relevant molecular parameters in mice transplanted with genetically modified cells.

| Assay | Groups | Vector copy number (VCN/cell) | | | Transduction % Provirus[+] | Donor chimerism % SRY[+] |
|---|---|---|---|---|---|---|
| | | WBC | Total BM | CFU | CFUs | PB cells |
| 1 MOI 1-4 | EGFP (n = 2) | .83 ± 0.05 | .42 ± 0.03 | 0.42 ± 0.00 | 57.73 ± 12.28 | n.d |
| | coRPK (n = 3) | .76 ± 0.28 | .58 ± 0.34 | 3.07 ± 0.76 | 91.08 ± 3.67 | n.d |
| 2 MOI 10 | EGFP n = 6 | .56 ± 0.50 | .19 ± 1.29 | 3.93 ± 0.98 | 92.32 ± 7.68 | 61.82 ± 3.61 |
| | coRPK (n = 14) | .65 ± 0.08 | .99 ± 0.13 | 1.89 ± 0.42 | 62.06 ± 11.73 | 63.66 ± 4.45 |
| | 2nd coRPK (n = 4) | .44 ± 0.08 | n.d | n.d | 63.15 ± 0.31[a] | 62.89 ± 5.61 |

Data represent the mean±SEM, n.d, not determined. [a] estimated transduction percentage obtained by interpolation in the linear regression built from experiment 1 (X axis: VCN/WBC, Y axis: % provirus[+] CFUs).

Figure 3C:
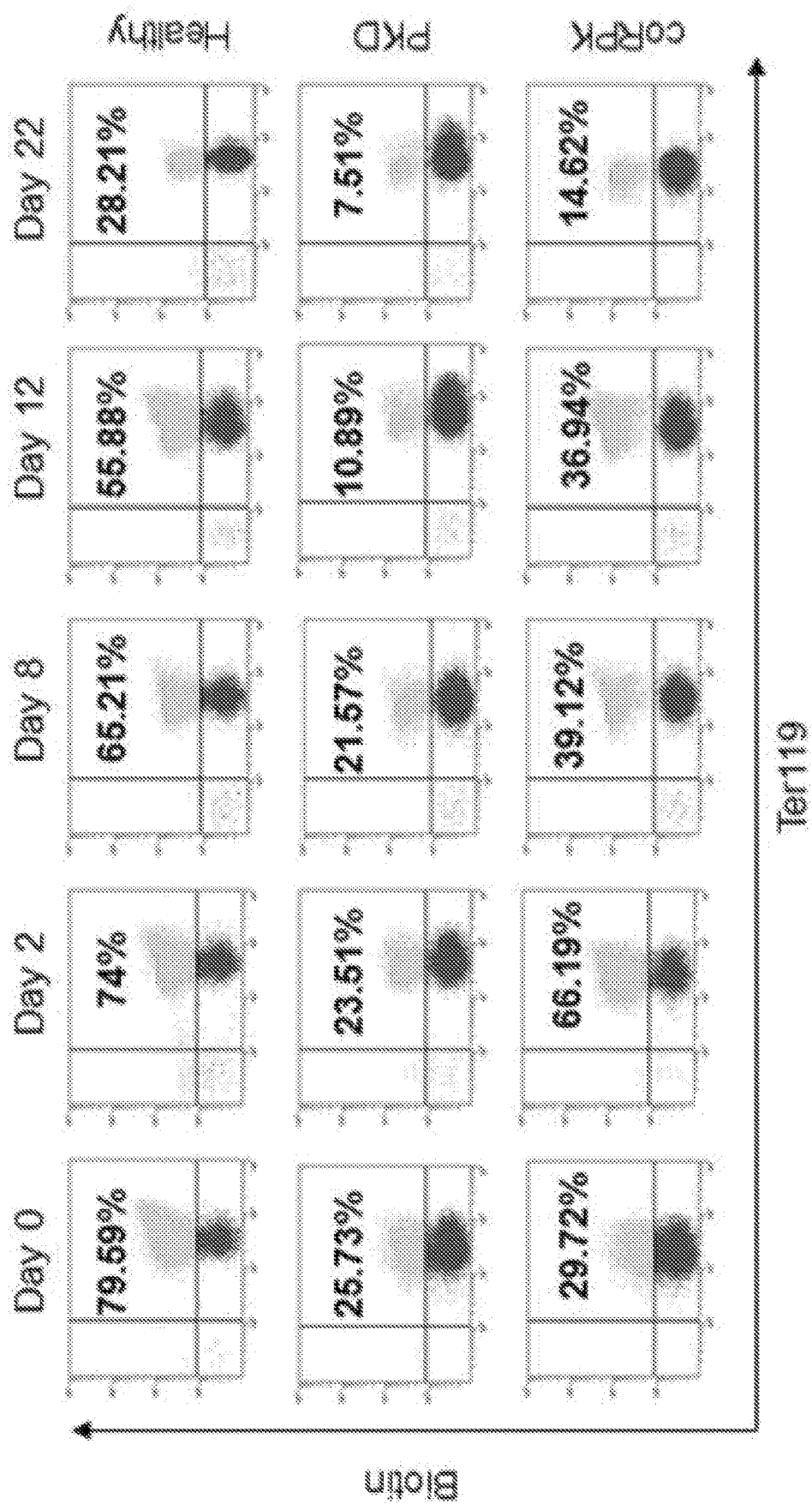
Figure 3D:
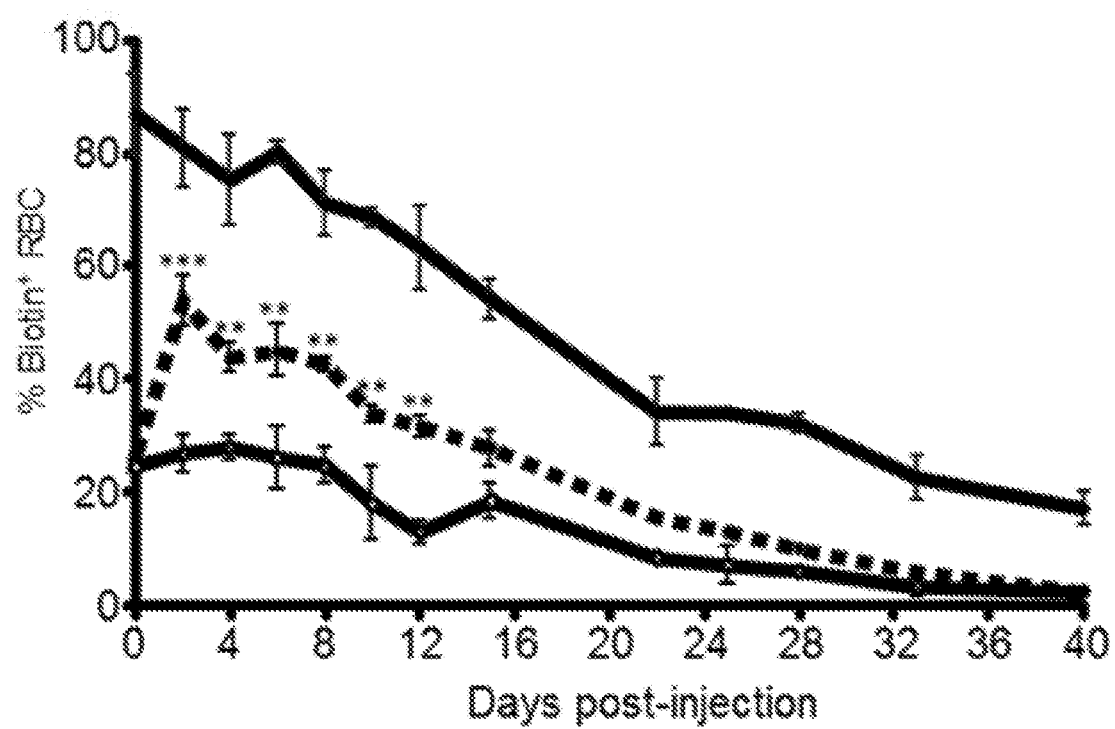

Transduced cells showed on average 1.65±0.08 integrated vector copies per cell, indicating that PGK-coRPK LV-vector provided enough human RPK transgenic expression to revert the hemolytic anemia. Remarkably, the expression of the coRPK transgene led to an extension of erythroid cell half-life when compared to non-transplanted PKD mice (FIGS. 3c,d). On average, PKD mice showed a RBC half-life of 19 days, while in genetically corrected mice this was extended to 25 days (6 days' extension) reaching values close to wild-type RBC half-life (FIG. 3d). Thus, RBCs of coRPK-expressing mice displayed intermediate survival kinetics between healthy and deficient control mice (FIG. 3c), most likely because full chimerism was not achieved in these animals (Table 3).

Figure 4A:
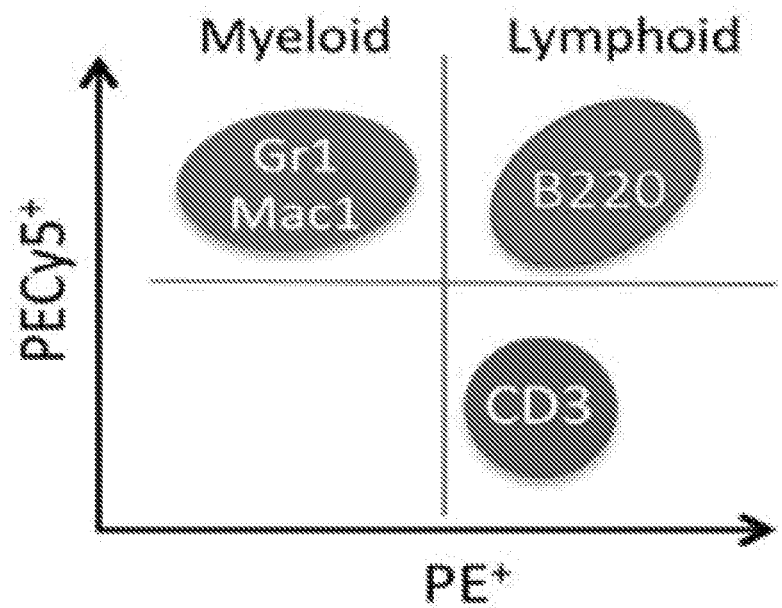
FIGS. 4a-c show multi-lineage hematopoietic reconstitution in secondary transplanted mice.
Figure 4C:
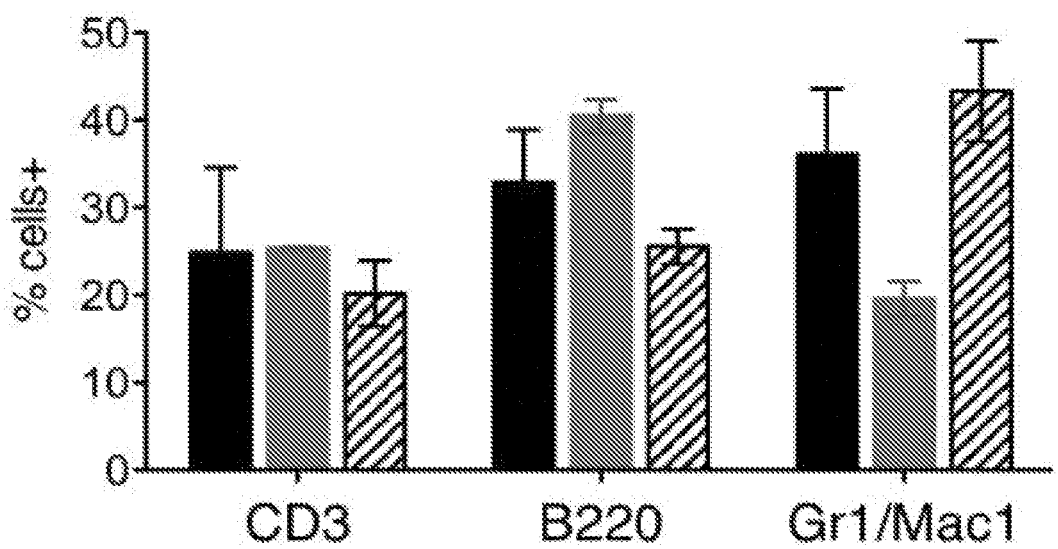
Figure 4B:
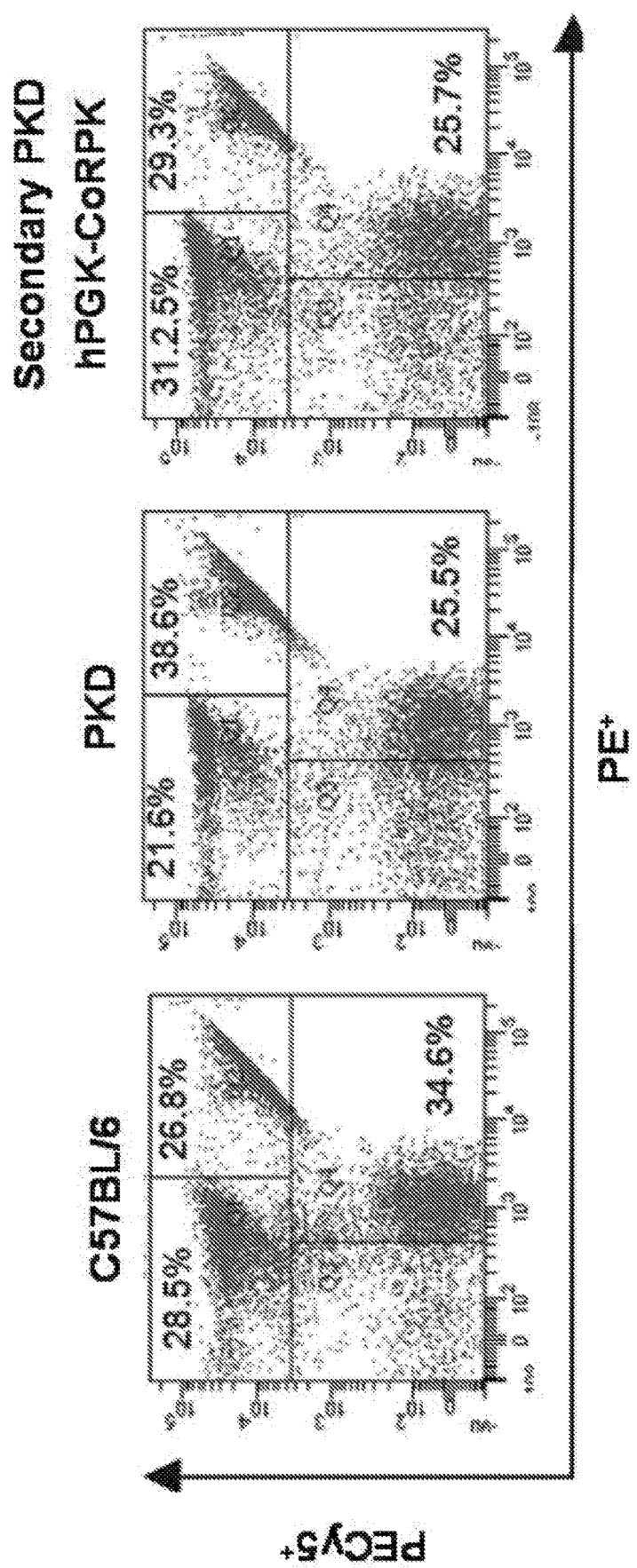
Figure 5A:
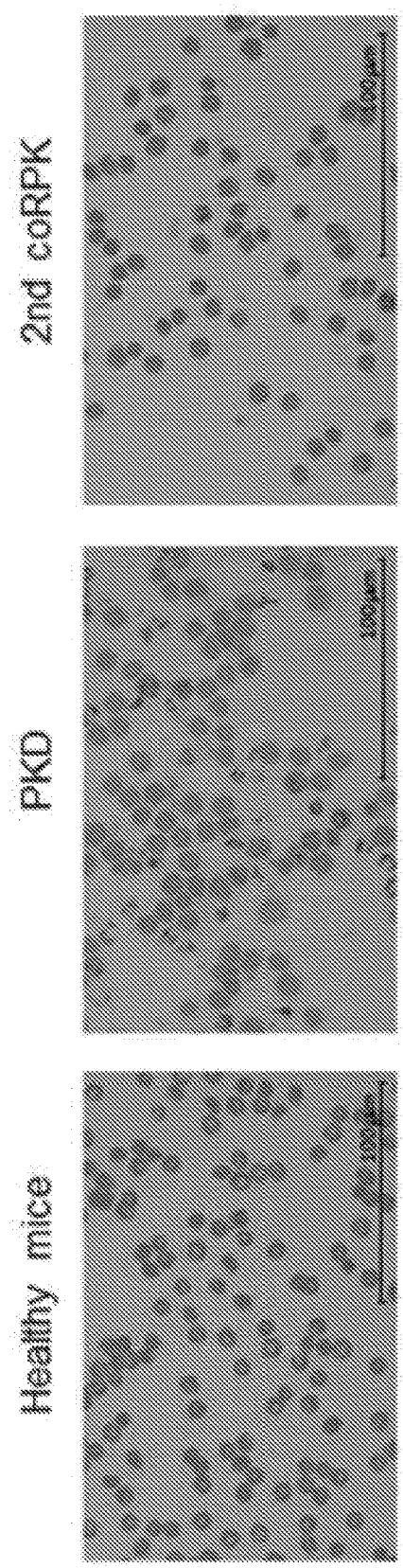
FIGS. 5a-d depict PKD phenotype correction in secondary transplanted mice.
Figure 5B:
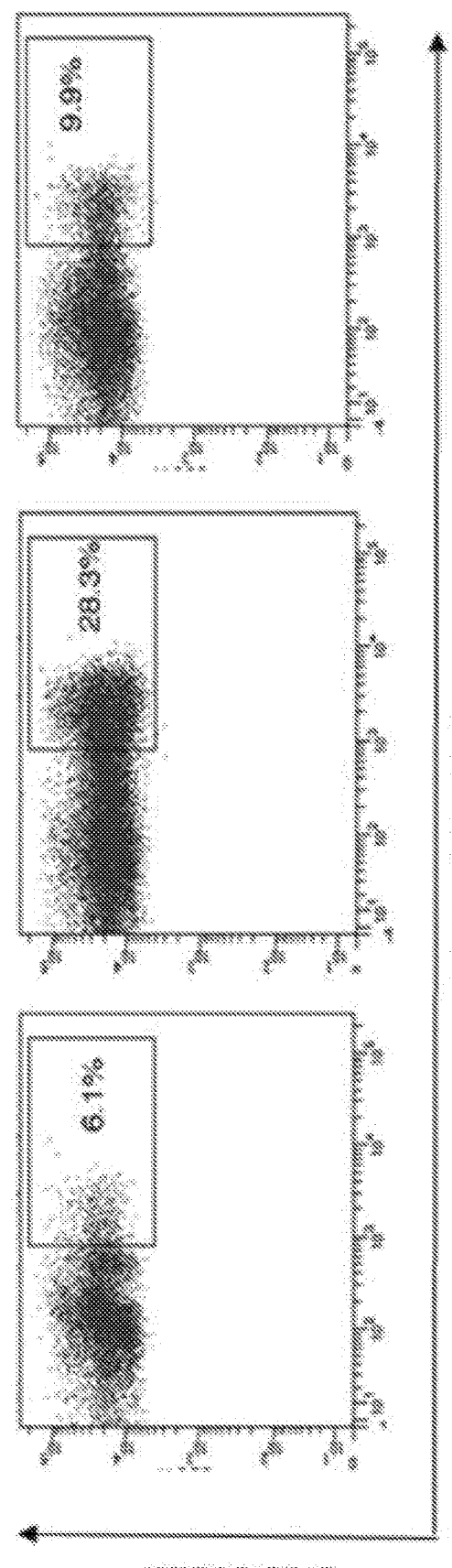
Figure 5D:
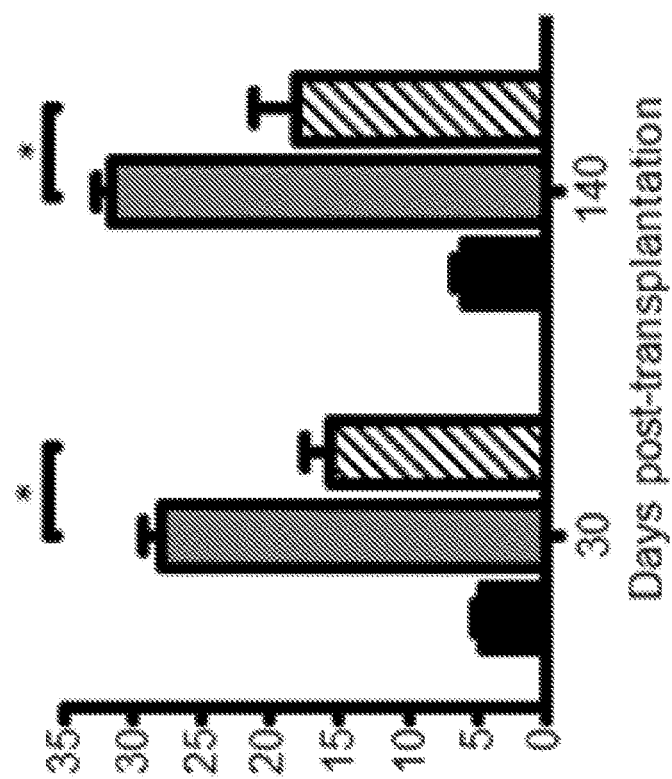
Figure 5C:
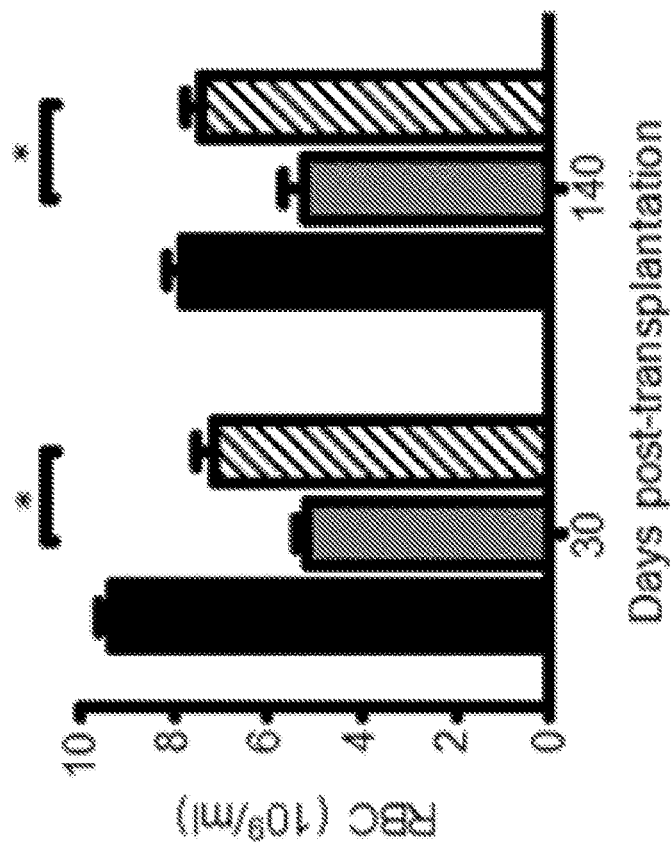
Figure 6A:
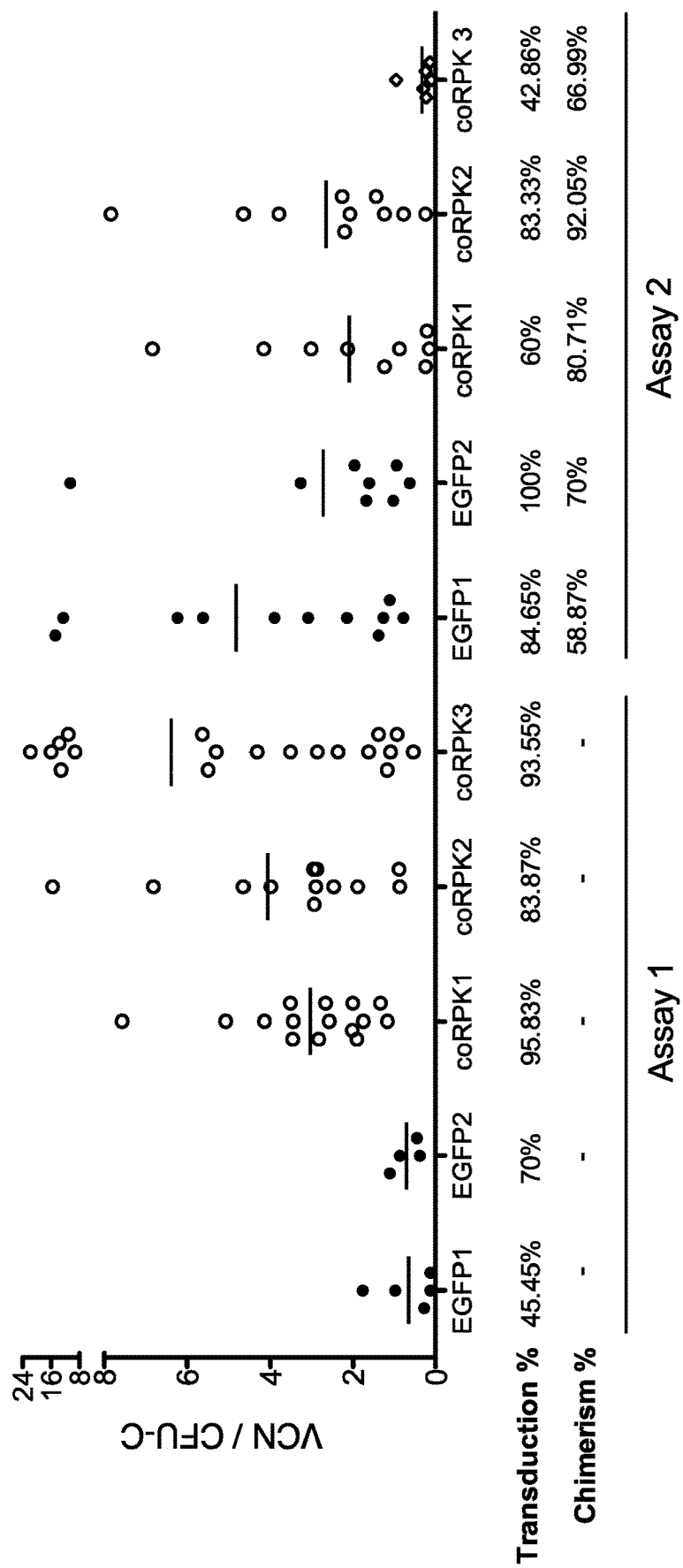
FIGS. 6a-c show quantification of proviral integrations.
Figure 6B:
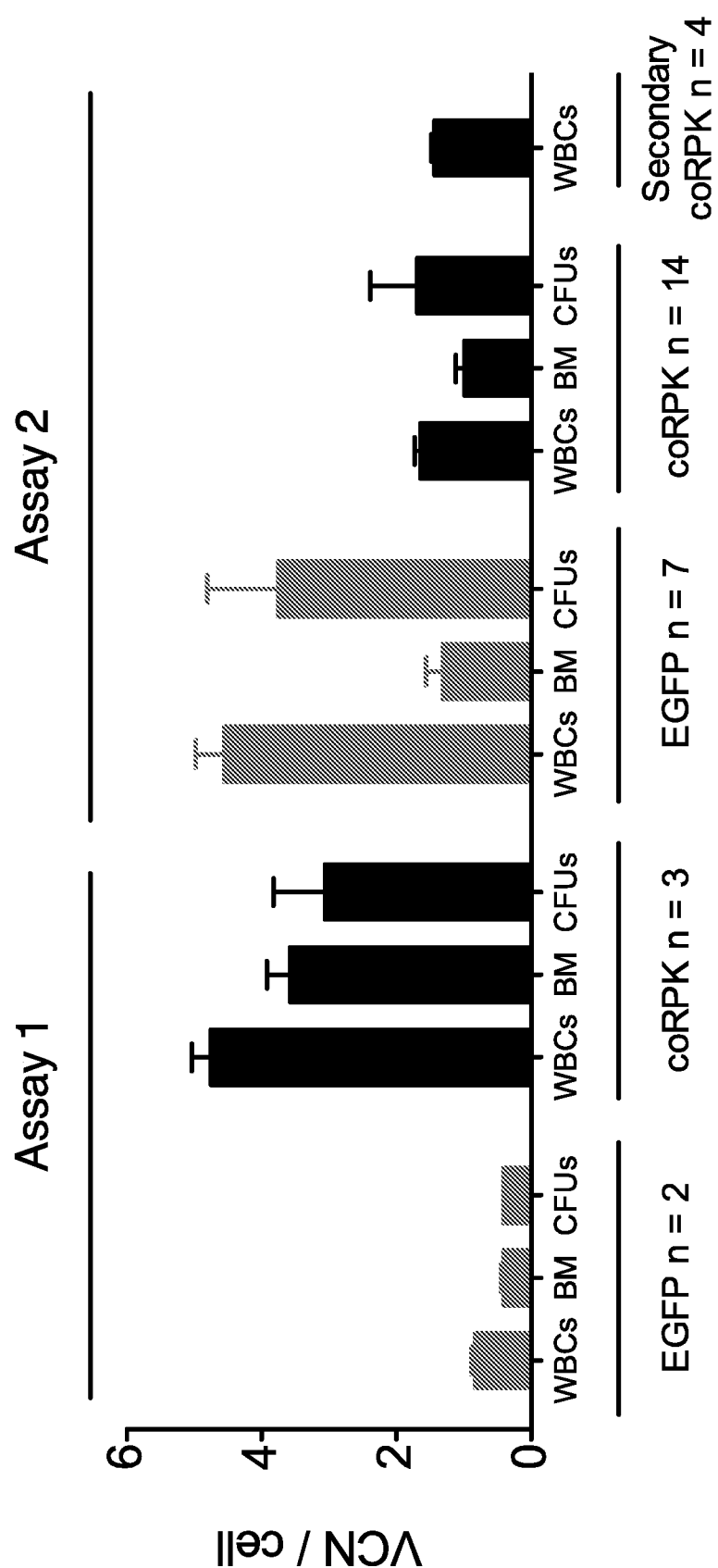
Figure 6C:
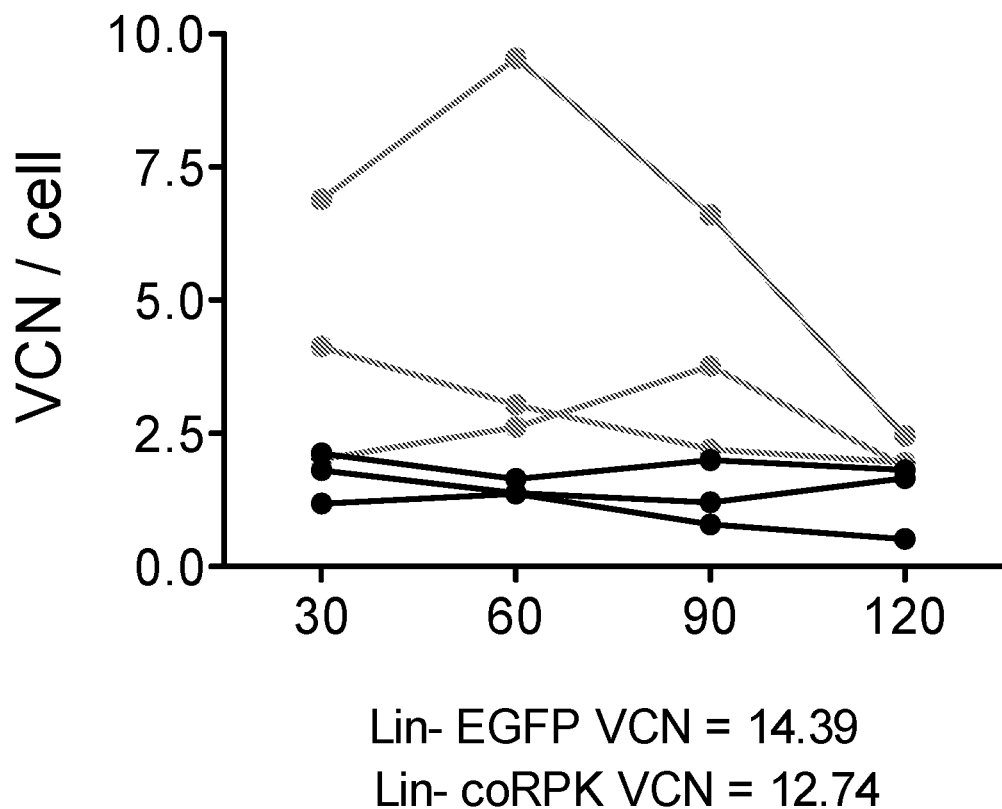

Nine months after transplant hematopoietic progenitors from primary recipients were transplanted into secondary recipients that maintained engraftment levels (62.89±5.61%) and VCN (1.44±0.08 copies) (Table 3). Secondary transplanted recipients showed a multi-lineage hematopoietic reconstitution up to 5 months post-transplantation (FIG. 4) and a significant improvement in all PB erythroid parameters (FIG. 5 and Table 2). FIG. 4a is a diagram of the flow cytometry strategy used to identify the different hematopoietic lineages by labeling with CD3-PE, B220-PE, B220-PECyS, Grl-Biotin and Macl-Biotin antibodies plus SAV-PE-CyS. FIG. 4b depicts representative dot-plots and percentages (FIG. 4c) of each lineage in PB at 140 days after transplant. Bars represent the average percentage±SEM of healthy (n=2, black bar) and PKD mouse (n=2, grey bar) controls and secondary transplanted mice expressing the coRPK therapeutic transgene (n=4, scratched bar). In addition, proviral integrations were detected in differently committed hematopoietic progenitors (FIGS. 6a,b) and its number remained constant over time (FIG. 6c) demonstrating the stability of the genetic correction and highlighting the safety of the PGK-coRPK LV. FIG. 6a shows the vector copy number per cell in BM CFUs from individual transplanted mice at 120 to 170 days after transplant. Transduction and chimerism percentages are also shown. FIG. 6b shows provirus copy number in cells from different hematopoietic compartments. Columns represent the average±SEM of the different groups of transplanted mice. FIG. 6c shows the kinetics of proviral integrations in BM cells from individual transplanted EGFP-expressing mice (grey lines) and mice carrying the coRPK transgene (black lines).

Example 2

Figure 7A:
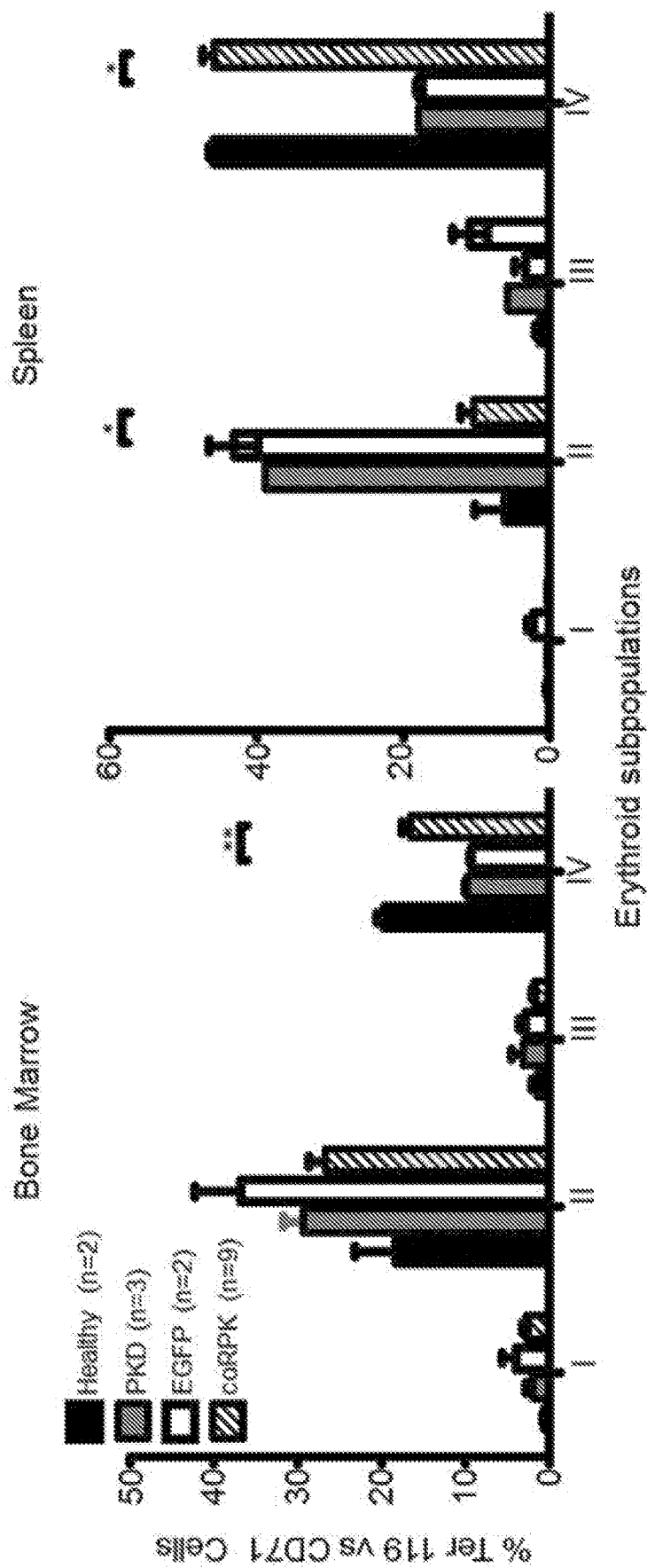
FIGS. 7a-c depict the normalization of the erythroid differentiation pattern in genetically corrected mice.
Figure 7B:
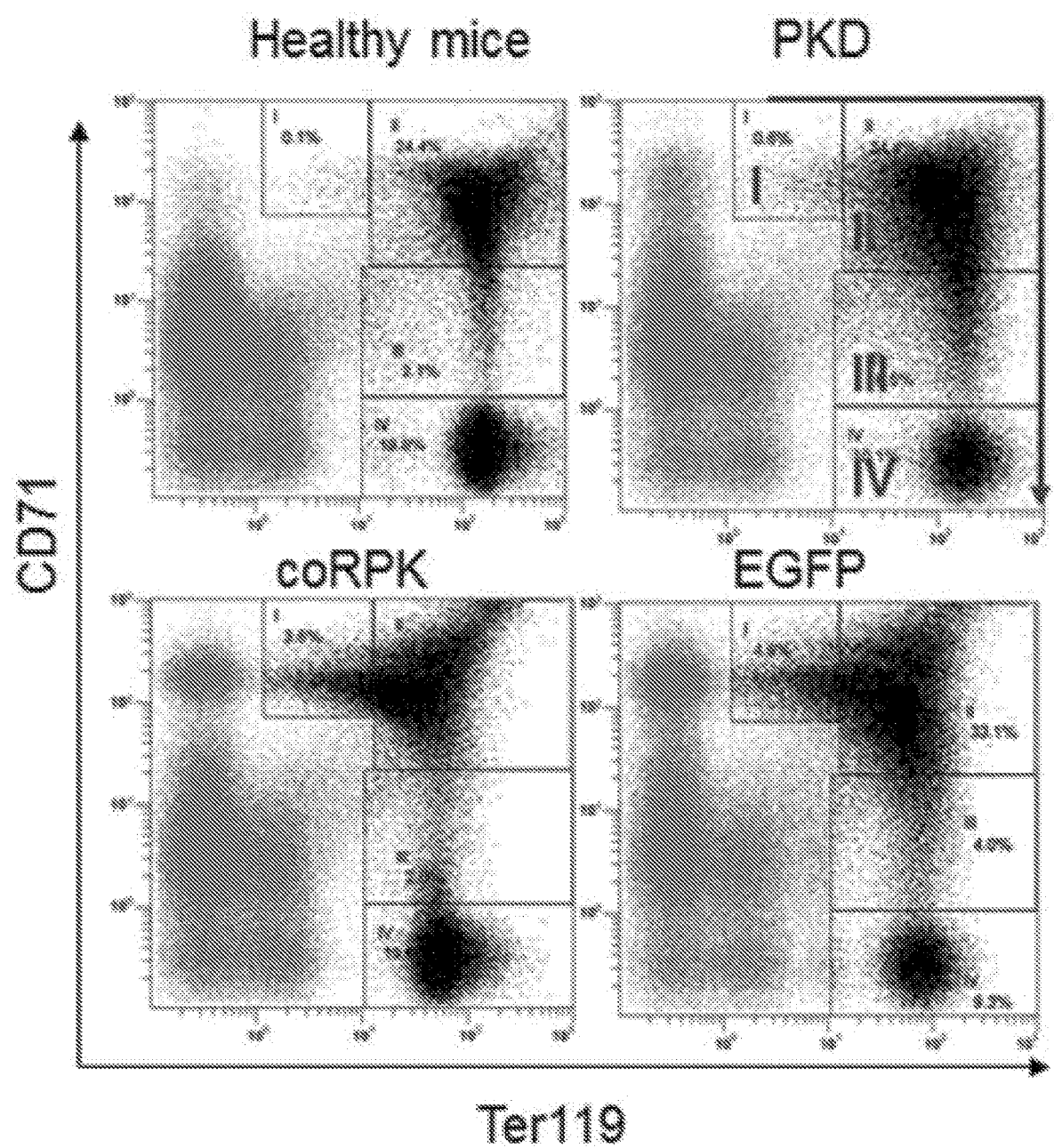
Figure 7C:
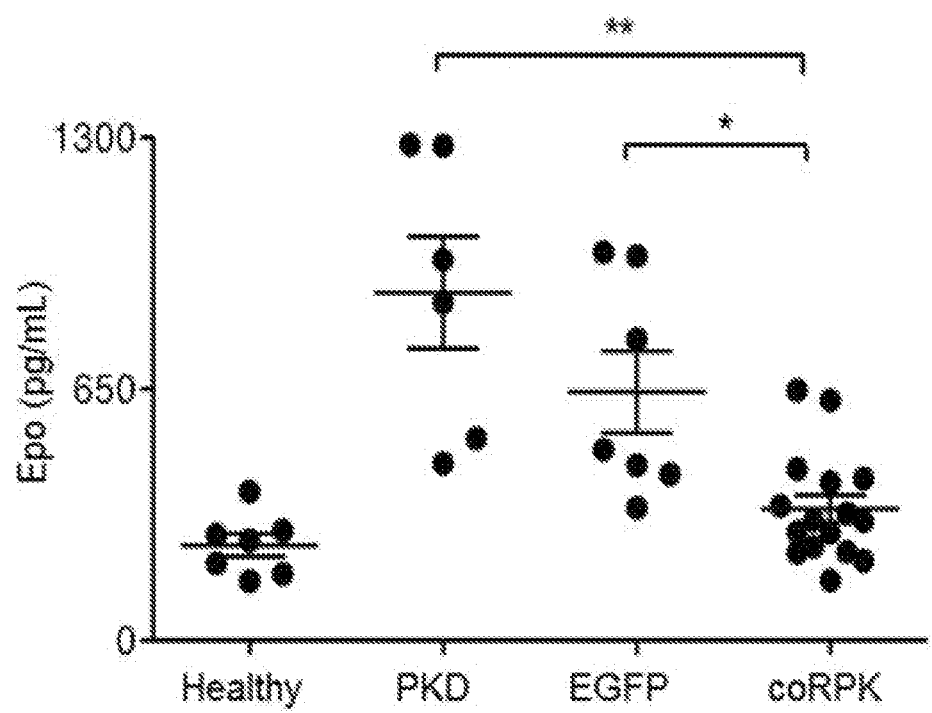
Figures 8A, 8B:
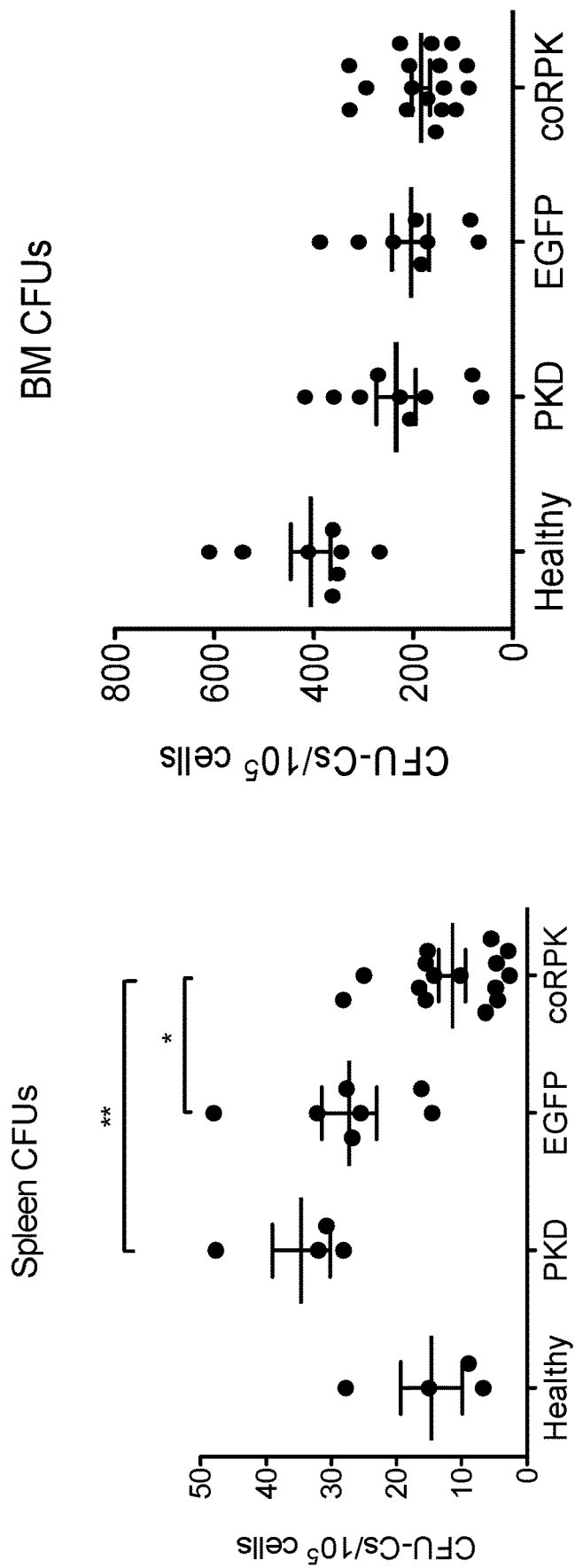
FIGS. 8a-b show hematopoietic progenitor assays in control mice and transplanted mice with transduced cells. The data demonstrate total CFUs from spleen (FIG. 8a) and bone marrow (FIG. 8b) at 140 days after transplant. Dots represent number of colonies per mouse analyzed and lines represent average±SEM in each group. Data were statistically analyzed by non-parametric Kruskal-Wallis test.

Lentiviral-Derived RPK Expression Normalizes Erythroid Differentiation and Allows the Production of Functional Mature Erythrocytes PKD mice show a characteristic expansion of the erythroid compartment caused by the compensatory erythropoiesis mechanism (Min-oo et al 2004). The study of the erythroid differentiation pattern in transplanted mice indicated that the ectopic RPK expression reverted this mechanism (FIGS. 7a,b). PKD and EGFP-expressing mice showed a predominance of immature erythroid precursors (subpopulation I: proerythroblasts and subpopulation II: basophilic erythroblasts) in BM and spleen, and a remarkable fall in late erythroid cells (population IV: reticulocytes and mature erythrocytes), while mice transplanted with cells transduced with the coRPK LV showed a significant reduction of immature erythroid precursors (subpopulations I and II) in BM and spleen, and a significant increase of the latest erythroid compartment (subpopulation IV) equivalent to healthy mice (FIGS. 7a,b). In addition, unlike PKD and EGFP-expressing mice, those carrying the coRPK transgene showed a significant reduction of erythropoietin (Epo) levels in plasma (FIG. 7c). FIG. 8a shows the total CFUs from spleen and FIG. 8b shows the bone marrow at 140 days after transplant. Dots represent number of colonies per mouse analyzed and lines represent average±SEM in each group. Data were statistically analyzed by non-parametric Kruskal-Wallis test. The normalization of the erythropoiesis in PKD mice treated with the therapeutic vector was accompanied by a reduction of the splenic number of progenitors content to normal levels (FIG. 8a), although no changes in the BM CFU content were noted (FIG. 8b).

Example 3

Figure 9A:
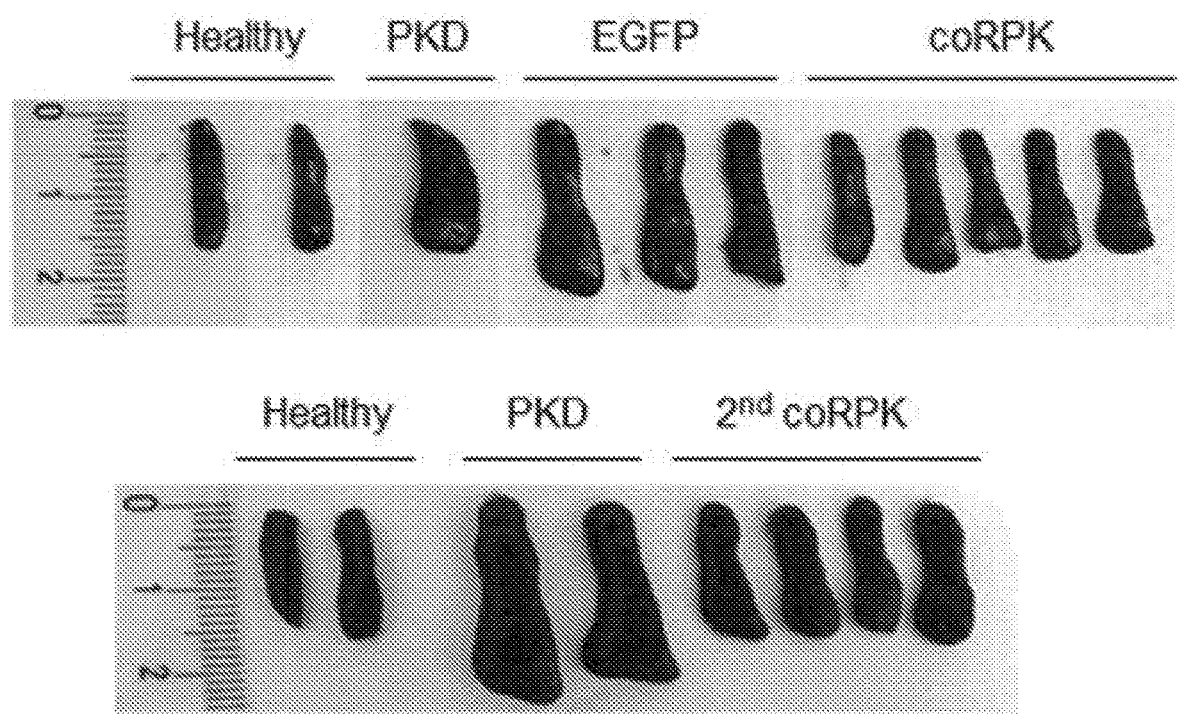
FIGS. 9a-c demonstrate reversion of splenomegaly and organ pathology in genetically corrected mice at 140 days post-transplantation.
Figure 9B:
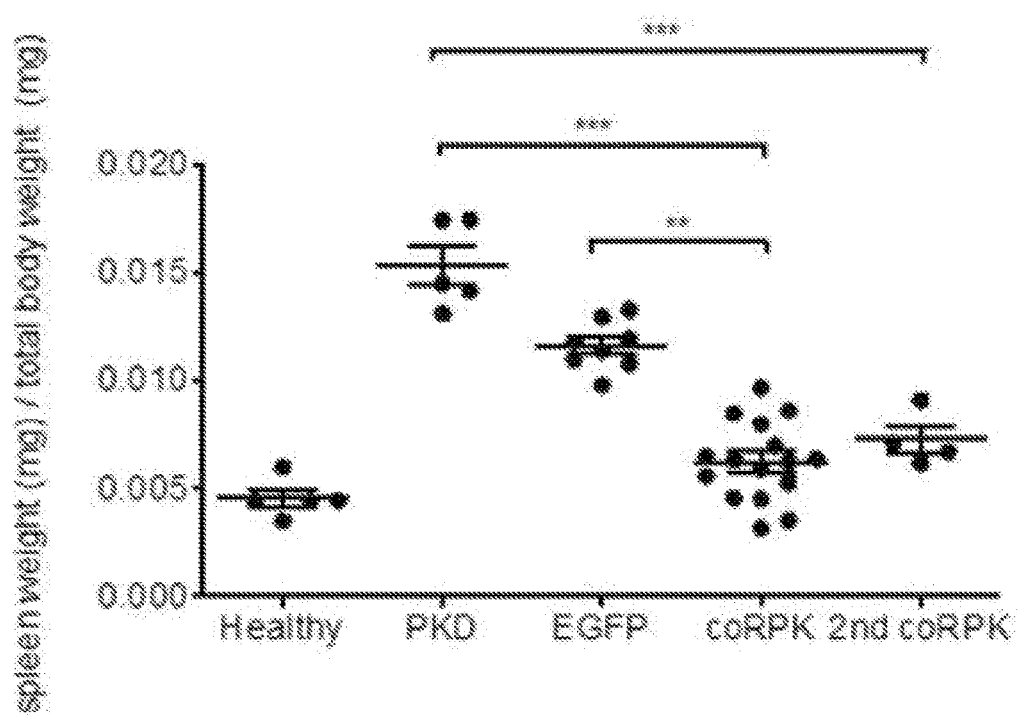
Figure 9C:
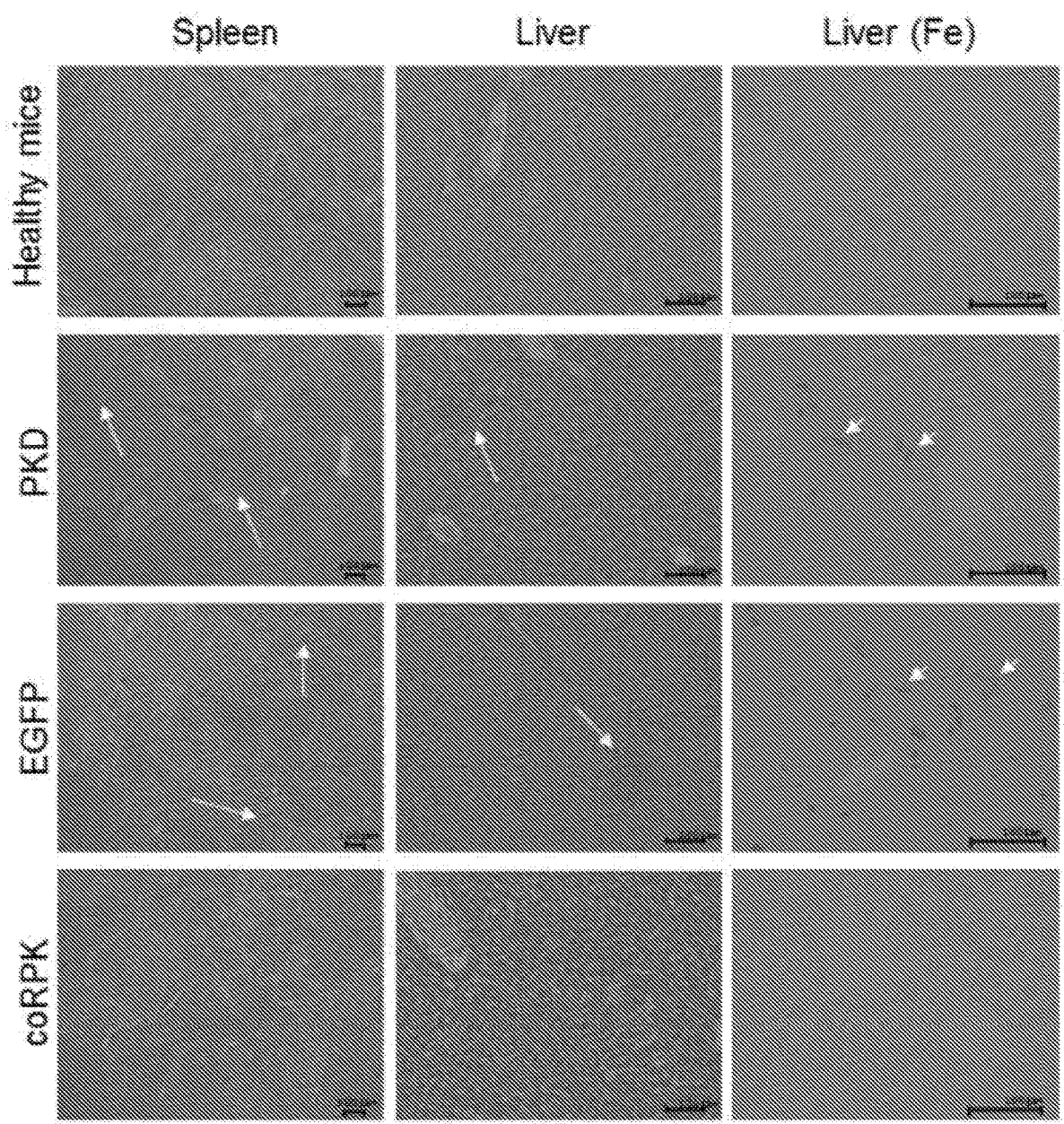

Transplantation of Cells Transduced with the coRPK Lentiviral Vector Reverts Extramedullar Erythropoiesis and Organ Pathology Due to the active destruction of RPK deficient erythrocytes, PKD and EGFP-expressing mice displayed acute splenomegaly with an increase of spleen weight and size of over 200% when compared to healthy controls (FIGS. 9a,b). A disorganized structure of the splenic tissue and the expansion of the spleen red pulp were also observed in these animals, indicating an intense extramedullar erythropoiesis also supported by the presence of erythroid cell clusters in PKD and EGFP-expressing liver sections (FIG. 9c). Remarkably, the ectopic expression of coRPK transgene completely reverted spleen and liver pathology in genetically corrected mice, reducing the RBC accumulations and normalizing spleen histological structure and size (FIG. 9). Additionally, histological studies revealed the total absence of iron deposits in the liver of genetically corrected mice, whereas PKD mice either from the non-transplanted group or the group transplanted with HSCs transduced with the EGFP-carrying vector displayed an intense iron overload due to the continuous hemolytic process (FIG. 9c). Overall, the transplant of genetically corrected HSCs in PKD mice restored the normal status of the erythropoiesis and all the secondary effects caused by the hemolytic anemia.

Example 4

Figure 10A:
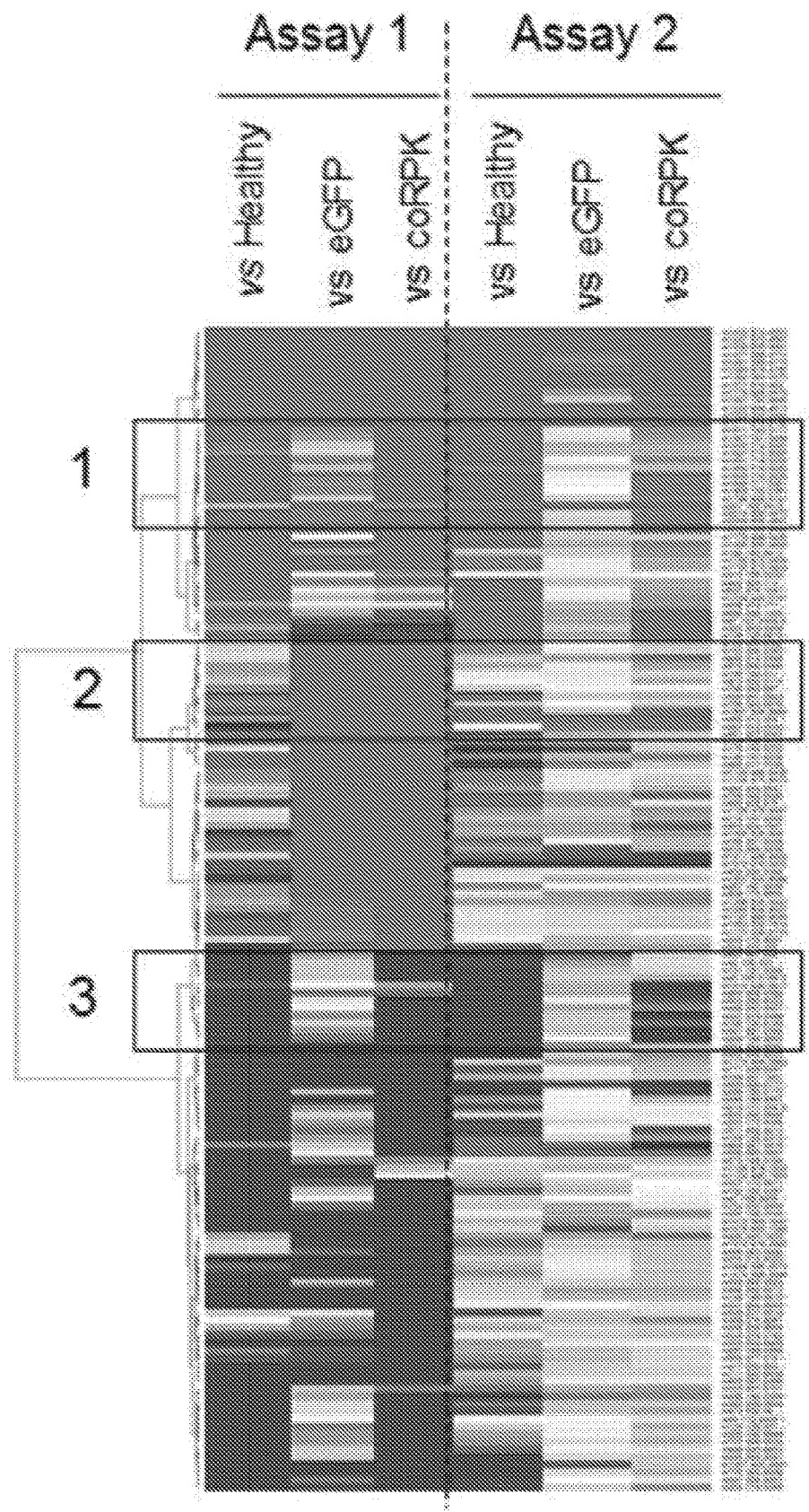
FIGS. 10a-g depict metabolic profiling in RBC samples from mice transplanted with genetically modified cells. Analysis of significant metabolic profile changes in healthy and transplanted mice by comparison to PKD animals in two independent experiments.
Figure 10B:
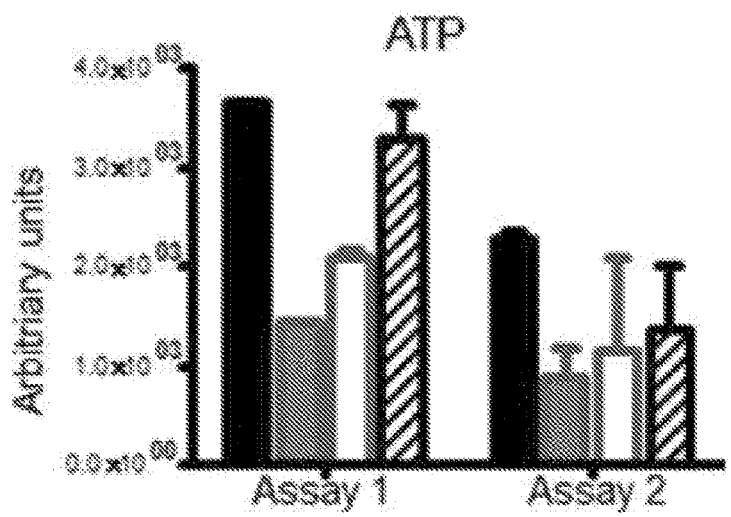
Figure 10C:
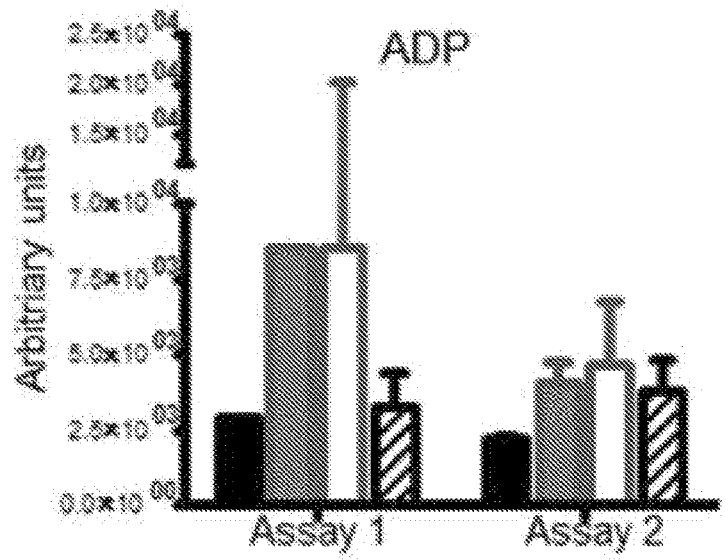
Figure 10D:
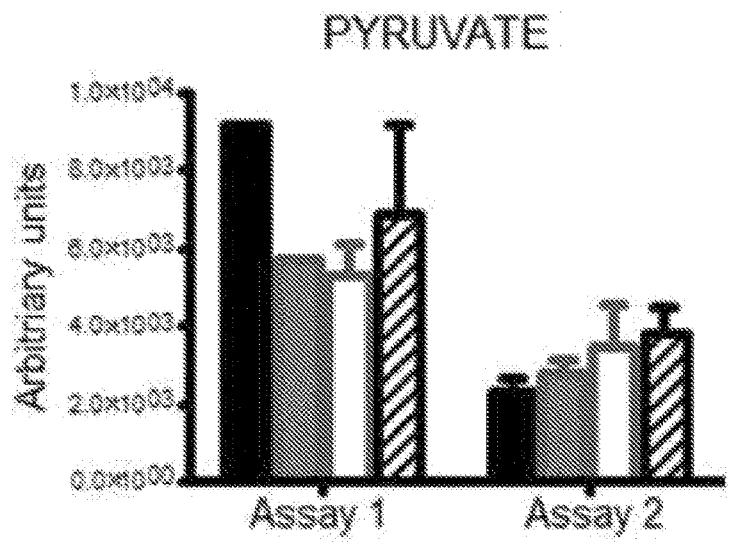
Figure 10E:
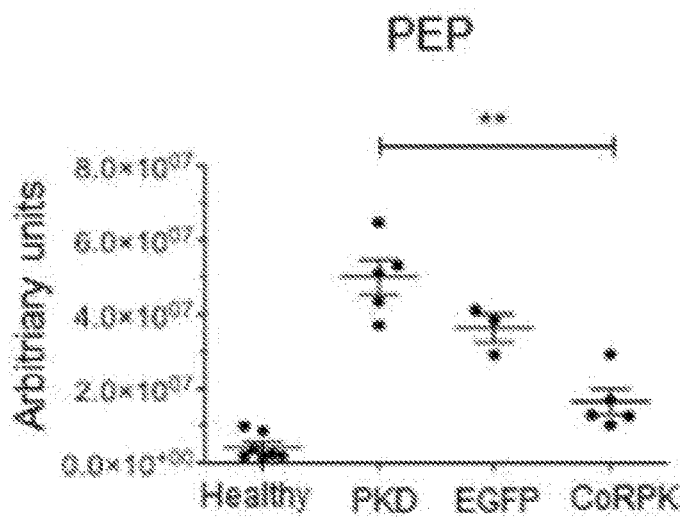
Figure 10F:
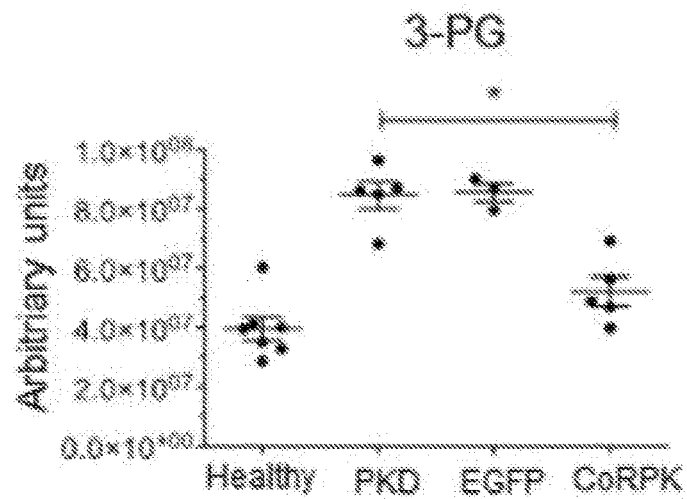
Figure 10G:
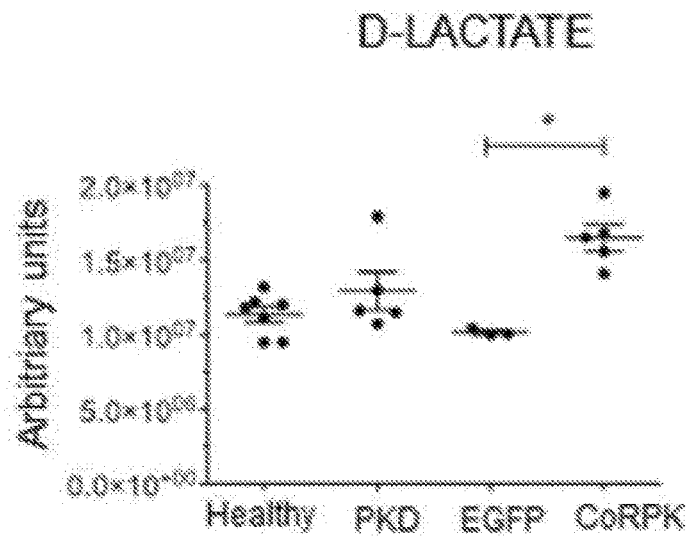
Figure 11B:
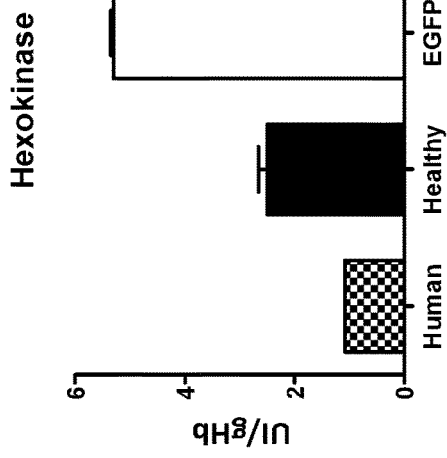
FIGS. 11a-c depict pyruvate Kinase activity, FIG. 11b hexokinase activity and FIG. 11c ratio of Pyruvate Kinase and Hexokinase enzymatic activities in RBCs from control mice and mice transplanted with transduced cells. RBCs were purified from blood samples through a cellulose column to avoid leukocyte PK activity contamination and subjected to enzyme activity evaluation. Black bars, healthy mice (n=2); white bars, mice transplanted with cells transduced with the EGFP expressing vector (n=3); scratched bars, mice transplanted with cells transduced with the coRPK expressing vector (n=3). Checkered bars represent values from a healthy volunteer (n=1). Data represent the average±SEM of each group.
Figure 11A:
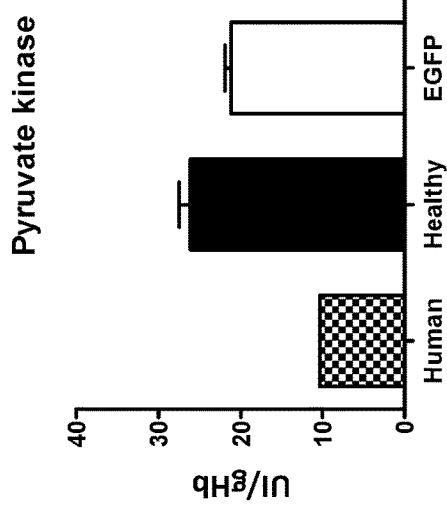
Figure 11C:
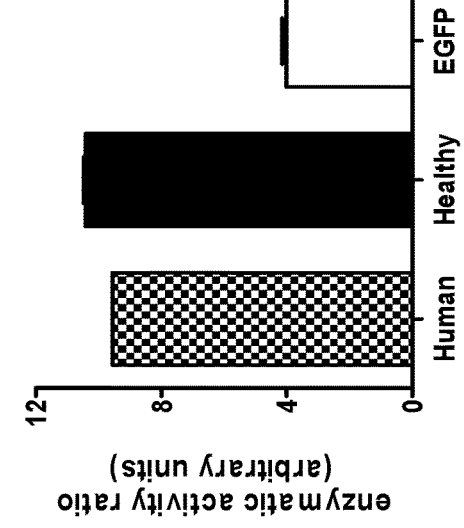

PGK-coRPK LV-Derived Expression Restores the Glycolysis Pathway in RBCs without Modifying the WBC Metabolic Balance Next, we performed an extensive metabolomic analysis of all transplanted and control mice to study the functional correction of RPK enzymatic activity. Following an untargeted profiling strategy, we observed significant changes of glycolytic intermediates in RBCs among the different groups, identifying three broad clusters of metabolite patterns with distinct trends (FIG. 10a). RBCs from coRPK-expressing mice showed an increase of metabolites from cluster 1 similar to healthy controls but different from transplanted mice carrying the EGFP transgene. Likewise, cluster 3 reflected a reduced metabolite trend in genetically corrected mice similar to wild type mice and different from EGFP-expressing mice. Nevertheless, cluster 2 from assay 1 showed no differences of metabolite profile between transplanted mouse groups (EGFP and coRPK expressing mice) (FIG. 10a). The untargeted metabolic profiling also showed that the genetic modification was capable of modifying some important glycolytic intermediates, achieving an increase in ATP (FIG. 10b), ADP (FIG. 10c) and pyruvate (FIG. 10d) levels in erythrocytes isolated from mice transplanted with PGK-coRPK LV-transduced HSCs. Considering these metabolic trends, we then analysed other metabolites located closer to the PK-catalysed reaction using a targeted profiling approach. Levels of the direct PK substrate phosphoenolpyruvate (PEP) (FIG. 10e) and the 3-phosphoglycerate (3-PG) (FIG. 10f), located upstream of the PK-catalysed reaction, approached to that of healthy control mice. Deficient erythrocytes expressing the coRPK transgene also produced an increase of D-lactate (FIG. 10g), the final product of the anaerobic glycolysis, when compared to PKD and EGFP expressing mice. To test whether the compensation in the glycolytic metabolites was a result of the normalization in the PK activity in mature erythrocytes, we measured the activity of this enzyme and normalized it in relation to the Hexokinase activity in order to avoid the influence of high amounts of reticulocytes in the deficient animals. RBCs were purified through a cellulose column to prevent leukocyte PK activity contamination. A complete compensation of PK activity was observed in the animals expressing the coRPK that reach ratios similar to those obtained from wild type healthy animals and from a normal healthy blood donor volunteer (FIG. 11). FIG. 11a shows Pyruvate Kinase activity, FIG. 11b shows Hexokinase activity and FIG. 11e shows ratio of Pyruvate Kinase and Hexokinase enzymatic activities in RBCs from control mice and mice transplanted with transduced cells. RBCs were purified from blood samples through a cellulose column to avoid leukocyte PK activity contamination and subjected to enzyme activity evaluation. Black bars, healthy mice (n=2); white bars, mice transplanted with cells transduced with the EGFP expressing vector (n=3); scratched bars, mice transplanted with cells transduced with the coRPK expressing vector (n=3). Checkered bars represent values from a healthy volunteer (n=1). Data represent the average±SEM of each group.

Figure 12A:
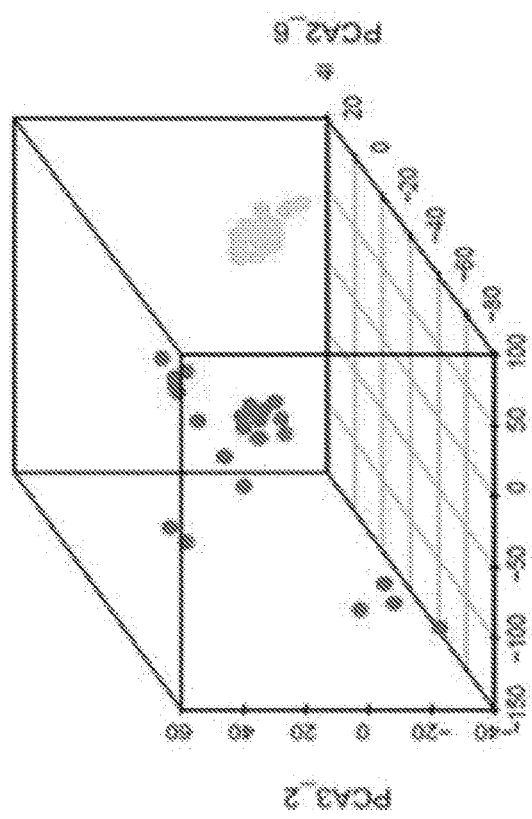
FIGS. 12a-d show untargeted metabolic profiling in WBC samples from mice transplanted with genetically modified cells.
Figure 12B:
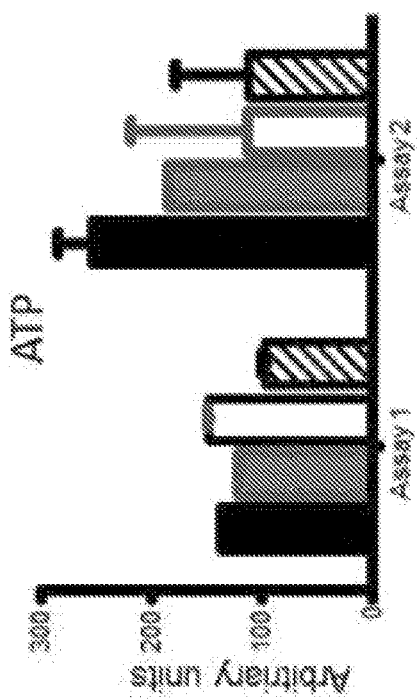
Figure 12C:
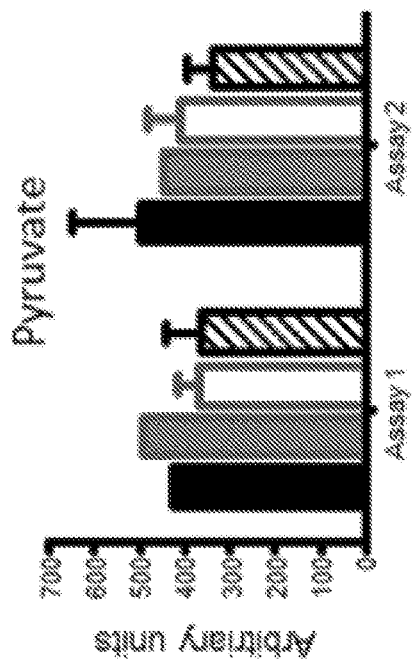
Figure 12D:
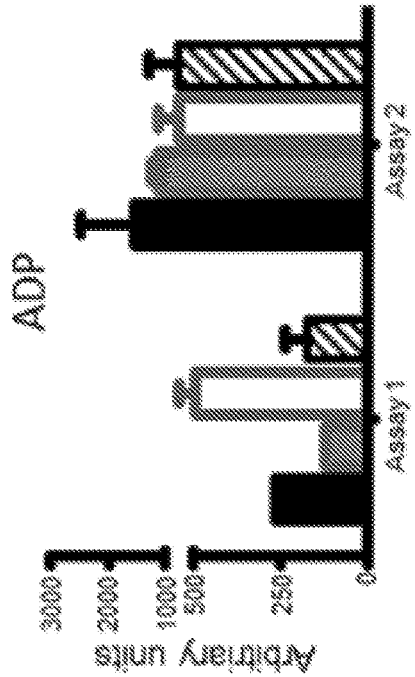

Principal component analysis showed that metabolite pattern of RBCs was different depending on the group and markedly different to WBC profile (FIG. 12a). On the contrary, WBC sub-groups clustered together with very little difference among groups, indicating no changes in the metabolic balance of leukocytes when expressing the ectopic coRPK (FIG. 12a). Additionally, specific metabolite changes observed in the RBC untargeted profiling were not present in WBCs (FIGS. 12b-d).

Example 5

Figure 13:
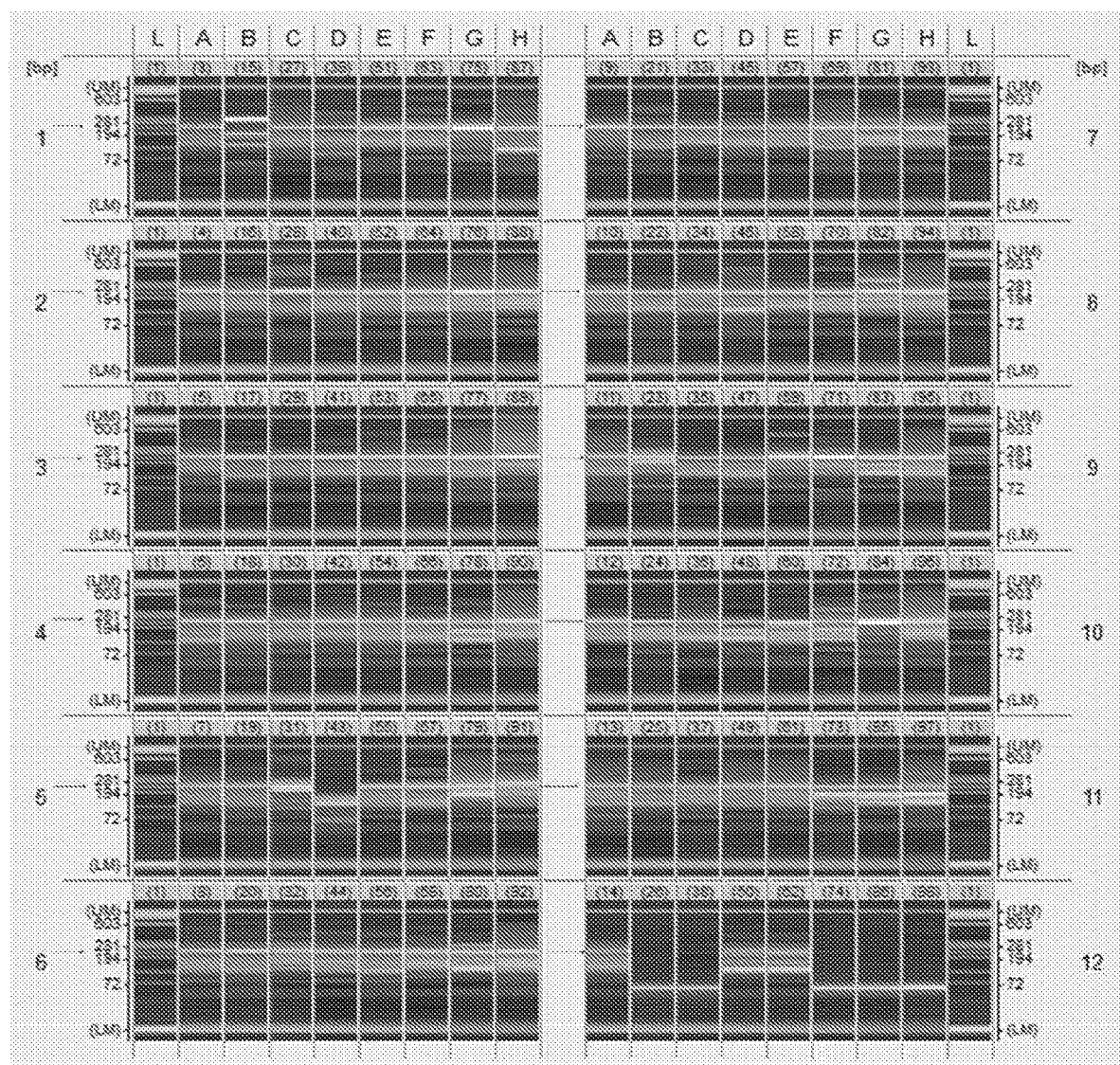
FIG. 13 shows a gel image of LAM-PCR products generated with Tsp5091 enzyme for samples harvested from all mice at different time points and tissues. Vector integration sites were identified by LAM-PCR amplification of 3'vector LTR-genome junctions. A MultiNA automated system was used, generating a pattern characterized by several bands. Vector backbone derived Tsp5091 internal control band (IC) is indicated by an arrow.
Figure 14:
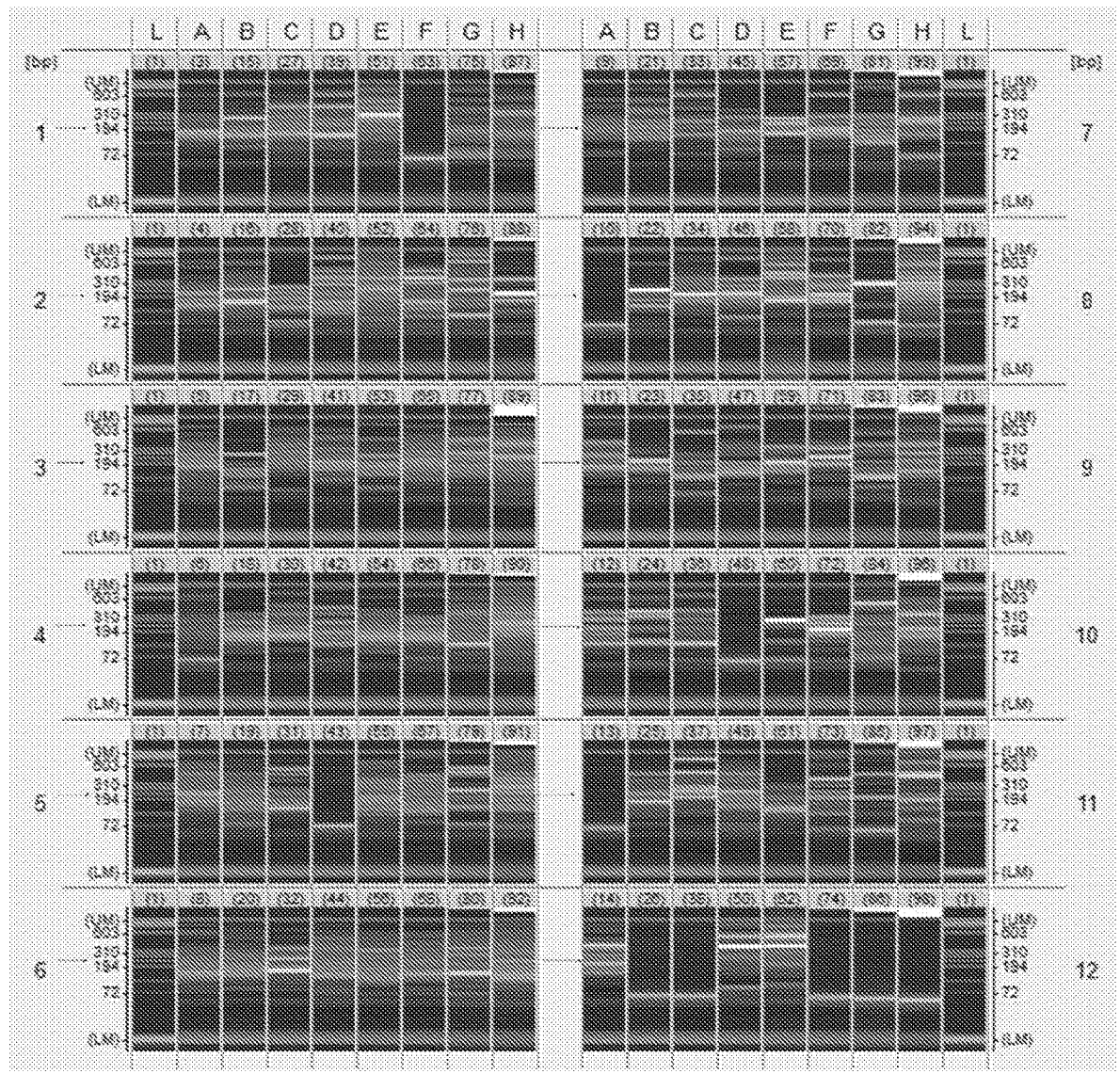
FIG. 14 shows a gel image of LAM-PCR products generated with HpyCH4IV5 enzyme for samples harvested from all mice at different time points and tissues. Vector integration sites were identified by LAM-PCR amplification of 3' vector LTR-genome junctions. A MultiNA automated system was used, generating a pattern characterized by several bands. Vector backbone derived HpyCH4IV5 internal control band (IC) is indicated by an arrow.

PGK-coRPK LV Transduced Cells Render Polyclonal Hematopoietic Reconstitution without Evidence of Vector Genotoxicity Integration profile of LVs carrying either the coRPK or the EGFP transgene was analysed in transplanted mice. Resulting from the genome-wide integration profile of LVs, each insertion creates a unique genetic mark that can be used to track the clonal behaviour in individual transduced cells. Genomic DNA (gDNA) was obtained from WBCs and from BM cells and from primary and secondary transplanted mice, as well as from transduced cell pools before transplant (Lin cells). Linear Amplification Mediated PCR (LAM-PCR) (FIGS. 13 and 14) was used to amplify vector/genome junctions, and to identify vector insertion sites (ISs). FIG. 13 demonstrates vector integration sites were identified by LAM-PCR amplification of 3'vector LTR-genome junctions. A MultiNA automated system was used, generating a pattern characterized by several bands. Vector backbone derived Tsp509I internal control band (IC) is indicated by an arrow. FIG. 14 demonstrates vector integration sites were identified by LAM-PCR amplification of 3' vector LTR-genome junctions. A MultiNA automated system was used, generating a pattern characterized by several bands. Vector backbone derived HpyCH4IV5 internal control band (IC) is indicated by an arrow.

Figure 15:
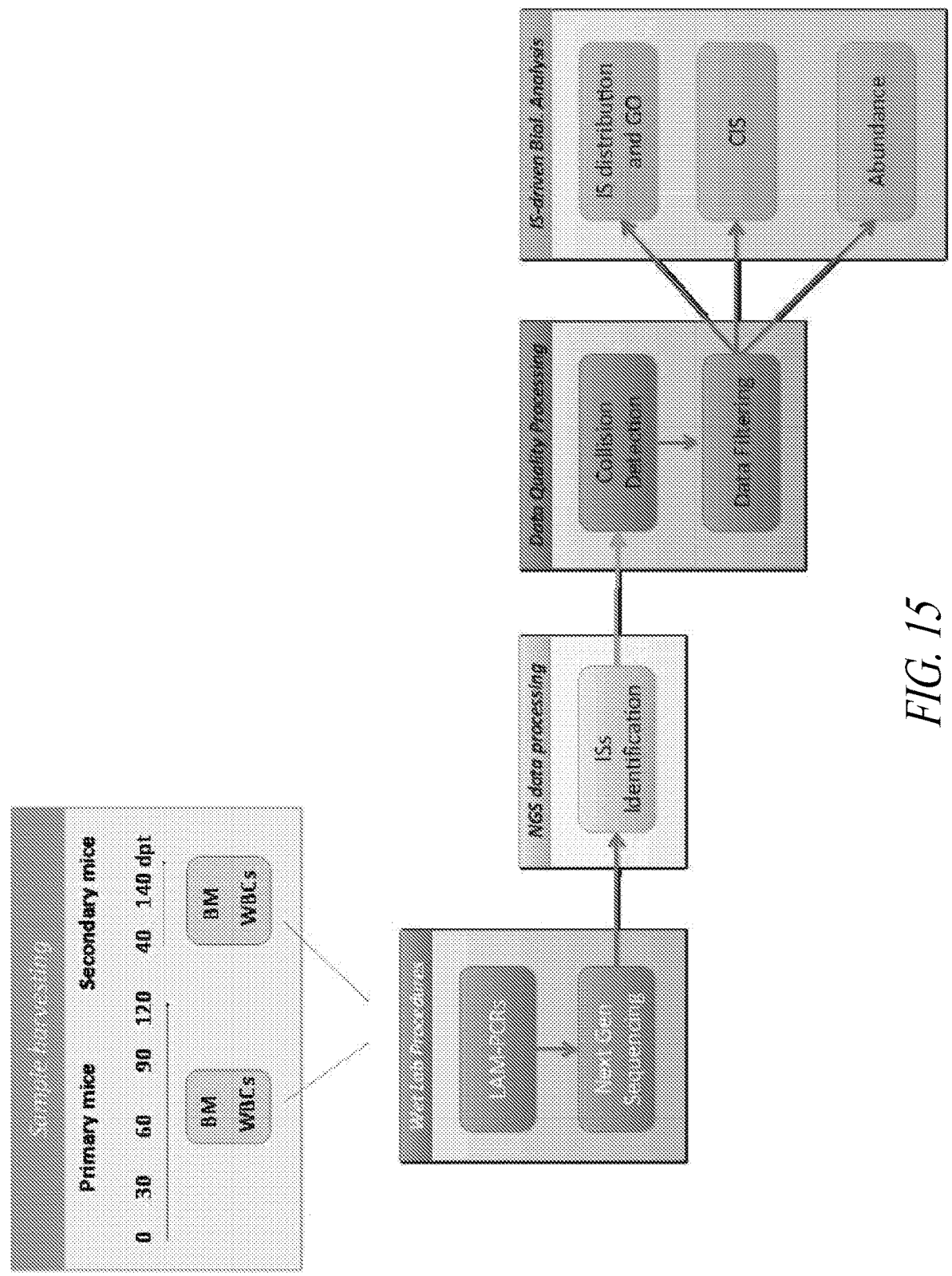
FIG. 15 depicts a general scheme of the analysis of integration site mapping performed in mice transplanted with genetically modified hematopoietic progenitors. Bone marrow and white blood cell samples from transplanted mice belonging to two independent experiments (Table 3) and harvested at different time-points after transplant were analyzed as described in supplementary methods following the showed pipeline.

PCR products were sequenced by MiSeq Illumina platform and the obtained sequences were mapped onto the mouse genome by bioinformatics pipeline and filtered for collisions as described in the Methods section above (FIG. 15). FIG. 15 is the general scheme of the analysis of integration site mapping performed in mice transplanted with genetically modified hematopoietic progenitors. Bone marrow and white blood cell samples from transplanted mice belonging to two independent experiments (Table 3) and harvested at different time-points after transplant were analyzed as described in supplementary methods following the showed pipeline.

Figure 16A:
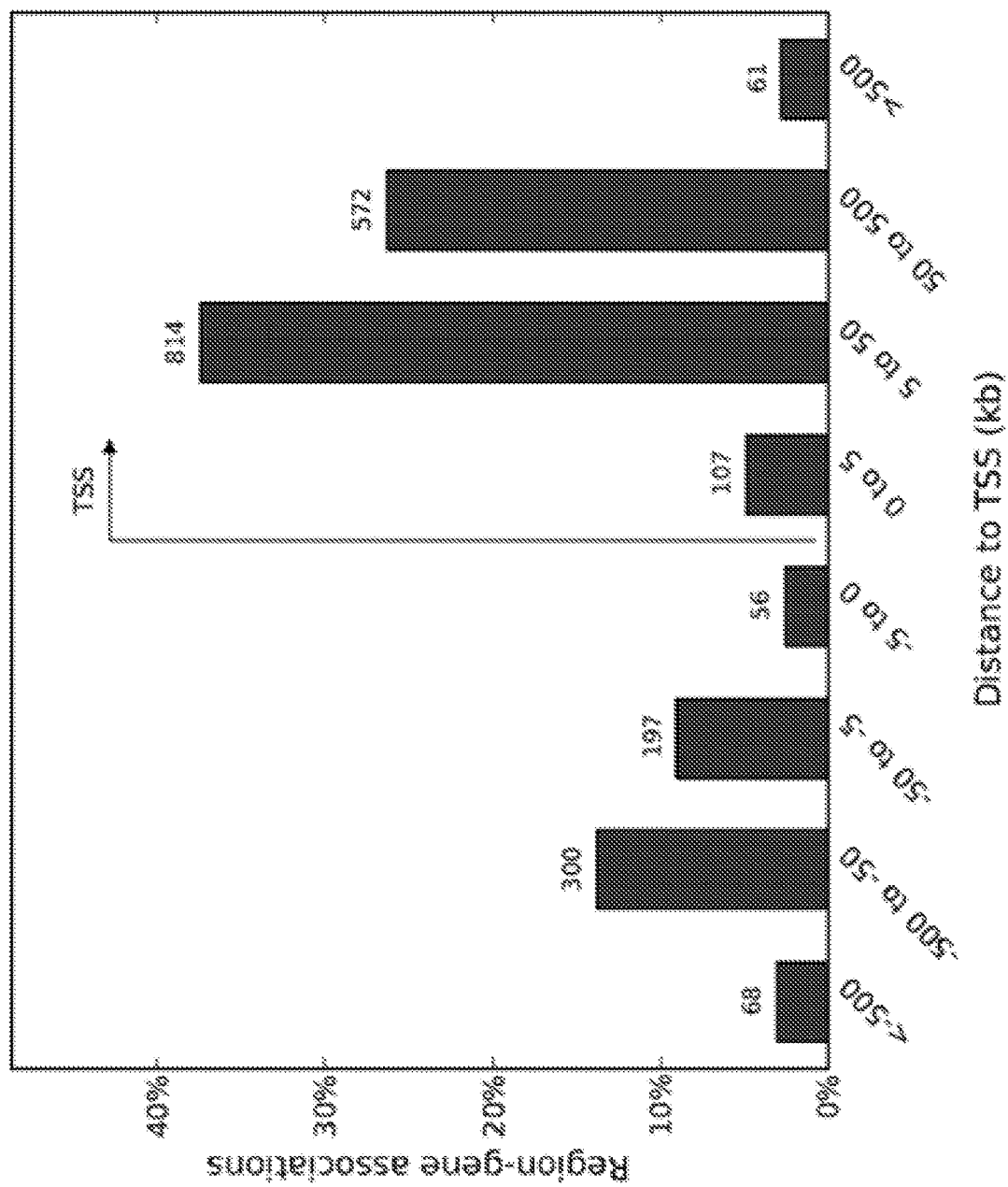
FIGS. 16a-b show the distribution of LV integrations along the genome of transplanted mice.
Figure 16B:
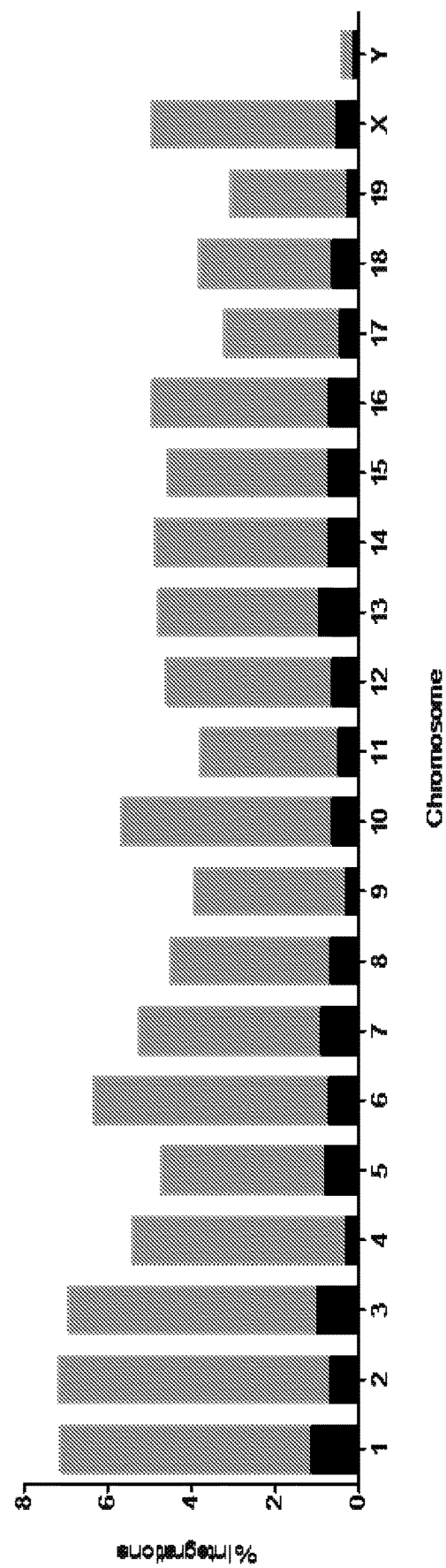

Overall, we mapped 5,173,892 sequencing reads on the transplanted mouse genome, resulting in 2,220 unique vector integration sites. The genomic distribution of ISs from two independent experiments matched the previously reported LV preference for integration within transcriptional units (particularly within the first 50 Kb downstream of the transcription start site—TSS—) (FIG. 16a), showing no skewing towards any particular chromosome in the mouse genome (FIG. 16b). FIG. 16a shows Integration site (IS) frequency distribution around Transcription Start Site (TSS) of the nearest RefSeq gene, spanning 500 Kb upstream and downstream the TSS. Numbers on the top are the number of IS detected for all samples and time-points. FIG. 16b shows chromosomal distribution of LV integration sites in transplanted mice expressing the EGFP transgene (black bars) or the coRPK therapeutic transgene (grey bars), showing no skewing towards any particular chromosome.

Figure 17A:
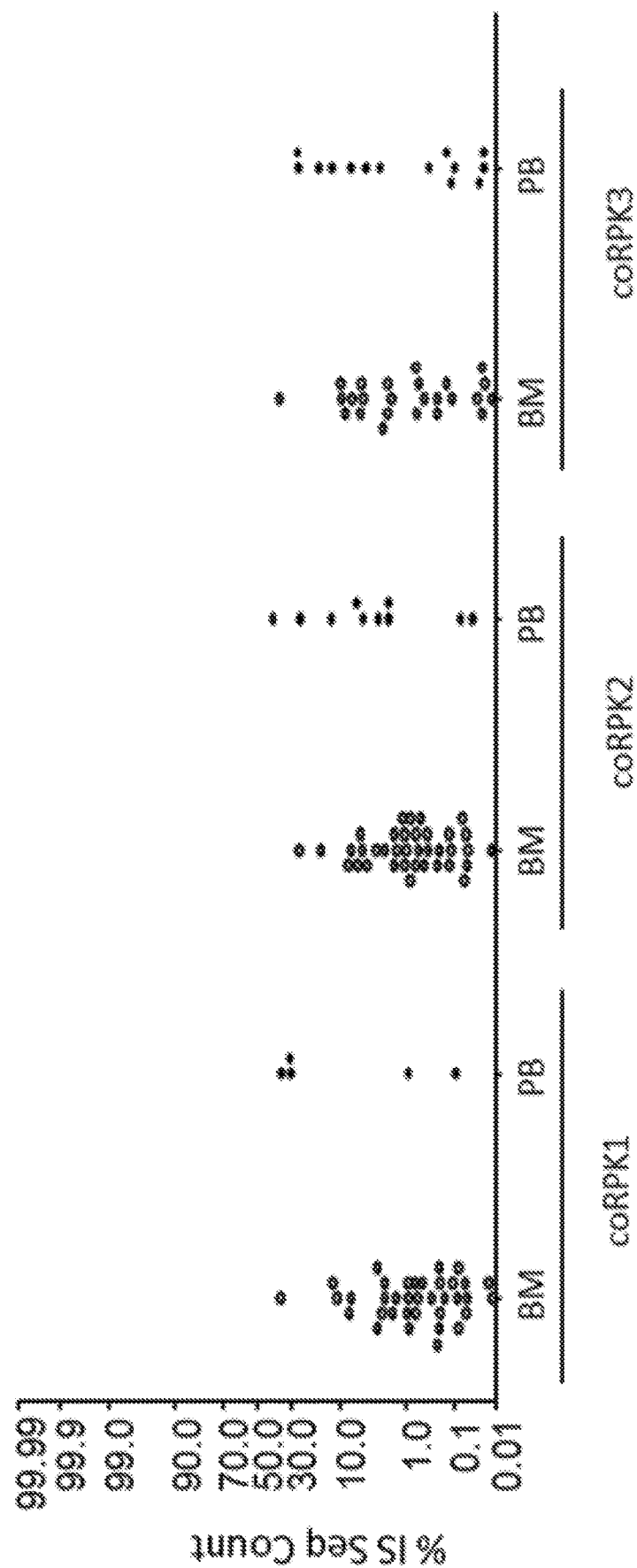
FIGS. 17a-c demonstrates clonal abundance analysis of coRPK-LV transduced cells. Dots plot representation of clonal abundance of pooled integrations in each mouse from assays 1 (FIG. 17a) and 2 (FIGS. 17b and 17c). The relative percentage (y-axis) for each integration site is relative to the total number of sequences reads obtained in each dataset. IS, integration site; BM, bone marrow; PB, peripheral blood; coRPK1-14, mice transplanted with hematopoietic cells transduced with the therapeutic vector.
Figure 17B:
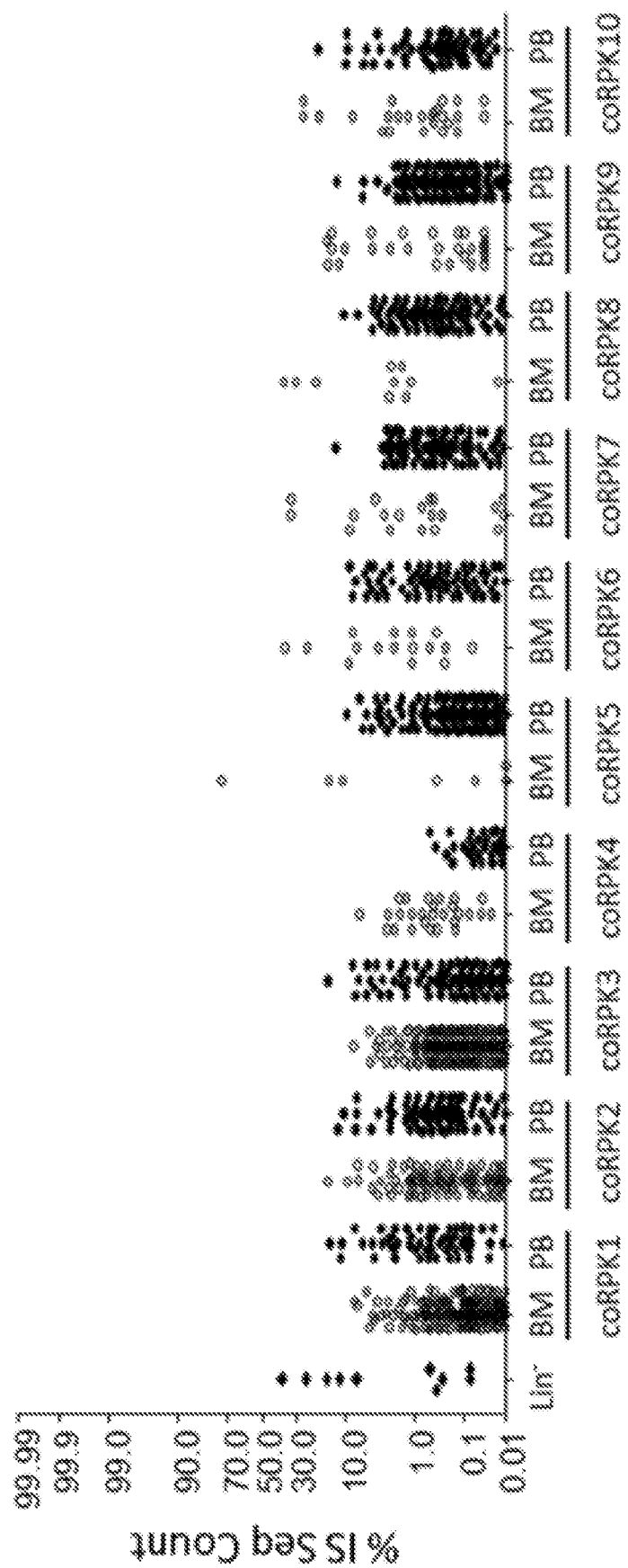
Figure 17C:
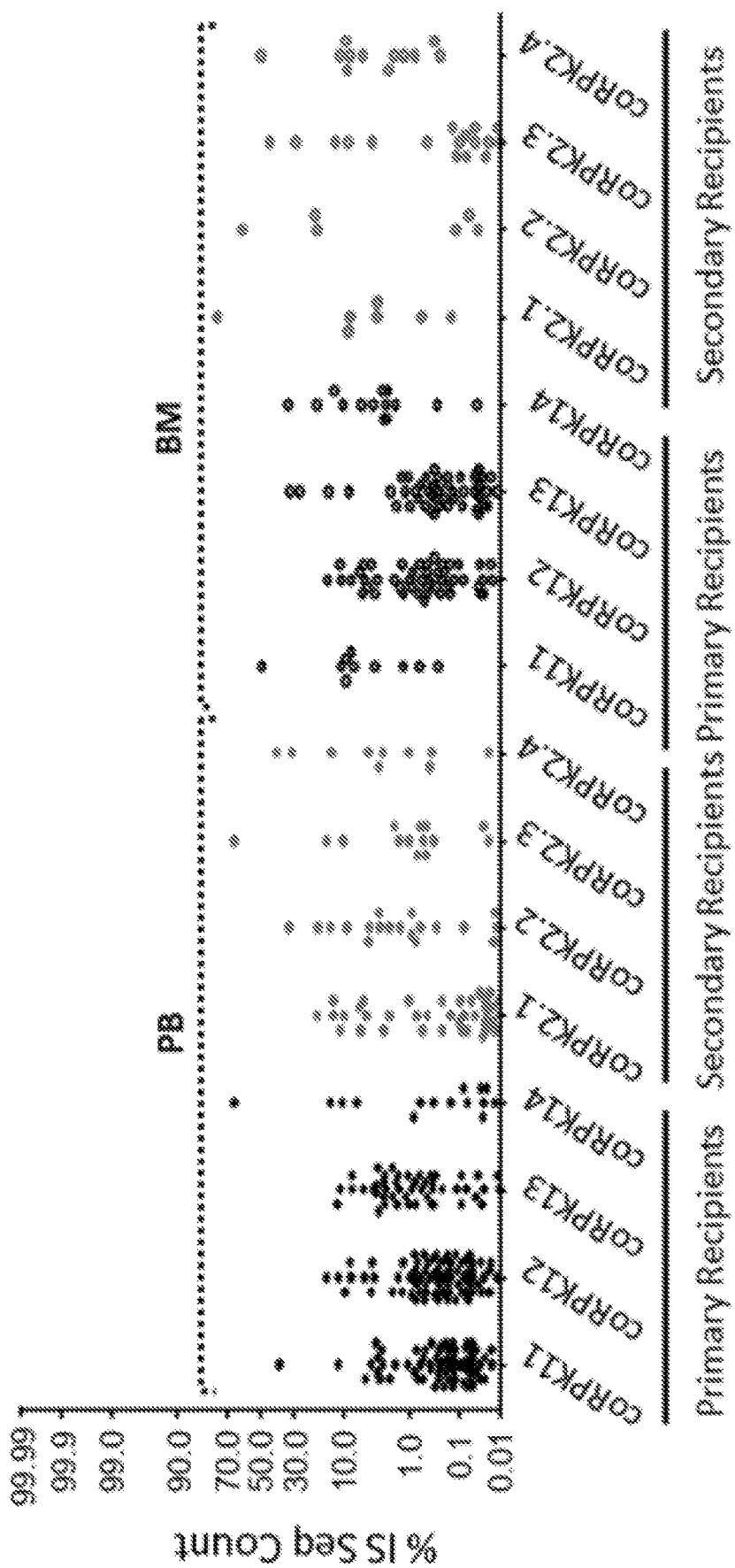
Figure 19:
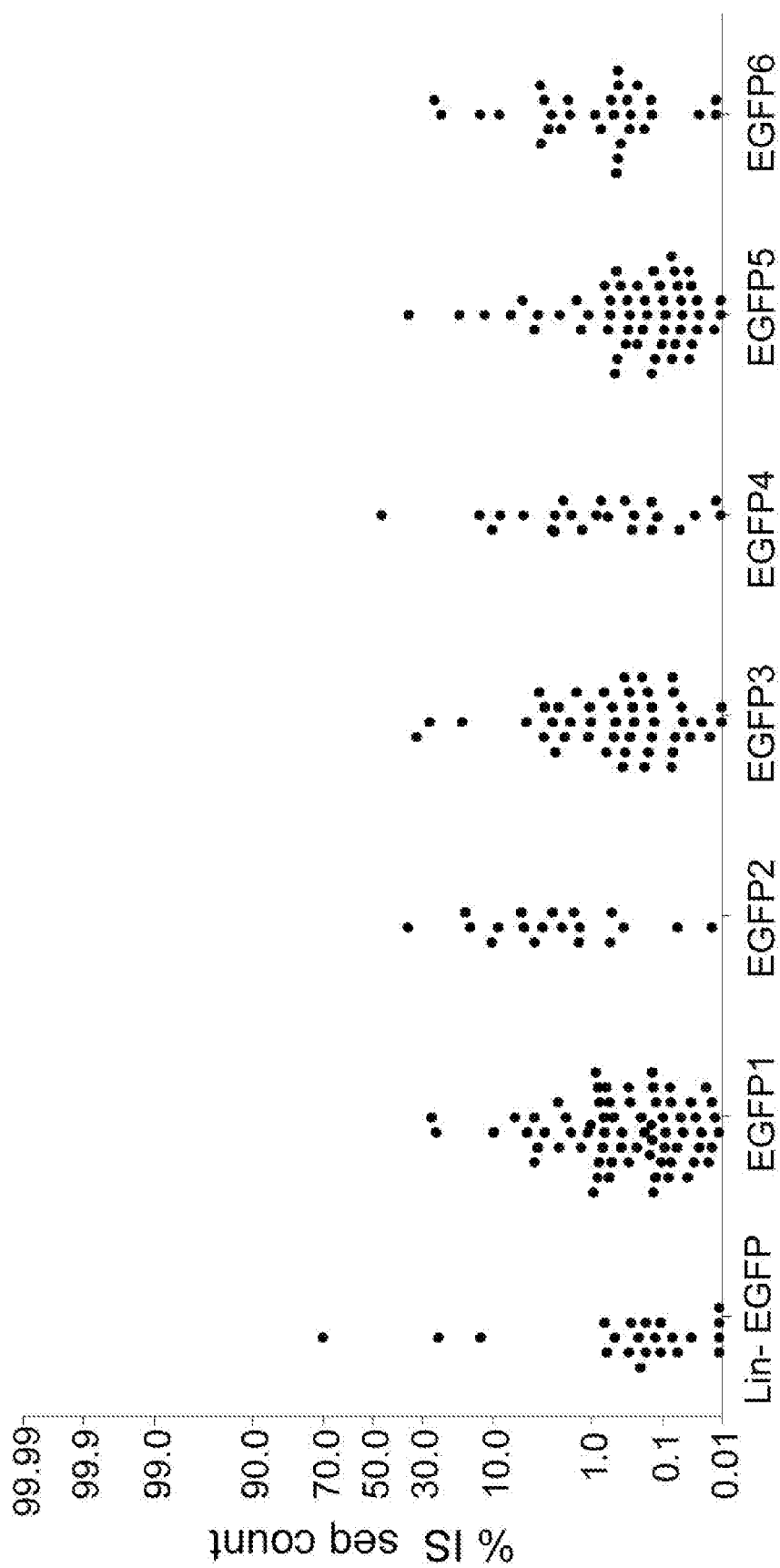
FIG. 19 demonstrates clonal abundance analysis of EGFP-LV transduced cells. Dots plot representation of clonal abundance of pooled integrations in each mouse in bone marrow. The relative percentage (y-axis) for each integration site is relative to the total number of sequences reads obtained in each dataset. Similarly to co-RPK transduced cells (FIG. 17), the graph indicates that the vast majority of transplanted mice show a polyclonal pattern of hematopoietic repopulation. IS, Integration site

Safety of the PGK-coRPK LV-based gene therapy was studied by clonal abundance estimations, calculating the percentage of sequence count for each IS (a clonal mark) with respect to the total number of sequences of the dataset. Dot plots and heat map representations of the relative abundance of each IS retrieved for each mouse (FIGS. 17, 18 and 19) showed strong fluctuations in clonal composition of the different mice and of in vitro cultured Lin⁻ cells. FIG. 17 is a chart of tracked shared integrations between primary and secondary recipient mice carrying the therapeutic PGK-coRPK LV vector. Integrations detected in either mouse in any organ and at any time are pooled. Secondary recipients received the pooled BM from transplanted mice coRPK11 to 14. The rest of the IS detected were detected or in the primary or in the secondary recipients. Numbers in the boxes show the representativeness in percentage of the corresponding integration in the referred mouse. In addition to >5% filter applied on integration analysis, all integration with a sequence count<3 were eliminated. FIG. 19 presents dot plot representation of clonal abundance of pooled integrations in each mouse in bone marrow. The relative percentage (y-axis) for each integration site is relative to the total number of sequences reads obtained in each dataset. Similarly to co-RPK transduced cells (FIG. 17), the graph indicates that the vast majority of transplanted mice show a polyclonal pattern of hematopoietic repopulation.

Also, it was possible to appreciate that for several samples, a small number of integrations contributed to a large amount of sequence reads (FIGS. 17 and 18), revealing a polyclonal pattern of repopulation of transduced HSCs. In addition, tracked shared integration between primary mice carrying the therapeutic PGK-coRPK LV and subsequently transplanted secondary mice showed no strong sharing of integrations between the groups, confirming the absence of clonal dominance (FIG. 18).

To determine whether hallmarks of insertional mutagenesis were present in transplanted mice, we assessed the occurrence of Common Insertion Sites (CIS) similar to currently ongoing LV-mediated clinical trials. CIS are insertional hotspots that may result from integration bias at the time of transduction or in vivo selection of clones harbouring vector integrations that confer growth advantage. CIS were identified using an algorithm based on Abel and cols and the Grubbs test for outliers finding no CIS and thus no alarming signs of genotoxicity by this readout. Moreover, gene ontology (GO) analysis revealed no skewing towards gene classes involved in cancer, cell proliferation or regulation of apoptosis in any of the integration datasets sorted by tissue-distribution, time point or abundance of repopulating hematopoietic cell clones (FIG. 20). FIG. 20 represents LV genomic integration profile. Gene Ontology (GO) analysis was performed using the GREAT software on samples from transplanted mouse. All integrations retrieved from this study (N=2220) showed overrepresentations of the gene functions indicated on the left part of the figure. To address if the most abundant integrations were enriched on specific gene classes, all integration sites with a relative sequence count>5% of the entire dataset (shown in FIG. 17) were selected, showing no GO gene classes overrepresented.

These results suggest neutrality of vector integration and demonstrate the safety of the PGK-coRPK LV in a preclinical setting.

Example 6

Human Clinical Trial

A clinical trial is conducted to evaluate safety and preliminary efficacy of autologous hematopoietic stem cell transplantation (HSCT) using the EU/3/14/1130 medicinal product (autologous CD34+ hematopoietic stem cells transduced with the lentiviral vector containing the RPK gene) in patients with pyruvate kinase deficiency with a history of severe and transfusion dependent anemia refractory to splenectomy.

The ODD EU/3/14/1130 comprises a self-inactivating lentiviral vector expressing the codon-optimized version of the therapeutic human PKLR gene (FIG. 21).

Self-inactivating lentiviral vectors (SIN-LV) provide a more robust expression (Ellis 2005) and are less susceptible to transcriptional silencing than gamma-retroviral vectors (Pfeifer, Ikawa et al. 2002). They also show a much safer integration profile (Schroder, Shinn et al. 2002) (Mitchell, Beitzel et al. 2004) (Wu, Li et al. 2003), and because of the 400 by deletion that they carry in the 3' LTR sequence (Miyoshi, Blomer et al. 1998) (Zufferey, Dull et al. 1998), transgene expression is regulated by internal promoters, increasing the safety of the LV-based genetic modification.

Vector sequence of the accepted lentiviral vector also includes several modifications to improve transgene expression and safety in target cells.

One modification is the use of the human phosphoglycerate kinase (PGK) promoter, already characterized by its stable in vivo activity and improved safety properties compared to other promoters used in gene therapy (Montini, Cesana et al. 2006, Modlich, Navarro et al. 2009, Montini, Cesana et al. 2009, Biffi, Montini et al. 2013). PGK leads to a more physiological expression of the transgene and a lower susceptibility to transcriptional silencing (Gerolami, Uch et al. 2000, Zychlinski, Schambach et al. 2008).

Another modification is a codon-optimized version of the human PKLR cDNA (coRPK) to increase mRNA stability upon transcription. For the optimization the GeneArt® software has been used, increasing the GC content and removing cryptic splice sites in order to avoid transcriptional silencing and therefore increase transgene expression. The coRPK optimized sequence showed 80.4% homology with the human PKLR gene, with no changes in the amino acids sequence of the protein.

Another modification is a mutated post-transcriptional regulatory element of the woodchuck hepatitis virus (Wpre), lacking any residual open reading frame (Schambach, Bohne et al. 2006) is also included to improve the level of expression and stability of the therapeutic gene. The backbone, promoter and Wpre* sequences of this lentiviral vector (PGK-coRPK LV) are the same as the one corresponding to the medicinal product "Lentiviral vector containing the Fanconi anemia A (FANCA) gene for the therapy of Fanconi anemia Type A patients" (Ref 141/2000), as well as vector backbone used in the currently ongoing clinical trial for the metachromatic leukodystrophy (MLD) (Biffi, Montini et al. 2013).

Mode of Action

Figure 22A:
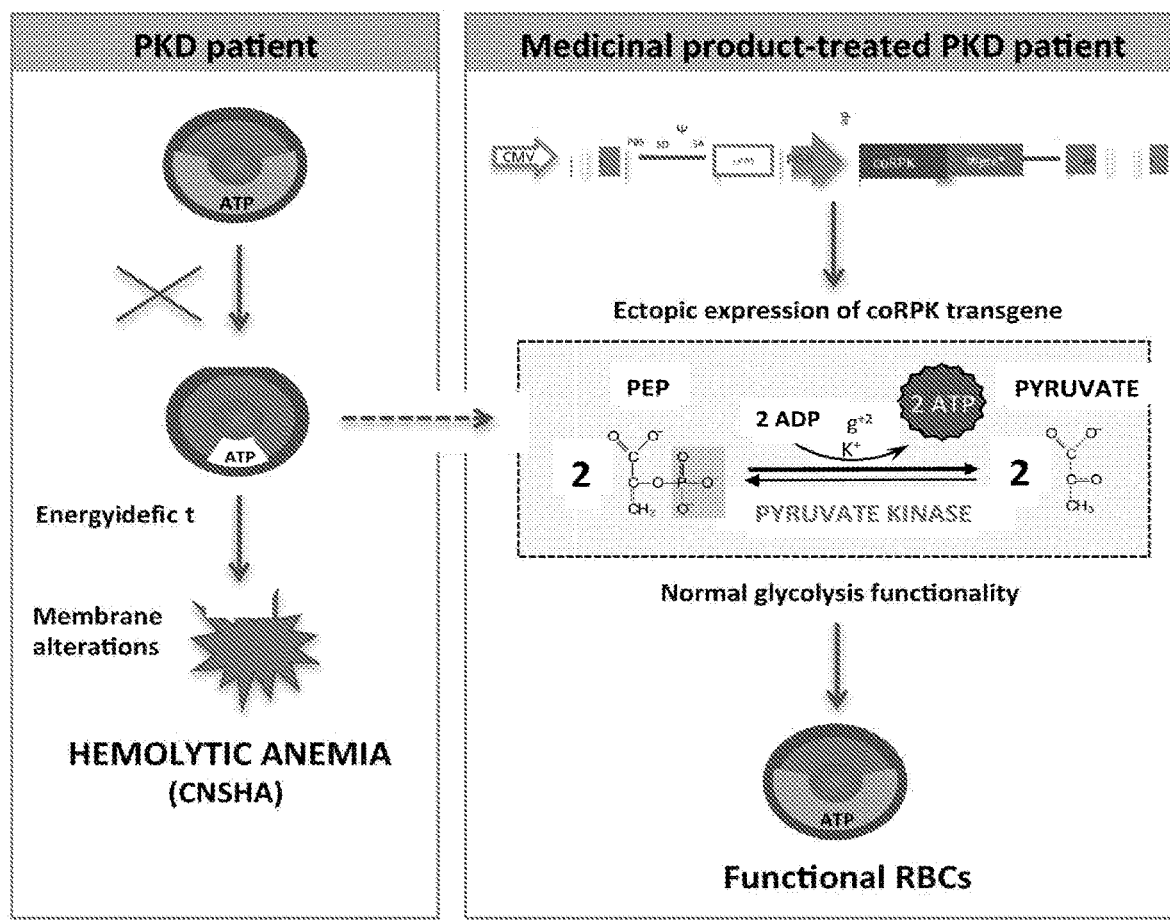
FIGS. 22a-b depicts the mechanism of action of the medicinal product.
Figure 22B:
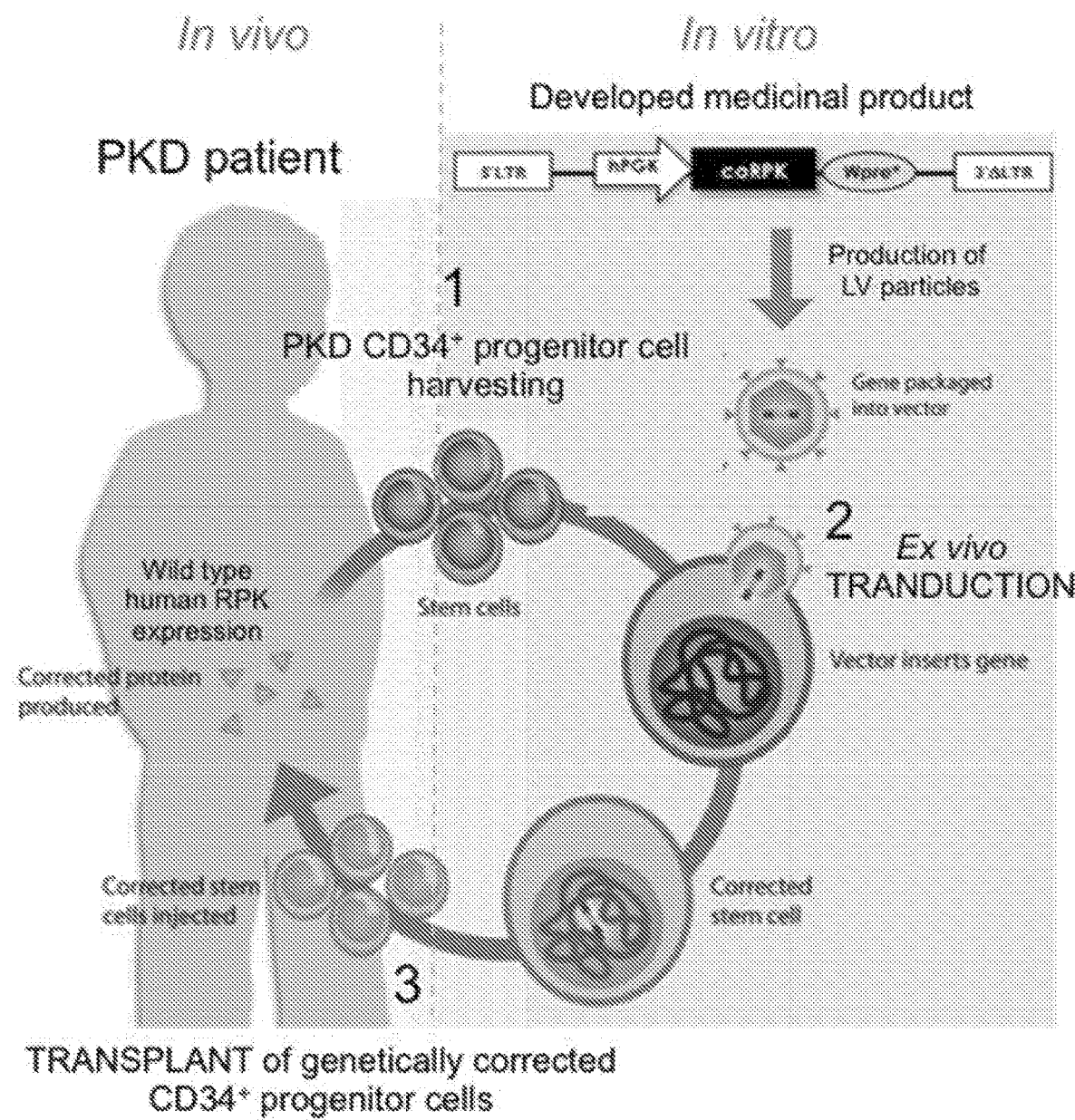

After harvesting the CD34+ progenitor cells from PKD patients, either from bone marrow (BM) or mobilized peripheral blood cells, they will be transduced ex vivo with the medicinal product and the therapeutic vector will be integrated in the genome of the cells. Once integrated, the therapeutic human gene (coRPK) will be transcribed and translated within deficient cells to produce the therapeutic RPK protein that is missing or reduced in PKD mature erythrocytes. Transduced PKD hematopoietic progenitors will be then genetically corrected, and thus able to produce RBCs with sufficient amounts of ATP to accomplish their functions (FIG. 22). These genetically corrected hematopoietic progenitors (which will constitute the medicinal product) will be then transplanted back into the patient, where once engrafted will generate normal erythrocytes, life-long curing the disease.

The active principle will consist in a cellular suspension of corrected hematopoietic stem cells (CD34+) cells with the therapeutic lentiviral vector PGK.coRPK.wpre designed as orphan drug by the European Commission (ODD EU/3/14/1130) for the treatment of pyruvate kinase deficiency. Thus, this new medicament should be included in the groups of advanced therapy developments within the gene therapy sub-class.

The active principle will be composed by of a genetically modified cellular suspension of at least $2 \times 10^6$ CD34+ cell/Kg of body weight with at least 0.1 copies of the therapeutic vector per cell. The cells will be suspended in a saline buffer with 2% HSA.

The final therapeutic product will be produced according to the GMP rules, so the product requirements for its liberation and its infusion in the patient will be related with the quality of the product. In relation to this these specifications will be cellular viability>30%, sterility (Gram test and sterility by Pharmacopeia), absence of mycoplasma, absence of replicative competitive lentiviral particles, and demonstration of the potency of the therapeutic potential by the detection of the presence of at least 0.1 vector copies per cell by quantitative PCR. Additionally, investigation and research studies of the content of hematopoietic progenitors and the vector copy number in these will be performed. Three independent validations will be performed with healthy control cells to assure the procedure reaches the above described requirements.

The final product will be finished packaged in a transfer bag sealed by heat and especially for freezing and storage until its infusion to the patient; previously, samples will be collected for the precise corresponding quality controls.

Mobilization

Patients will be mobilized in their respective hospitals, although the two first patients will be mobilized in the Hospital del Niiio Jesus, Madrid (Spain). Mobilization process will consist in the administration of recombinant stimulating factor granulocyte colony (G-CSF, Neupogen, Amgen, Thousand Oaks, Calif., USA) at doses of 12 mg/kg twice a day for up to eight days from birth, Plerixafor 4th day 240 mg/kg/d (Mozobil®, Genzyme Europe BV, Naarden, Netherlands) to four subcutaneous doses for 4 consecutive days. The hematopoietic progenitor cells from peripheral blood will be collected by leukapheresis large volumes from day 5 of mobilization through a cell separator and according to standard protocols in Hospital Niiio Jesus in Madrid. All the instruments and solutions are CE marked and meet the specifications of the legislation for medical devices.

CD34+ Cell Purification

Consistent with the mobilization process, the apheresis will take place in the hospital where the patient is mobilized. Apheresis will be processed immediately to select hematopoietic progenitors (CD34+ cells) through MACS "magnetic cell sorting" technology (Miltenyi Biotec, Germany) which permits separation of cells by a high magnetic field gradient, through a powerful permanent magnet and a separation column with a ferromagnetic matrix. The CliniMACS (Miltenyi Biotec, Bergisch Gladbach, Germany) system consists on a computer (CliniMACS® plus Instrument), a specific CD34+ selection software, a set of sterile tubes (CliniMACS Tubing Sets), magnetic-controlled reactive sterile instrument (CliniMACS CD34 Reagent) and a sterile buffer (CliniMACS PBS/EDTA Buffer). The instrument and reagents used will be CE marked and will meet the specifications of the legislation for medical devices. During this phase and in later washes nonspecific immunoglobulin (intravenous Flebogamma 5% 0.5 gr, Grifols) and human albumin (human albumin Grifols® 20%, Grifols) are employed, which are later removed by washing after centrifugation. The CD34+ cells will be then quantified. Microbiological controls on the products obtained will be performed by taking standard fungal, aerobic bacteria and anaerobes samples for cultures following specific protocols.

CD34+ Transduction

Transduction of the purified CD34+ cells with the ODD EU/3/14/1130 will be done under GMP conditions in a time window within 48 h since the extraction of the cells from the patient (apheresis). Ex-vivo culture of the cells will last less than 48 hours, and will be cultured following established standards including the use of properly formulated media X-vivo-20 (Lonza), addition of hematopoietic growth factors (100 ng/ml hrSCF, 100 ng/ml hrFlt-3, 100 ng/ml TPO and 20 ng/mL IL-3 (all from Prepotech), Pulmozyme and controlled 5% $O_2$ concentration. Transduction will be performed with a GMP lentiviral batch of the ODD EU/3/14/1130 produced by VIVEbiotech (San Sebastian, Spain). After transduction cells will be washed in X-vivo-20 (Lonza) to be finally packaged in a transfer bag suitable for cryopreservation. Specific samples will be collected to determine if the final product meets all the specifications already mentioned for its final liberation. Three independent validations will be performed to evaluate the stability of the product. All products and solutions, including the vector, will meet the specifications of the legislation for medical devices and clinical use. Before production, all raw materials (including consumables, biological reagents and chemical powders) will be inspected by the Quality Control (QC) Unit of CliniStem according to standard operating procedures (SOPs).

Conditioning

Patients will be conditioned according to standardized and specific protocols considered for the trial. To consider a patient for conditioning an alternative a back-up of $2 \times 10^6$ unmanipulated CD34+ cells/kg will be kept frozen to be used in case the prepared product do not completely reconstitute the haematopoiesis of the treated patient.

Infusion

Previous to infusion, patient eligibility will be checked to ensure they meet the study requirements. The day of infusion, premedication and prophylactic medication used will be recorded.

Example 7

Non-Clinical Development

Previous work demonstrated the feasibility of HSC gene therapy for PKD in mice when above 25% genetically corrected cells were transplanted. These results suggest that a significant number of donor gene-corrected HSCs (Zaucha, Yu et al. 2001) and high levels of transgene expression are needed to achieve a therapeutic effect in PKD. We have developed a new therapeutic lentiviral vector proposed for this clinical trial, harbouring the hPGK eukaryotic promoter driving the expression of the PKLR cDNA that was designated as Orphan Drug on August 2014 (EU/3/14/1130). With this vector we conducted a preclinical gene therapy protocol for PKD in a mouse model of the disease. With lentiviral dosages based on clinical standards, ectopic RPK expression was able to normalize the erythroid compartment, correcting the haematological phenotype and reverting organ pathology. Metabolomic studies demonstrated the functional correction of the glycolytic pathway in genetically corrected RBCs, with no metabolic disturbances observed in leukocytes. Remarkably, WBCs analyzed in parallel showed no alterations of the metabolic balance in leukocytes when RPK is ectopically expressed under the activity of an ubiquitous promoter such as PGK, ruling out a leukocyte metabolic advantage as possible safety concern and reinforces the therapeutic potential of the EU/3/14/1130 vector.

The multi-lineage reconstitution and the absence of any leukemic event or clonal expansion in secondary recipients after the proliferative stress induced by BM re-transplant demonstrate the long-term stability and safety of the PGK-coRPK LV vector-based protocol. The use of the human PGK eukaryotic promoter that i) likely led to a more physiological expression of the RPK transgene, ii) has been proven to be a weak transactivator and iii) is being currently used in the clinical trial for metachromatic leukodystrophy (MLD), could also account for the safety of the whole procedure.

To assess the long-term safety of HSC gene therapy through the analysis of vector integration sites, next generation sequencing was used to predict the risk of insertional oncogenesis in HSC. More than 5,173,892 sequences reads were mapped on the mouse genome to a total of 2220 unique vector IS, finding no evidence of in vivo expansion or selection of clones harboring IS. Rather, our data show the clonal composition and dynamics of hematopoiesis after transplantation of transduced HSCs in mice, suggesting a genuine and stable genetic in vivo modification of HSC over time. Overall, the analysis of the vector integration pattern emphasizes the safety properties of the PGK-coRPK LV vector that provides PKD genetic correction with no evidence of genotoxicity.

Example 8

Clinical Development

So far, no clinical studies have been conducted with the medicinal product. This is the first time protocol assistance is requested to a Regulatory Agency. Our aim is to perform a clinical trial sponsored by the European Commission. The ForGeTPKD Consortium, composed by different clinicians and basic researchers in Europe, has been established to focus in PKD research and development of new therapeutic strategies. ForGeTPKD clinical trial will be the first administration of this medicinal product in humans. It is designed as an International, Multicenter, Phase I/II Open Label Study to evaluate the Safety and Efficacy of Transplantation of Autologous CD34+ Cells Transduced Ex Vivo with a Lentiviral vector containing the red-cell type Pyruvate Kinase (RPK) gene (EU/3/14/1130) in patients with Severe Pyruvate Kinase Deficiency.

Regulatory Status

The medicinal product has no marketing authorization at present time. The objective of the PKD Consortium is to move forward to the clinical development of the medicinal product in order to eventually receive a marketing authorization.

The mentioned final product will be produced with a lentiviral vector that has received the Orphan Drug Designation related to:

Indication: Treatment of Pyruvate Kinase Deficiency

Criteria: The only curative treatment for PKD is allogeneic BMT, which has been used in patients with transfusion-dependent severe anemia refractory to other measures. However, allogeneic BMT is not a widely accepted treatment for PKD (only one patient reported in the literature (Tanphaichitr, Suvatte et al. 2000)) as it is associated with severe complications related to intensive pre-allo-BMT conditioning by chemotherapy or chemo-radiotherapy, as well as acute and chronic graft-versus-host disease (GVHD). Our hypothesis is that gene therapy using autologous hematopoietic stem cells transduced with viral vectors containing the wild type version of the gene, provided by the ODD EU/3/14/1130, may represent a potential curative opportunity for these patients, avoiding the risks of GVHD, the main cause of failure of a hematopoietic progenitors transplant.

Active substance: Autologous CD34+ hematopoietic stem cells, transduced with Lentiviral vector containing the red-cell type Pyruvate Kinase (RPK) gene (ODD EU/3/14/1130), expressing the wild type version of the protein Finished product: Frozen bag containing at least $2 \times 10^6$ active substances/kg body weight of the patient, suspended in a saline buffer with 2% HAS Example 9

Pharmacology

Completed studies: The medicinal product developed includes several modifications in its sequence that provides some advantages for the gene therapy for PKD: 1) The use of a SIN-LV vector design allowed a relatively easy and safe production of viral stocks, able to efficiently transduce HSCs; 2) the use of a weak and eukaryotic promoter such as hPGK, which is less susceptible to silencing by methylation (Gerolami, Uch et al. 2000), leads to a more physiological expression of the transgene, achieving therapeutic levels with a viral dosage (1.65 VCN) within the clinical standards (Matrai, Chuah et al. 2010); and 3) the codon optimized transgene sequence and the presence of the mutated Wpre sequence increase transgene mRNA stability: no reporter gene was included in the therapeutic vector sequence, avoiding possible immunogenic problems (Morris, Conerly et al. 2004); (Stripecke, Carmen Villacres et al. 1999).

The developed hPGK-coRPK LV medicinal product efficiently reverted PKD pathology in both primary and secondary deficient mice transplanted with progenitors transduced and corrected with the ODD EU/3/14/1130. The correction was achieved with cells carrying on average 1.65 copies per cell of the therapeutic transgene.

Human PGK promoter was potent enough to express clinically relevant levels of coRPK protein, restoring the hemolytic phenotype in transplanted mice.

The genetic correction was able to: Extend RBC half-life; Normalize the hematological variables and reticulocytes levels; Revert the compensatory erythropoiesis constitutively activated in PKD mice; Rescue the pathology in spleen and liver, remarkably reducing the iron overload, which is one of the life-threatening complications of PKD. In addition, the ectopic expression of human RPK corrected the energetic defect in RBCs without altering the metabolic balance in WBCs, emphasizing the efficacy and safety of the medicinal product.

Example 10

Ongoing Studies

Transduction of human hematopoietic progenitors from healthy donors and PKD patients for the study of: 1) efficiency of transduction of the ODD EU/3/14/1130 in human cells; 2) definition of the optimal vector copy number/cell to get efficient and therapeutic expression of the RPK therapeutic protein; and 3) definition of the optimal conditions to get therapeutic transduction levels without losing hematopoietic stem cell ability.

Planned studies include set up of the conditions for large scale transduction at the GMP facility and pre-validation and 3 validation studies to set up the optimal conditions to reach the required specifications defined for the final therapeutic product.

Toxicology

Completed studies include 1) The ectopic expression of human RPK corrected the energetic defect in RBCs without altering the metabolic balance in WBCs; 2) Genome integration analysis of the vector has demonstrated that (i) The analysis of the relative abundance of specific cell clones revealed an oligoclonal hematopoietic reconstitution for some mice, showing no clonal dominance for any primary and secondary transplanted mice; (ii) Common Integration Sites (CIS, dense clusters of vector integrations in defined genomic intervals), considered a hallmark of insertional mutagenesis did not show any sign of genotoxicity, neither an abnormal enrichment of CIS over time and detected CIS from the two independent gene therapy experiments performed in mice were not represented by high sequence counts and did not preferentially target oncogenes; (iii) Gene ontology (GO) analysis of the genes targeted by the lentivirus integration and study of the position of the vector integrations in specific regions of the genome demonstrated no skewing towards gene classes involved in cancer, cell proliferation or regulation of apoptosis; and (iv) Overall, medicinal product integration analysis did not show any evidence of genotoxicity.

Planned studies include 1) Analysis of Recombinant Competent Lentiviruses (RCL) production: Human T lymphocytes from healthy donors and from PKD patients will be transduced with the ODD EU/3/14/1130 and culture in vitro for extended periods of time. Presence of viral p24 protein will be analyzed in the supernatants by ELISA to evaluate the potential generation or RCLs and 2) Biodistribution of the medicinal product: Mouse hematopoietic progenitors will be tranduced with the ODD EU/3/14/1130 and transplanted into lethally irradiated recipients. One month post-transplant animals will be sacrificed and different organs (gonads, liver, kidney, brain, bone marrow, spleen and peripheral blood) will be analyzed for the presence of vector DNA; and 3) Vector integrome in human cells: Hematopoietic progenitors from healthy donors and from PKD patients will be transduced with the ODD EU/3/14/1130 and transplanted into severe immunodeficient mice to allow the engraftment and proliferation of human hematopoietic cells. At different time points (1, 2 and 3 months post-transplant) blood and BM transplants will be taken, sorted for human cells and subjected to vector integrome analysis as already performed with mouse cells.

Example 11

Human Clinical Trial

To test clinical efficacy the ForgetPKD trial will be conducted. The proposed clinical trial aims to evaluate safety and preliminary efficacy of autologous hematopoietic stem cell transplantation (HSCT) using the EU/3/14/1130 medicinal product (autologous CD34+ hematopoietic stem cells transduced with Lentiviral vector containing the red-cell type Pyruvate Kinase (RPK) gene) in patients with pyruvate kinase deficiency with a history of severe and transfusion dependent anemia refractory to splenectomy.

The primary objective is to evaluate treatment safety and tolerability/feasibility. The following endpoints will be measured in accordance: 1) incidence and characterization of Adverse Events (AE), including: AE related to the infusion of the transduced cells, AE derived from conditioning prior to cell infusion, and AE derived from clonal evolution related with the transduced cells; and 2) number of patients with stem cell engraftment at 30 days post-transplant.

Secondary objectives are to evaluate preliminary treatment efficacy. The following endpoints will be measured in accordance: Number of patients who become "transfusion independent" at the end of the study; In patients who still need transfusions after treatment, ratio between the mean numbers of transfusions needed within the study period (1 year) with respect to the mean number of transfusion in the last 1.5 years before baseline evaluation; Clinically significant reduction of anemia, defined as number of patients with rise in Hemoglobin levels in 2 gr/dL from baseline at the end of the study; Clinically significant reduction of reticulocytosis, defined as number of patients with a reduction of 50% from baseline evaluation at the end of the study; and Number of patients with stem cell engraftment where 1% transduced cells can be detected at 6 and 12 month post-cell infusion and at the end of the study.

An exploratory objective is to evaluate treatment impact on patient's quality of life. The following end-point will be measured in accordance: Improvement in quality of life from baseline at the end of the study, using a quality of life questionnaire (SF-36 for adults or PEDSQL for children) and its translated validated versions in the language of the participant countries (Italian, Dutch and Spanish).

ForGetPKD Trial is a multicenter, international trial, which will be carried out in 3 EU member states: Spain, Italy and The Netherlands. Participating centers include Reference National Investigators and Institutions for PKD diagnosis and treatment.

The trial will represent the first administration to humans of the described product. It is designed as a non-comparative, open label, single-dose, Phase I/II study.

Global Study duration will be 2 years from the first visit of the first patient to the last visit-last patient. This includes 1 year of recruitment period and 1 year of treatment period and early (immediate) follow-up. After the end of the trial, included subjects will be asked to participate in a subsequent follow up study that will monitor safety and efficacy for up to 5 years after transplant.

According to disease incidence and study design, we are planning to include 6 patients in one year. This estimate has been decided considering that there are 3 potential participants already identified.

Study procedures include a Screening Period, a Treatment Period and a Follow-up Period. Details of visits on each phase and associated study procedures are detailed below and summarized in Table 4.

TABLE 4

| Study procedures | Screening Period | | Treatment Period Visit | Follow up period | | | |
|---|---|---|---|---|---|---|---|
| | −1 Pre-screening | 0 Baseline | 1 Treatment period | 2 + 1 m | 3 + 3 m | 4 + 6 m | 5 + 12 m |
| Informed consent | X | | | | | | |
| Inclusion/exclusion Criteria | X | X | | | | | |
| Medical History | X | | | | | | |
| Physical Examination | X | X | X | | | | |
| CBCs | X | | X | X | X | X | X |
| Biochemistry | X | | X | X | X | X | X |
| Coagulation | X | | X | X | X | X | X |
| Conditioning regimen | | | X | | | | |
| Transduced cells infusion | | | X | | | | |
| Discharge | | | X | | | | |
| Bone Marrow sampling | | | | | | | X |
| Cell engraftment in peripheral blood | | | | X | X | X | X |
| Average vector copy number in peripheral blood | | | | X | X | X | X |
| Vector integration pattern in peripheral blood | | | | X | X | X | X |
| Cell engraftment in bone marrow | | | | | | X | X |
| Average vector copy number in bone marrow | | | | | | X | X |
| Vector integration pattern in bone marrow | | | | | | X | X |
| Cell extraction | X | | | | | | |
| Availability of viable cells | X | | | | | | |
| Quality of life questionnaire (SF-36 or PEDSQL) | X | | | | | | X |

TABLE 4-continued

| Study procedures | Screening Period | Treatment Period Visit | Follow up period | | | |
|---|---|---|---|---|---|---|
| | −1 Pre-screening | 0 Baseline | 1 Treatment period | 2 + 1 m | 3 + 3 m | 4 + 6 m | 5 + 12 m |
| Concomitant Medication | X | X | X | X | X | X | X |
| Adverse Events | X | X | X | X | X | X | X |

Screening Period

Visit-1: Pre-Screening Visit

Potential candidates will be informed of the aims and characteristics of the trial, and written informed consent will be taken, fulfilled and signed by the patient (or legal representative if underage), by duplicate. To be eligible for the study, patients must fulfill all inclusion criteria and none of the exclusion criteria, which will be checked. This includes a pre-treatment procedure to mobilize and obtain viable CD34⁻ cells, to A. Store $2\times10^6$ CD34⁺ cells/kg body weight to serve as a backup in case of non-engraftment, B. transduce at least $6\times10^6$ CD34+ cells/kg body weight with the EU/3/14/1130 vector to generate the medicinal product and to perform all the quality control needed for the liberation of the medicinal product. Only patients with enough transduced cells available after liberation of the medicinal product ($2\times10^6$ transduced CD34⁺ cells/kg body weight) will be included in the study.

The following procedures will be also performed in this visit:

Register of relevant medical o surgery history.

Register of demographic data and clinically relevant physical examination findings Register of relevant concomitant medications.

Peripheral blood testing for routine cell blood counts (CBC), Biochemistry,

Coagulation determination and serology

Echocardiogram, Lung function test and thorax X-ray

Quality of life questionnaire (SF-36 or PEDSQL)

Genetic diagnosis of PKD

To be eligible for the study, patients have to fulfill all of the following inclusion criteria and none of the exclusion criteria.

Inclusion criteria are male or female patients, Age>2 year old at the time of recruitment, willing to give signed informed consent (which will be signed by their parents or legal representative in case of children under 18 years old), previous diagnosis for PKD confirmed by genetic testing, history of severe transfusion-dependent anemia, not responsive to splenectomy, Candidate to Autologous Hematopoietic Stem Cell Transplant, >$2\times10^6$ transduced CD34⁺ cells/kg body weight available, and treated and followed for at least the past 2 years in a specialized center that maintained detailed medical records, including transfusion history.

Exclusion criteria are positive for presence of human immunodeficiency virus type 1 or 2 (HIV 1 and HIV 2), uncorrected bleeding disorder, presence of other causes of hemolysis, any prior or current malignancy or myeloproliferative or immunodeficiency disorder, immediate family member with a known or suspected Familial Cancer Syndrome (including but not limited to hereditary breast and ovarian cancer syndrome, hereditary non-polyposis colorectal cancer syndrome and familial adenomatous polyposis), in patients with previous allogeneic transplant, presence of residual cells of donor origin, patients with severe complications that after medical evaluation are considered to suffer grade III/IV cardiac, pulmonary, hepatic or renal function abnormalities, uncontrolled seizure disorder, diffusion capacity of carbon monoxide (DLco)<50% of predicted (corrected for hemoglobin), any other evidence of severe iron overload that, in the Investigator's opinion, warrants exclusion, participation in another clinical study with an investigational drug within 30 days of Screening, availability of a HLA-identical family donor for allogeneic bone marrow transplant, pregnant or breast-feeding women, patients that, according to investigator criteria, will not be able to understand study purposes, benefits and risks and/or to comply with study procedures, an poor functional status, evidenced by a Karnofsky Index≤80 in adults or Lansky≤80 in children.

The statistical analysis of the study will be descriptive. Qualitative endpoints will be described by frequencies and percentages. Qualitative endpoints include the adverse events, the number of patients with stem cell engraftment, the number of patients who become "transfusion independent", the number of patients who have a clinically significant reduction of anemia, the number of patients who have a clinically significant reduction of reticulocytosis, the number of patients with stem cell engraftment where presence of transduced cells can be detected, and the improvement in quality of life from baseline measured by SF-36 or PEDSQL questionnaire. Quantitative endpoints will be described by mean and standard deviation or by median and quartiles. Quantitative endpoints include the reductions of anemia and reticulocytosis from baseline, the number of transfusions needed within the study period with respect to the number of transfusion in the last 1 year before baseline evaluation, and the vector copy number in peripheral blood and bone marrow. All endpoints will be described at the end of the study.

Previous work demonstrated the feasibility of HSC gene therapy for PKD in mice when above 25% genetically corrected cell were transplanted. These results suggest that a significant number of donor gene-corrected HSCs (Zaucha, Yu et al. 2001) and high levels of transgene expression are needed to achieve a therapeutic effect in PKD. We have developed a new therapeutic lentiviral vector proposed for this clinical trial, harboring the hPGK eukaryotic promoter driving the expression of the PKLR cDNA that was designated as Orphan Drug on August 2014 (EU/3/14/1130). With this vector we conducted a preclinical gene therapy protocol for PKD in a mouse model of the disease. With lentiviral dosages based on clinical standards, ectopic RPK expression was able to normalize the erythroid compartment, correcting the hematological phenotype and reverting organ pathology. Metabolomic studies demonstrated the functional correction of the glycolytic pathway in genetically corrected RBCs, with no metabolic disturbances observed in leukocytes. Remarkably, WBCs analyzed in parallel showed no alterations of the metabolic balance in leukocytes when RPK is ectopically expressed under the activity of an ubiquitous promoter such as PGK, ruling out a leukocyte metabolic advantage as possible safety concern and reinforces the therapeutic potential of the EU/3/14/1130 vector.

The multi-lineage reconstitution and the absence of any leukemic event or clonal expansion in secondary recipients after the proliferative stress induced by BM re-transplant demonstrate the long-term stability and safety of the PGK-coRPK LV vector-based protocol. The use of the human PGK eukaryotic promoter that likely led to a more physiological expression of the RPK transgene, that has been proven to be a weak transactivator and is being currently used in the clinical trial for metachromatic leukodystrophy (MLD) could also account for the safety of the whole procedure.

To assess the long-term safety of HSC gene therapy through the analysis of vector integration sites, next generation sequencing was used to predict the risk of insertional oncogenesis in HSC. More than 5,173,892 sequences reads were mapped on the mouse genome to a total of 2220 unique vector IS, finding no evidence of in vivo expansion or selection of clones harboring IS. Rather, our data show the clonal composition and dynamics of hematopoiesis after transplantation of transduced HSCs in mice, suggesting a genuine and stable genetic in vivo modification of HSC over time. Overall, the analysis of the vector integration pattern emphasizes the safety properties of the PGK-coRPK LV vector that provides PKD genetic correction with no evidence of genotoxicity.

The invention claimed is:

1. A method of treating or preventing Pyruvate Kinase Deficiency (PKD) in a subject in need thereof, comprising:
    contacting a hematopoietic stem cell with a recombinant lentivirus vector comprising an expression cassette, wherein the expression cassette comprises a polynucleotide sequence encoding a pyruvate kinase, liver and red blood cell (PKLR) polypeptide operatively linked to a promoter, wherein the expression cassette comprises a woodchuck hepatitis virus post-transcriptional regulatory element (Wpre), wherein the Wpre comprises a sequence at least 90% identical to SEQ ID NO: 1; and
    administering the hematopoietic stem cell to the subject.

2. The method of claim 1, wherein the promoter is a phosphoglycerate kinase (PGK) promoter.

3. The method of claim 1, wherein the Wpre comprises a sequence at least 95% identical to SEQ ID NO: 1.

4. The method of claim 1, wherein the Wpre comprises a sequence 100% identical to SEQ ID NO: 1.

5. The method of claim 1, wherein the expression cassette comprises one or more enhancer sequences.

6. The method of claim 1, wherein the expression cassette comprises a polypurine tract (PPT).

7. The method of claim 1, wherein the expression cassette comprises a polyadenylation (polyA) signal sequence.

8. The method of claim 1, wherein the expression cassette comprises one or more of the following sequences:
   i) a packing signal sequence;
   ii) a truncated Gag sequence;
   iii) a Rev responsive element (RRE);
   iv) a central polypurine tract (cPPT);
   v) a central terminal sequence (CTS); and
   vi) an upstream sequence element (USE).

9. The method of claim 1, wherein following said contacting the hematopoietic stem cell with the recombinant lentivirus vector, PKLR is expressed at detectable levels in the hematopoietic stem cell.

10. The method of claim 1, wherein following said administration, the hematopoietic stem cell is engrafted in the subject.

11. The method of claim 1, wherein the hematopoietic stem cell is an autologous hematopoietic stem cell obtained from the subject.

12. The method of claim 9, wherein the hematopoietic stem cell is an autologous hematopoietic stem cell obtained from the subject.

13. The method of claim 1, wherein the method comprises obtaining the autologous hematopoietic stem cell from the subject.

14. A method of treating or preventing Pyruvate Kinase Deficiency (PKD) in a subject in need thereof, comprising:
   administering to the subject a hematopoietic stem cell transduced with a recombinant lentivirus vector comprising an expression cassette, wherein the expression cassette comprises a polynucleotide sequence encoding a pyruvate kinase, liver and red blood cell (PKLR) polypeptide operatively linked to a promoter, wherein the expression cassette comprises a woodchuck hepatitis virus post-transcriptional regulatory element (Wpre), wherein the Wpre comprises a sequence at least 90% identical to SEQ ID NO: 1.

15. The method of claim 14, wherein the hematopoietic stem cell is an autologous hematopoietic stem cell obtained from the subject.

16. The method of claim 15, wherein the method comprises transducing the autologous hematopoietic stem cell with the recombinant lentivirus vector.

17. The method of claim 14, wherein the promoter is a phosphoglycerate kinase (PGK) promoter.

18. The method of claim 14, wherein the Wpre comprises a sequence at least 95% identical to SEQ ID NO: 1.

19. The method of claim 14, wherein the Wpre comprises a sequence 100% identical to SEQ ID NO: 1.

* * * * *

UNITED STATES PATENT AND TRADEMARK OFFICE
CERTIFICATE OF CORRECTION

PATENT NO. : 11,286,501 B2
APPLICATION NO. : 16/094414
DATED : March 29, 2022
INVENTOR(S) : Jose C. Segovia et al.

It is certified that error appears in the above-identified patent and that said Letters Patent is hereby corrected as shown below:

On the Title Page

Assignees:
First Column, Line numbers 25-26:
"INVESTIGACION BIOMFDICA EN RED, M.P., Madrid (ES);"
Should read:
--INVESTIGACION BIOMEDICA EN RED, M.P., Madrid (ES);--

In the Claims

At Column 60, Claim number 13, Line number 1:
"The method of claim 1, wherein the method comprises"
Should read:
--The method of claim 11, wherein the method comprises--

Signed and Sealed this
Ninth Day of August, 2022

Katherine Kelly Vidal
*Director of the United States Patent and Trademark Office*

SEQUENCE LISTING

```
<160> NUMBER OF SEQ ID NOS: 9

<210> SEQ ID NO 1
<211> LENGTH: 677
<212> TYPE: DNA
<213> ORGANISM: Artificial Sequence
<220> FEATURE:
<223> OTHER INFORMATION: Chimeric modified Woodchuck hepatitis virus
      posttranscriptional regulatory element (Wpre)

<400> SEQUENCE: 1
cgagcatctt accgccattt attcccatat ttgttctgtt tttcttgatt tgggtataca      60
tttaaatgtt aataaaacaa aatggtgggg caatcattta cattttagg gatatgtaat     120 tactagttca ggtgtattgc cacaagacaa acatgttaag aaactttccc gttatttacg    180
ctctgttcct gttaatcaac ctctggatta caaaatttgt gaaagattga ctgatattct    240
taactatgtt gctccttta cgctgtgtgg atatgctgct ttaatgcctc tgtatcatgc     300
tattgcttcc cgtacggctt tcgttttctc ctccttgtat aaatcctggt tgctgtctct    360
ttatgaggag ttgtggcccg ttgtccgtca acgtggcgtg gtgtgctctg tgtttgctga    420
cgcaaccccc actggctggg gcattgccac cacctgtcaa ctcctttctg gactttcgc     480 tttccccctc ccgatcgcca cggcagaact catcgccgcc tgccttgccc gctgctggac    540 agggctagg ttgctgggca ctgataattc cgtggtgttg tcggggaagg gcctgctgcc     600
ggctctgcgg cctcttccgc gtcttcgcct tcgccctcag acgagtcgga tctcccttg    660 ggccgcctcc ccgcctg                                                   677

<210> SEQ ID NO 2
<211> LENGTH: 28
<212> TYPE: DNA
<213> ORGANISM: Human immunodeficiency virus 1

<400> SEQUENCE: 2 tttaaagaa aaggggggat tgggggt                                         28

<210> SEQ ID NO 3
<211> LENGTH: 205
<212> TYPE: DNA
<213> ORGANISM: Human immunodeficiency virus 1

<400> SEQUENCE: 3
tccttgggtt cttgggagca gcaggaagca ctatgggcgc agcgtcaatg acgctgacgg     60
```

```
tacaggccag acaattattg tctggtatag tgcagcagca gaacaatttg ctgagggcta    120
ttgaggcgca acagcatctg ttgcaactca cagtctgggg catcaagcag ctccaggcaa    180
gaatcctggc tgtggaaaga tacct                                         205
```

<210> SEQ ID NO 4
<211> LENGTH: 566
<212> TYPE: DNA
<213> ORGANISM: Homo sapiens

<400> SEQUENCE: 4

```
attatggtaa atccacttac tgtctgccct cgtagccatc gagataaacc ctaccgggta     60
ggggaggcgc ttttcccaag gcagtctgga gcatgcgctt tagcagcccc gctgggcact    120
tggcgctaca caagtggcct ctggcctcgc acacattcca catccaccgg taggcgccaa    180
ccggctccgt tctttggtgg ccccttcgcg ccaccttcta ctcctcccct agtcaggaag    240 ttccccccg ccccgcagct cgcgtcgtgc aggacgtgac aaatggaagt agcacgtctc    300
actagtctcg tgcagatgga cagcaccgct gagcaatgga agcgggtagg cctttggggc    360
agcggccaat agcagctttg ctccttcgct ttctgggctc agaggctggg aaggggtggg    420
tccgggggcg ggctcagggg cgggctcagg ggcggggcgg gcgcccgaag gtcctccgga    480
ggcccggcat tctgcacgct tcaaaagcgc acgtctgccg cgctgttctc ctcttcctca    540
tctccgggcc tttcgacctg cagccc                                         566
```

<210> SEQ ID NO 5
<211> LENGTH: 138
<212> TYPE: DNA
<213> ORGANISM: Human immunodeficiency virus 1

<400> SEQUENCE: 5

```
tcgacgcagg actcggcttg ctgaagcgcg cacggcaaga ggcgaggggc ggcgactggt     60
gagtacgcca aaattttga ctagcggagg ctagaaggag agagatgggt gcgagagcgt    120
cagtattaag cggggag                                                   138
```

<210> SEQ ID NO 6
<211> LENGTH: 236
<212> TYPE: DNA
<213> ORGANISM: Artificial Sequence
<220> FEATURE:
<223> OTHER INFORMATION: Modified LTR nucleic acid sequence

<400> SEQUENCE: 6

```
tggaagggct aattcactcc caacgaagac aagatctgct ttttgcttgt actgggtctc     60
tctggttaga ccagatctga gcctgggagc tctctggcta actagggaac ccactgctta    120
agcctcaata agcttgcct tgagtgcttc aagtagtgtg tgcccgtctg ttgtgtgact    180
ctggtaacta gagatccctc agacccttt agtcagtgtg aaaatctct agcagt         236
```

<210> SEQ ID NO 7
<211> LENGTH: 235
<212> TYPE: DNA
<213> ORGANISM: Artificial Sequence
<220> FEATURE:
<223> OTHER INFORMATION: Modified LTR nucleic acid sequence

<400> SEQUENCE: 7

```
tggaagggct aattcactcc caacgaagac aagatctgct ttttgcttgt actgggtctc     60
```

```
tctggttaga ccagatctga gcctgggagc tctctggcta actagggaac ccactgctta    120
agcctcaata aagcttgcct tgagtgcttc aagtagtgtg tgcccgtctg ttgtgtgact    180
ctggtaacta gagatccctc agaccctttt agtcagtgtg gaaaatctct agcag         235
```

<210> SEQ ID NO 8
<211> LENGTH: 516
<212> TYPE: DNA
<213> ORGANISM: Artificial Sequence
<220> FEATURE:
<223> OTHER INFORMATION: Synthesized codon optimized human PKLR promoter
      sequence

<400> SEQUENCE: 8

```
tccacggggt tggggttgcg ccttttccaa ggcagccctg ggtttgcgca gggacgcggc     60
tgctctgggc gtggttccgg gaaacgcagc ggcgccgacc ctgggtctcg cacattcttc    120
acgtccgttc gcagcgtcac ccggatcttc gccgctaccc ttgtgggccc cccggcgacg    180
cttcctcgtc cgcccctaag tcgggaaggt tccttgcggt tcgcggcgtg ccggacgtga    240
caaacggaag ccgcacgtct cactagtacc ctcgcagacg gacagcgcca gggagcaatg    300
gcagcgcgcc gaccgcgatg ggctgtggcc aatagcggct gctcagcagg ggcgcccgag    360
agcagcggcc gggaagqggc ggtgcgggag gcggggtgtg gggcggtagt gtgggccctg    420
ttcctgcccg cgcggtgttc cgcattctgc aagcctccgg agcgcacgtc ggcagtcggc    480
tccctcgttg accgaatcac cgacctctct ccccag                              516
```

<210> SEQ ID NO 9
<211> LENGTH: 677
<212> TYPE: DNA
<213> ORGANISM: Woodchuck hepatitis virus

<400> SEQUENCE: 9

```
cgagcatctt accgccattt attcccatat ttgttctgtt tttcttgatt tgggtataca     60
tttaaatgtt aataaaacaa aatggtgggg caatcattta cattttttagg gatatgtaat    120 tactagttca ggtgtattgc cacaagacaa acatgttaag aaactttccc gttatttacg    180
ctctgttcct gttaatcaac ctctggatta caaaatttgt gaaagattga ctgatattct    240
taactatgtt gctcctttta cgctgtgtgg atatgctgct ttaatgcctc tgtatcatgc    300
tattgcttcc cgtacggctt tcgttttctc ctccttgtat aaatcctggt tgctgtctct    360
ttatgaggag ttgtggcccg ttgtccgtca acgtggcgtg gtgtgctctg tgtttgctga    420
cgcaaccccc actggctggg gcattgccac cacctgtcaa ctcctttctg gactttcgc    480 tttccccctc ccgatcgcca cggcagaact catcgccgcc tgccttgccc gctgctggac    540
aggggctagg ttgctgggca ctgataattc cgtggtgttg tcggggaagg cctgctgcc    600 ggctctgcgg cctcttccgc gtcttcgcct tcgccctcag acgagtcgga tctccctttg    660
ggccgcctcc ccgcctg                                                    677
```